US011646104B2

United States Patent
Ellis et al.

(10) Patent No.: US 11,646,104 B2
(45) Date of Patent: May 9, 2023

(54) HEALTH MONITORING SYSTEM WITH MODULAR PROCESSING ARCHITECTURE

(71) Applicant: Koneksa Health Inc., New York, NY (US)

(72) Inventors: Robert Davis Ellis, New York, NY (US); Peter John Kelly, London (GB); Josh Feldman, New York, NY (US); Juanita Yim, New York, NY (US)

(73) Assignee: Koneksa Health Inc., New York, NY (US)

( * ) Notice: Subject to any disclaimer, the term of this patent is extended or adjusted under 35 U.S.C. 154(b) by 140 days.

(21) Appl. No.: 17/194,058

(22) Filed: Mar. 5, 2021

(65) Prior Publication Data

US 2022/0284993 A1    Sep. 8, 2022

(51) Int. Cl.
  *G06Q 10/00*   (2012.01)
  *G16H 10/20*   (2018.01)
  *G16H 50/70*   (2018.01)

(52) U.S. Cl.
  CPC .............. *G16H 10/20* (2018.01); *G16H 50/70* (2018.01)

(58) Field of Classification Search
  CPC ............................... G16H 10/20; G16H 50/70
  See application file for complete search history.

(56) References Cited

U.S. PATENT DOCUMENTS

| | | |
|---|---|---|
| 10,909,312 B1 | 2/2021 | Sieling et al. |
| 11,250,952 B1 | 2/2022 | Kimak |
| 2003/0036683 A1 | 2/2003 | Kehr et al. |
| 2008/0077436 A1 | 3/2008 | Muradia |
| 2011/0161107 A1 | 6/2011 | Goldberg et al. |

(Continued)

FOREIGN PATENT DOCUMENTS

EP    2185065 B1    1/2013

OTHER PUBLICATIONS

Calm + Oura Sleep Study, https://clinicaltrials.gov/ct2/show/NCT04514640 (Year: 2020).*

(Continued)

*Primary Examiner* — Aryan E Weisenfeld
(74) *Attorney, Agent, or Firm* — Merchant & Gould P.C.

(57) ABSTRACT

A computer-implemented method performed at a health study management system collects health-related data from data sources, including sensors monitoring system users. A modular data ingestion subsystem includes interface modules adapted to receive health-related data from a respective type of data source. A modular data processing subsystem includes processing modules, processing health-related data to determine derived health indicators. The system receives configuration information for a health study using the health study management system, the configuration information specifying data collection activities, for collecting respective health-related data. The data collection activities include sensor-based data collection activities associated with a sensor type for collecting sensor data, and processing collected sensor data. The data ingestion subsystem and data processing subsystem are configured for the health study. Health-related data is collected from the data sources via the configured data ingestion subsystem and processed using the configured data processing subsystem. A study dataset is generated and output.

29 Claims, 21 Drawing Sheets

(56) References Cited

U.S. PATENT DOCUMENTS

| | | |
|---|---|---|
| 2011/0184250 A1 | 7/2011 | Schmidt et al. |
| 2013/0197894 A1 | 8/2013 | Sablinski |
| 2014/0372147 A1 | 12/2014 | White |
| 2016/0217266 A1 | 7/2016 | Damani et al. |
| 2017/0005958 A1 | 1/2017 | Frenkel et al. |
| 2019/0104951 A1 | 4/2019 | Valys et al. |
| 2019/0312815 A1 | 10/2019 | Altman et al. |
| 2020/0211680 A1 | 7/2020 | Sablinski et al. |

OTHER PUBLICATIONS

Afonin, Securing and Extracting Health Data: Apple Health vs. Google Fit, https://blog.elcomsoft.com/2019/01/securing-and-extracting-health-data-apple-health-vs-google-fit/ (Year: 2019).*

Wikipedia "Event-driven architecture", Retrieved from the Internet: https://en.wikipedia.org/w/index.php?title=Event-driven_architecture&oldid=1008280051 (retrieved on Dec. 18, 2021).

Search Report for European Patent Application No. 21186178.6 (dated Jan. 4, 2022).

Search Report for European Patent Application No. 21186184.4 (dated Jan. 10, 2022).

Search Report for European Patent Application No. 21186186.9 (dated Jan. 10, 2022).

Search Report for European Patent Application No. 21186194.3 (dated Jan. 11, 2022).

Greer, "TCP series #3: network packet loss, retransmissions, and duplicate acknowledgements", Accedian, all pages, accessed Jan. 25, 2023, URL: https://accedian.com/blog/network-packet-loss-retransmissions-and-duplicate-acknowledgements/(2017).

* cited by examiner

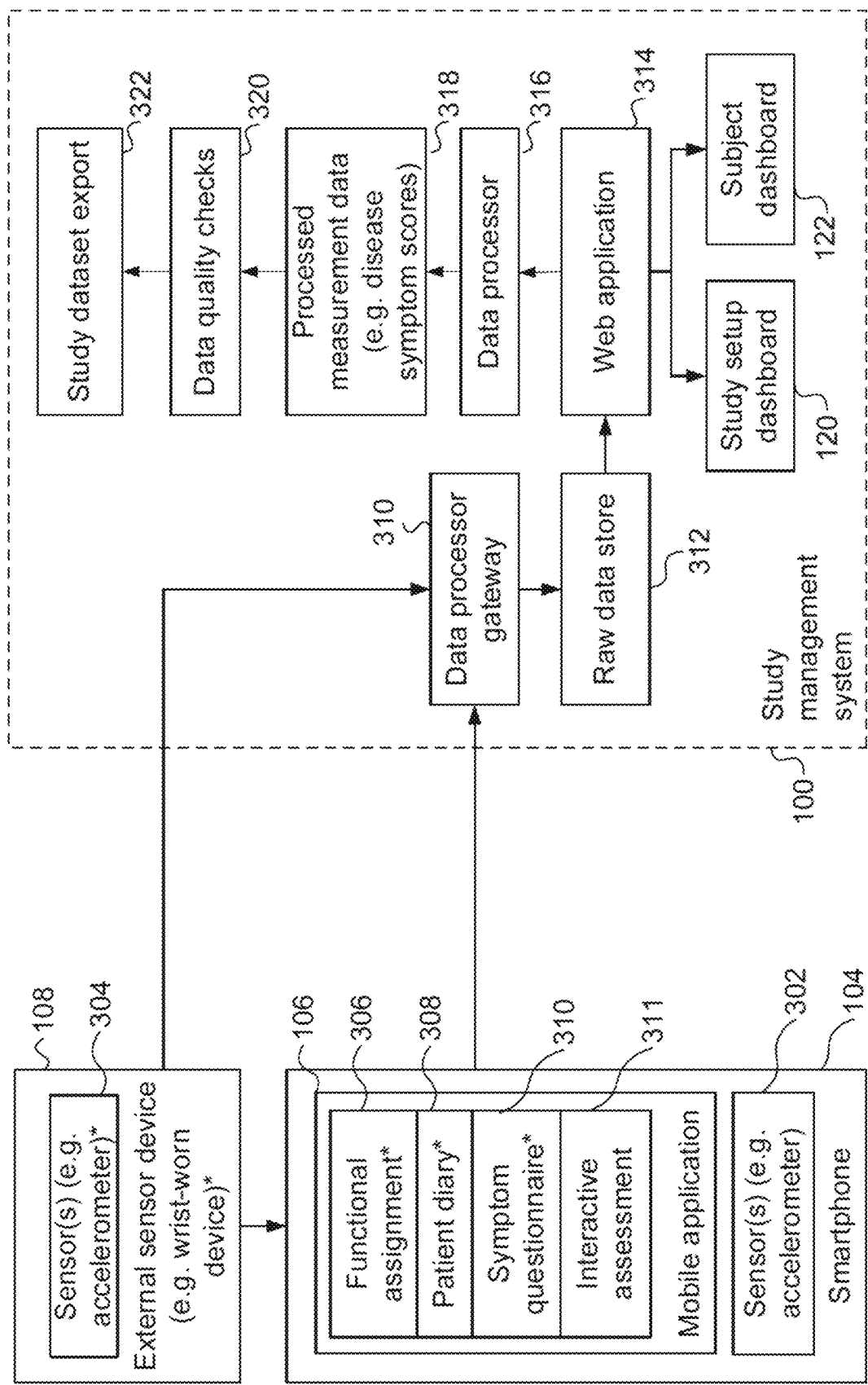

HEALTH MONITORING SYSTEM WITH MODULAR PROCESSING ARCHITECTURE

FIELD OF THE INVENTION

The present invention relates to health monitoring, for example in the context of clinical studies. Particular examples relate to the use of sensors integrated into, or connectable to, personal user devices (such as smartphones) for collecting health status information for processing by a central health monitoring system.

BACKGROUND

Modern personal computer/communication devices such as smartphones, smart watches and personal fitness monitors include various sensors useful for monitoring the health status of users. For example, accelerometers can be used to monitor physical exercise, and infrared sensors can be used to measure heart rate. Many smartphone manufacturers provide health and fitness monitoring applications and services using data collected from such sensors. More specialised medical sensor devices are also available that can be connected to smartphones via Bluetooth, Wi-Fi or similar, such as spirometers and thermometers, and that can use a smartphone to display and process the sensor data produced by the devices.

Some systems developed in the healthcare and clinical research industries provide the ability to track disease symptoms via a smartphone and transmit data to a central system for use by patients and healthcare providers. The typical approach involves either broadly collecting many different health measures for interpretation by a clinician or solutions in which a smartphone application is implemented to track one specific disease with a predetermined set of measures. This limits the adaptability of existing solutions to new problems, with a need to develop bespoke solutions for any new health monitoring application or clinical study. The health monitoring capabilities of user devices, if utilised effectively, could in principle provide new opportunities for, and reduce the cost of, clinical studies and other health monitoring applications (e.g. multiple sclerosis, Parkinson's disease, asthma, etc.), but the cost of developing bespoke mobile device applications and the corresponding server-side data collection and processing infrastructure for such applications can be prohibitively high, and the resulting systems are often inflexible and unable to adapt to changing requirements, including new diseases, complex scheduling, evolving trial designs, and new device and sensor technology.

In addition to the continuous evolution of device and sensor technology, different device manufacturers' devices and associated APIs (application programming interfaces) also typically generate and process data in incompatible formats, further complicating integration of a wide range of devices into a health monitoring system.

SUMMARY

Aspects of the invention are set out in the independent claims and certain preferred features are set out in the dependent claims. Additional aspects and features are set out in numbered clauses at the end of the specific description.

Disclosed herein is a computer-implemented method performed at a health study management system for collecting health-related data from a plurality of data sources. The health-related data may comprise one or more of: data indicative of user health, and source data from which data indicative of user health can be derived. The data sources include sensor devices associated with monitored system users. The method comprises: providing a modular data ingestion subsystem comprising an extensible set of interface modules, each interface module adapted to receive health-related data from a respective type of data source; providing a modular data processing subsystem comprising an extensible set of processing modules, each processing module adapted to process health-related data to determine one or more derived health indicators from the health-related data; and receiving configuration information for a health study to be conducted using the health study management system, the configuration information specifying a plurality of data collection activities, each for collecting respective health-related data from one or more data sources, the data collection activities comprising at least one sensor-based data collection activity associated with a sensor device type to be used for collecting sensor data, and processing to be performed on collected sensor data. The method further comprises configuring the data ingestion subsystem and data processing subsystem in accordance with the configuration information for the health study; collecting health-related data from the data sources via the configured data ingestion subsystem; processing the collected health-related data using the configured data processing subsystem; generating a study dataset based on the processed health-related data; and outputting the study dataset.

Also disclosed is a computer-implemented method performed at a health study management system for collecting health-related data for a health study. The health-related data may comprise one or more of: data indicative of user health, and source data from which data indicative of user health can be computed. The method comprises: receiving health-related data associated with a study participant from one or more devices, the health-related data comprising data generated by a plurality of data collection activities performed using the one or more devices; processing the health-related data received for each data collection activity to format the data in accordance with a common health data model; determining one or more derived health indicators from the formatted health-related data; generating a study dataset using the derived health indicators; and outputting the study dataset.

Also disclosed are a system (e.g. a health monitoring system or health study management system), device or apparatus comprising means, optionally including at least one processor and associated memory, configured to perform any method as set out herein, and a non-transitory computer-readable medium comprising software code adapted, when executed on a data processing apparatus, to perform any method as set out herein.

BRIEF DESCRIPTION OF THE DRAWINGS

Exemplary embodiments of the invention will now be described with reference to the accompanying figures in which:

FIG. 3 illustrates components of the system in more detail;

In the drawings, like reference numerals are used to indicate like elements.

DETAILED DESCRIPTION

Overview

Figure 1:
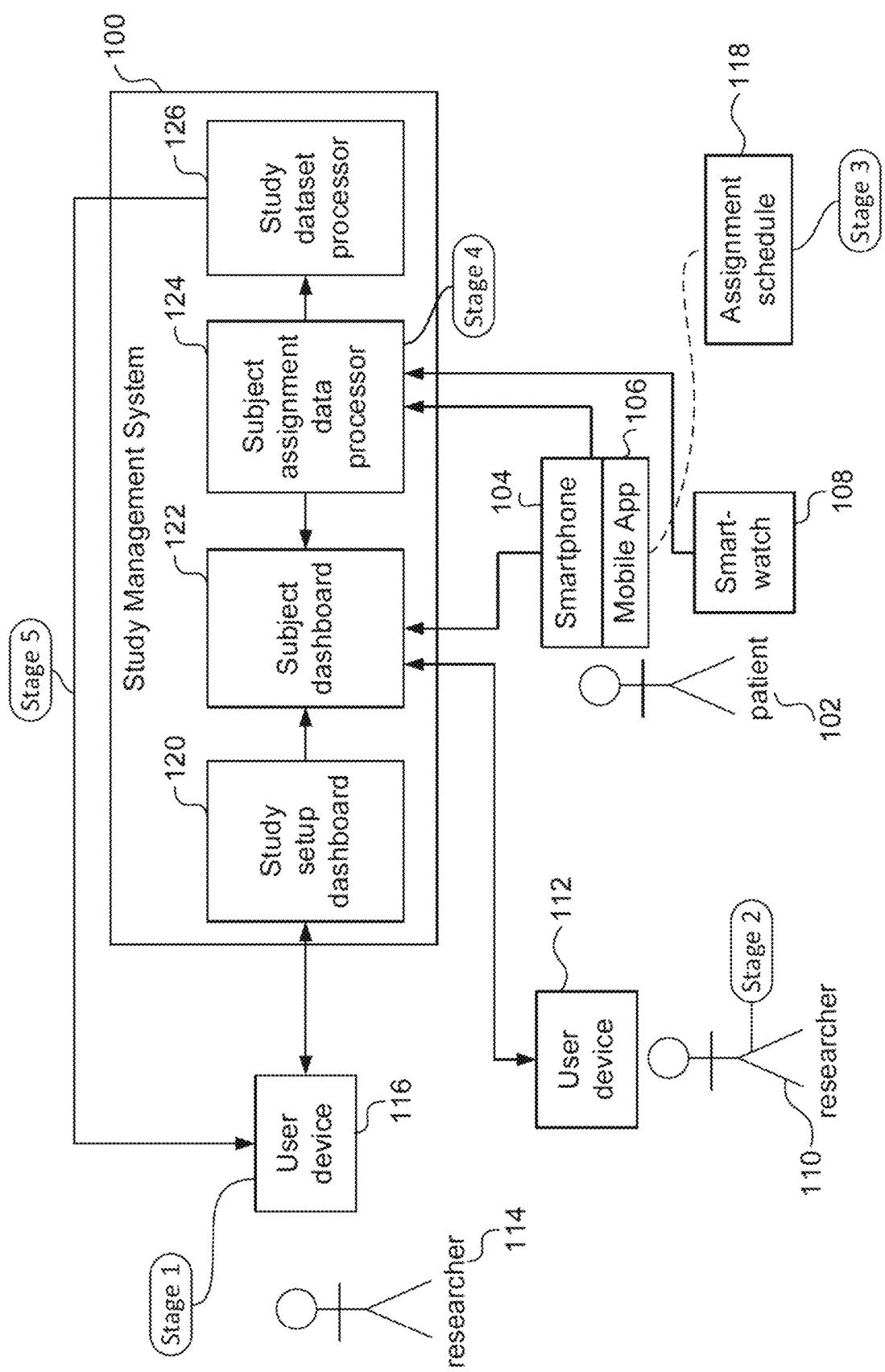
FIG. 1 illustrates a study management system in overview.

Embodiments of the invention provide a system for managing data collection from user devices such as smartphones and various health sensor devices in support of clinical studies. However, while mainly described as a clinical study management system, the described techniques can be used in other health monitoring contexts, for example for monitoring patients with long-term conditions to support treatment.

The system includes a central study management system and a mobile application for smartphones, tablet computers and similar personal computing/communications devices (referred to herein generally as user devices) that is highly configurable to support a wide range of possible clinical studies, with different studies supported within the same mobile application, simultaneously and/or changing over time. The application and server infrastructure are also designed to work effectively in situations of limited bandwidth and intermittent connectivity, so as to support a wide range of possible users in a range of contexts.

The mobile application can be deployed to smartphones or other user devices associated with a large population of study participants (also referred to herein as patients) and can be dynamically configured to concurrently and specifically study symptoms for multiple diseases or for different symptoms for a single disease, rather than being limited to one fixed set of symptoms for one specific disease.

The central study management system allows a study-specific configuration to be constructed, which is then published to an instance of the application on a user device. The system then processes data received from the same instance of the application and matches it to the published configuration, making the data available to the study researchers.

The system also supports collection of different types of data from different sensor devices (both integrated into the user device and separately connected), as well as direct user input (e.g. via symptom questionnaires), using configurable assignment schedules. The system can simultaneously manage multiple study configurations across multiple studies/disease areas, with information sent in near real-time to the central monitoring system where it is tracked for compliance, checked for quality and analysed.

For example, the application can support concurrent studies across two different disease areas. In one example, the application may be configured to study one disease using specific on-screen questionnaires which a patient answers either daily, weekly or monthly. The same mobile application may also be configured to collect sensor data from the user device to study a second disease, with data for both study configurations submitted to the central system, where the data is stored and processed independently in accordance with the respective study configurations. Data collection schedules may be explicitly and separately configured for different study configurations and different data sources (e.g. different sensors).

In a concrete example, the application could be configured to study gait and balance for one disease in conjunction with a wrist-worn accelerometer linked to a smartphone (or other user device), where the application is configured with daily assignments which collect point-in-time data from a smartphone accelerometer and the linked wrist-worn accelerometer collects continuous data over several days—including the times when the patient completes assignments on the smartphone. The data from the smartphone and wrist-worn device is processed using a gait and balance algorithm that calculates distance walked and walking speed. At the same time, the same mobile application and the same device may be used to study sleep with the application configured with a sleep diary and the data recorded from the wrist-worn device used to determine how long the patient slept and how many times they woke up at night. In the second example, the wrist-worn device data is processed with a sleep algorithm.

As another example, in support of a single disease area such as Parkinson's disease, the application may be configured to use specific questionnaires which a study subject answers either weekly or monthly in support of one study. The same application may additionally be configured to collect accelerometer sensor data in combination with a different set of questions which are answered daily, also to study Parkinson's disease, for a second study. Data for each study configuration is uploaded to the central monitoring system where it is made available to the relevant study researches.

Described embodiments can allow pharmaceutical researchers and healthcare providers to study multiple diseases at the same time with one single application and one or more linked devices in a single system across large populations of study participants, instead of deploying multiple applications, devices and systems for different studies or health conditions (e.g. instead of providing one instance of the application and device to study Parkinson's Disease and another instance of the application and a different device to study Asthma). In typical scenarios, any one patient would only be enrolled in one study for one disease at any one time, but there may be multiple studies being run by the system across different patient cohorts simultaneously. The described system can allow this complexity to be managed. At the same time, collection of data by the individual patient can be simplified, reducing the burden on the patient, and management of studies can be simplified by configuring the mobile application for a reduced set of sensor-based assignments and manual user input focused specifically on the symptoms of the particular study.

Embodiments of the system can also simplify the design and implementation of a study by allowing the researcher to readily and remotely study exactly, and only, what they want and need. Researchers can centrally collect and analyse all data from different types of assignments and devices in a single system in a common data model and format.

FIG. 1 illustrates an example implementation of the system in overview. The system comprises a central study management system 100, which interacts with devices associated with a study subject or patient 102. The devices include a user device such as a smartphone 104 or other computing/communications device, running a mobile application 106 for performing data collection and interacting with the central study management system 100. In this example, the user additionally uses a smartwatch 108 with one or more sensor(s) for acquiring health data. Researchers (e.g. 110, 114) also interact with the central study management system using respective user devices 112, 116 such desktop/laptop/tablet personal computers.

While particular examples herein refer to the use of smartphones as the user devices, any other suitable type of user device may be used, e.g. tablet computers, wearable devices etc. Thus, where reference is made herein to smartphones it shall be understood that this is merely by way of example and that other types of computing/communications devices may be substituted.

Preferred embodiments separate the selection and scheduling of the required assignments for the study of a disease from the application 106 and user device 104 deployed to collect data. In particular, the application 106 is designed to be independent of the assignments required for any specific study, and instead provides configurable data collection functionality that can be configured dynamically to support the specific requirements, sensor devices, data collections schedules etc. of particular studies. The same instance of the application can be reconfigured with different sets of assignments (unlike prior approaches which usually encapsulate the study assignments and schedule into a single model in a single system based upon a unique, defined device together with specific data elements). The different assignment configurations and schedules are orchestrated and reconciled by the central study management system 100 so that they are matched to the same patient and operate on the same time basis for that patient.

The central study management system can receive and process data from different instances of the application with different configurations of assignments and different configurations of assignment schedule. In prior approaches, an application to collect sensor data may, for example, record a JSON file of accelerometer values, a questionnaire response may generate a CSV data file and a patient diary may submit a web form. Each data file is stored separately and compilation of the different data files and formats per patient and per study is required before the combined dataset can be analysed. Preferred embodiments can simplify and streamline data collection from multiple data sources and study configurations.

Configuration and operation of a clinical study using the described system involves a number of stages (labelled as Stages 1-5 in FIG. 1), which are discussed in detail in the following sections with reference to FIGS. 1 and 2A-2E.

Stage 1: Study Design is Configured, Published and Assigned to Patient

In the first stage a researcher 114 sets up a new study using a study setup dashboard 120 provided by the study management system, e.g. as a web interface accessed on the researcher's computer device 116.

Figure 2A:
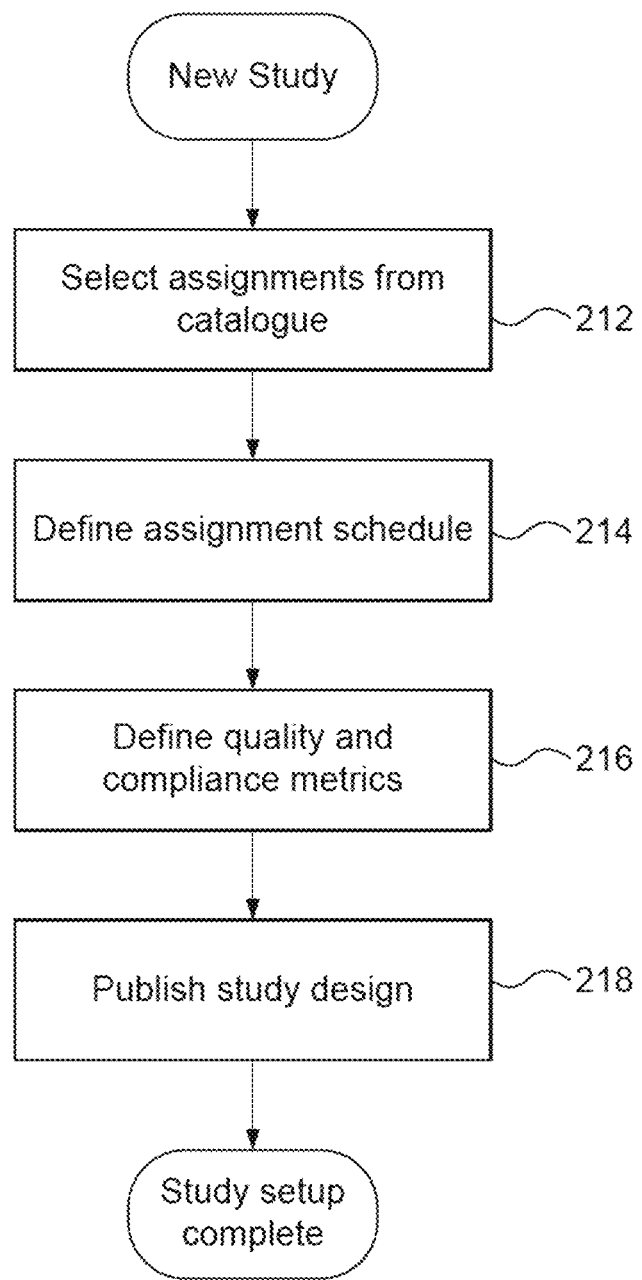
FIGS. 2A-2E illustrate processes for setting up and running a clinical study using the study management system.

The process is illustrated in more detail in FIG. 2A. The researcher selects the study assignments that they require for their study from a catalogue of available assignments in step 212 including assignments made available through the mobile application. For example, in the study of Parkinson's Disease the patient may be assessed for tremor symptoms. These assignments can include any of: device-based assignments, e.g. using sensors (such as an accelerometer) incorporated into or connected to the user device 104, patient diaries, standard clinical questionnaires, functional status assignments etc., all of which employ the mobile application to collect and forward data to the central system. The catalogue of assignments is preferably extensible, e.g. to support new sensor types and user devices and new processing algorithms for analysing sensor data to obtain useful clinically relevant information (e.g. a tremor analysis algorithm based on accelerometer data).

Assignments may be structured into sub-tasks as discussed in more detail below. A given assignment (or assignment sub-task) may be associated with one or more data collection activities (sensor-based and/or non-sensor-based, e.g. user input). A sensor-based data collection activity is associated with a particular sensor device type used to collect data and may also be associated with a predetermined processing algorithm used to process the raw sensor data to derive one or more derived measures (e.g. a step count derived from accelerometer data). These aspects may be predefined and automatically configured based on the user selecting a particular assignment from the catalogue. However, the system may also allow the user to specify the configuration explicitly, e.g. to choose a particular sensor device or particular processing algorithm.

In step 214, the researcher then defines the assignment schedule for the selected assignments, which can be daily, weekly, monthly or otherwise configured according to study requirements. For example, in the study of sleep a patient may be required to complete a daily sleep diary.

The researcher then defines quality and compliance metrics that determine whether the data collected for a patient meets study requirements for completion of assignments in step 216. For example, in one study a patient may be required to wear a wrist-worn accelerometer that records motion for at least 12 hours on each of 7 consecutive days. In another study the patient may be required to wear the device for at least 12 hours one day per week. These requirements can be specified as compliance metrics, against which actual data can later be assessed.

In step 218, the researcher then publishes the study design to the central system based on the assignments added. Data ingestion plugins are enabled at the study level to support the data types that will be ingested for this study. The study design is stored as a configuration in the system that can be viewed and selected by other researchers who are responsible for recruiting, consenting and screening patients to enrol in the study in addition to deploying the configuration to each applicable instance of the mobile application. The system may allow separate instances of the same study configuration to be created (e.g. to support distinct patient populations, or to be run at different times).

Stage 2: Patient is Added to the Study and Study Published to Application

In the second stage, a researcher 110 recruits, consents and screens patients (participants) for participation in the study using a study subject dashboard 122.

Figure 2B:
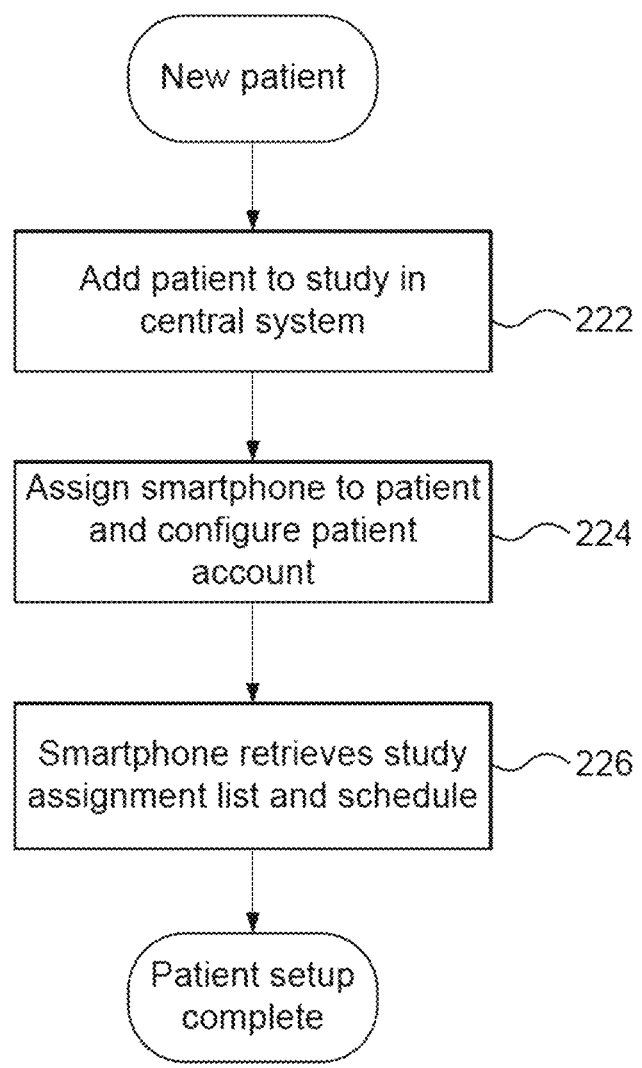

The process is illustrated in FIG. 2B. In step 222, the researcher adds a patient to an instance of the published study in the central system. The researcher then sets up patient access via a smartphone or similar user device and mobile application. In one approach, the application is linked to the patient and in another approach the device is linked to the patient and then an account is made on the application for the patient.

For example, the researcher assigns a user device (e.g. smartphone) with the application installed to the patient (step 224), plus any other devices required to support the study such as a wrist-worn accelerometer, spirometer or other device. An activation code for the application instance installed on the smartphone is generated as part of this step. The activation code is entered in the mobile application, and as a result the mobile application instance/device is assigned to the patient. Other configuration steps may be performed by the researcher or patient to complete user account creation, e.g. setting up a password, accepting user agreements, etc.

Alternatively, access may be provided to the application on a device owned by the patient (e.g. by sending the activation code to the user, who may be able to download the application from an app store, from a web server provided by the system, etc.). Entering the activation code links the application instance to the patient, who can the complete account setup as described above.

Once the patient account setup is complete, the instance of the application then downloads the study configuration, including the list of assignments and assignment schedule, to the smartphone (step 226).

Stage 3— Performing Assignments

In the third stage, assignments scheduled for the study are completed by patients using their devices, in accordance with the schedule (e.g. on a specific scheduled study assignment day).

Figure 2C:
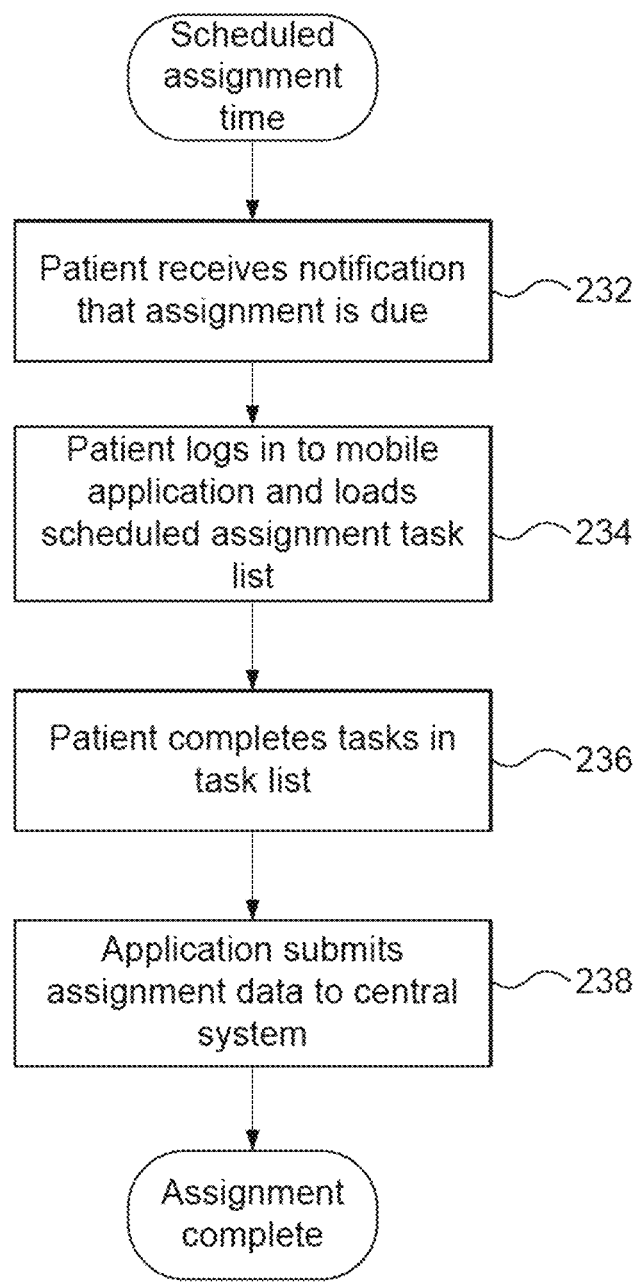

The process is illustrated in FIG. 2C. On any given study assignment day, as defined by the study assignment schedule, the patient receives a notification through the smartphone that an assignment is scheduled to be completed (step 232). In step 234, the patient logs into the application instance on their smartphone, using a password or another authentication mechanism such as fingerprint authentication to confirm that the user completing the assignment corresponds to the patient registered for the study. The required list of assignments is then displayed to the user, and the patient completes the required assignment tasks in step 236.

For example, in the study of Asthma the patient may be required to complete a lung function test on a mobile spirometer which then transmits data to the application instance on the smartphone. The patient may additionally be required to complete a related questionnaire, such as the ACQ (Asthma Control Questionnaire) which records the degree to which the patient's asthma is controlled—independently from or as a result of medication taken.

The data is initially stored in a local database at the mobile application/user device and the system implements data synchronization between the local database and central system. In preferred embodiments, data is uploaded to the central system in step 238 in a batch. For example, given a lung function test and completed questionnaire, the application instance transmits the raw flow volume loop from the mobile spirometer as well as the response to the questionnaire. In other examples such as the study of Parkinson's Disease, the patient may be required to complete a walking assignment in which the phone is placed in a pocket or bag and motion of the patient is recorded by the smartphone accelerometer. The patient may also be required to complete a questionnaire which assesses the severity of their Parkinson's disease symptoms. The uploaded data may then include a data set of accelerometer readings acquired over a particular time period together with the questionnaire inputs.

The data uploads occur periodically based on study configuration, but preferably no less frequently than daily, with upload delayed if necessary until a suitable network connection is available. The study configuration may specify various criteria controlling the batch upload, e.g. times/time windows at which to perform transmission; frequency of transmission; the data collection activities to be grouped in a batch; bandwidth or connectivity requirements, e.g. specifying a minimum bandwidth needed and/or preferred network interface to use, and the like. For example, the application may prioritize transmitting the data via local Wi-Fi and may delay transmission until connectivity via Wi-Fi (or another preferred interface) is available, and/or may use another connection such as cellular services as a backup if the preferred network is not available. Batch transmissions may be scheduled based on explicit timing information provided in the study configuration (e.g. using the dynamic scheduling mechanisms discussed below), with the transmissions being performed at the time(s) specified in the configuration.

The application requires confirmation of receipt by the central study management system and will attempt to re-transmit the data in the absence of a receipt. The application may delete the locally stored data upon receipt of the confirmation from the central system (or some time later, e.g. after a retention delay). While batched transmission of result data may be advantageous especially for devices with restricted bandwidth or intermittent connectivity, alternative implementations may forward data in real-time or near real-time, or may select between immediate transmission and batched transmission based on connectivity of the user device. Transmitted data may be secured using suitable encryption and/or message authentication mechanisms. In one example, HMAC (hash-based message authentication code) headers are added to the transmitted data to ensure message authenticity and integrity.

The mobile application provides necessary prompts and instructions to the user for using external devices. For example, the assignment schedule may prompt the patient to put on or remove a wrist-worn accelerometer that is to be used for an assignment. Instructions for completing assignment tasks and how to use specialised sensor devices may be provided to a user as text, animations, video etc.

External devices such as a smartwatch 108 and specialised sensor devices (e.g. a spirometer) transfer sensor data to the mobile application on the smartphone via a local connection (e.g. Bluetooth, Wi-Fi, USB or other wired or wireless communication channel). However, in some cases, external devices may not be integrated directly into the mobile application but may transmit sensor data via separate applications/subsystems on the smartphone (e.g. provided by a device vendor) and/or via external third-party systems (e.g. using separate network connections bypassing the smartphone 104). The architecture of system 100 provides interfaces for supporting such standalone external data sources as described in more detail later.

Stage 4: Data Processing

Figure 2D:
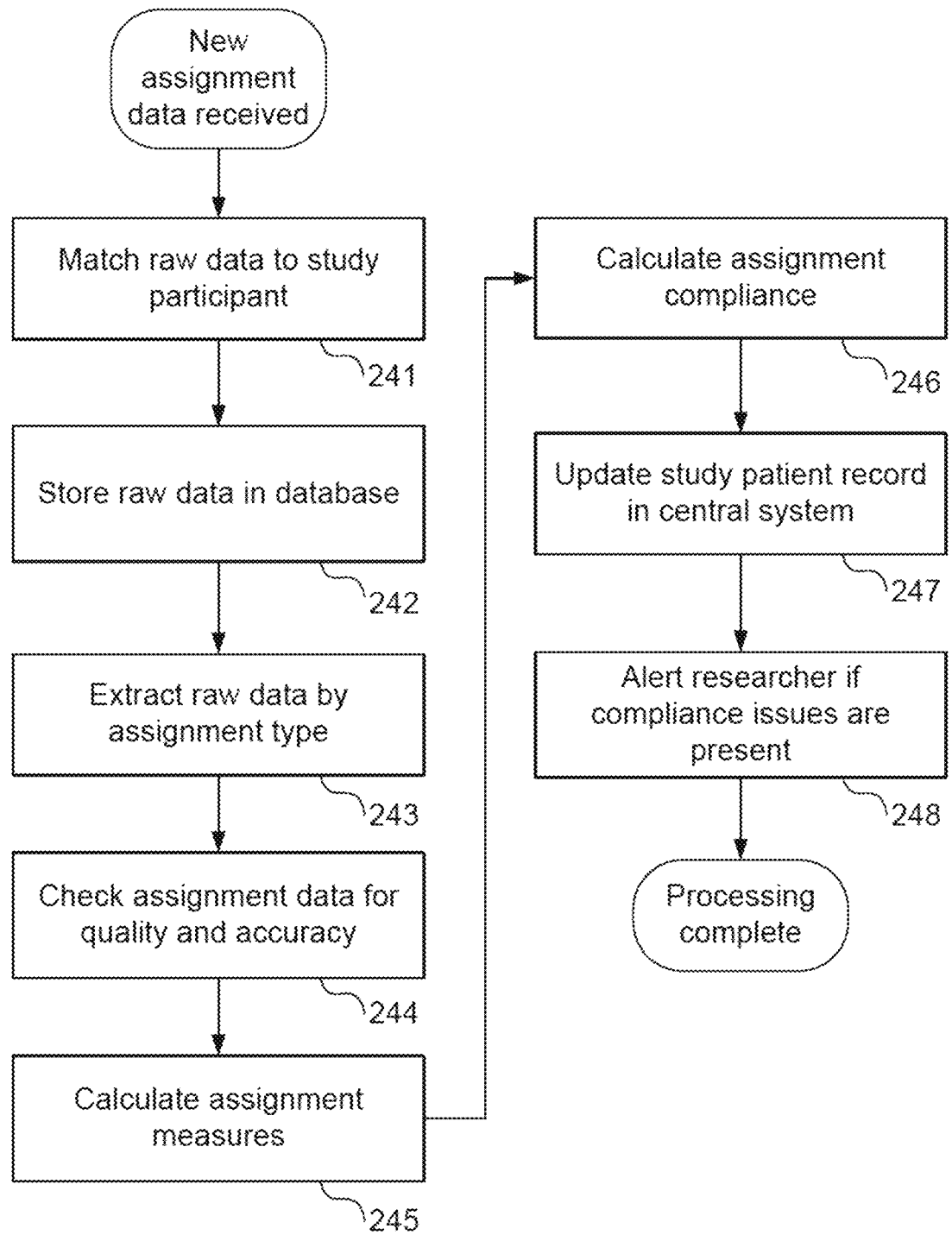

In the next stage, assignment data is processed per patient and study by data processing modules 124 of the central system. The process is illustrated in FIG. 2D.

As discussed above, data from the patient's completed assignment is initially stored on the smartphone and then transmitted to the central system as and when a network connection is available. Upon receipt of the data, the central study management system first determines the current patient, status and study which is associated with the data (step 241). Data which does not match an active study patient is preferably not saved because consent cannot be confirmed (alternatively such data could be stored separately e.g. for auditing or investigation purposes).

If a matching active study patient is identified, then in step 242, the data received is stored as raw data in a database. The data received contains metadata about the patient, assignment name, device used and timestamps. The data received also contains assignment data which is extracted (step 243).

The data itself will vary, based on the assignment. For example, in one implementation the assignment data may be a continuous accelerometer sensor file. In another implementation, the assignment data may be an entry in a sleep diary noting time in bed, time out of bed the next day and then number of times a patient was awake during the night.

Once the raw assignment data has been extracted from the response received it is checked for quality in step 244.

In an example, a sensor data file is received for a walking assignment. The walking assignment requires the patient to walk for 6 minutes—a common test in COPD (chronic obstructive pulmonary disease) and heart disease to assess patient functional status. Quality checks on the received raw data file may show that only 1 minute's worth of data was received. This could be due to the patient not completing the activity, or due to a technical issue e.g. the wrist-worn accelerometer was faulty or low on power and only captured intermittent segments during the 6 minutes of walking. As a further example, a signal analysis may reveal that a heart rate sensor or other sensor was faulty or not used or worn correctly, resulting in an intermittent or low-quality signal. In such cases, an assignment is flagged as "incomplete" because it was not completed as required and/or required data is missing or of insufficient quality. In some implementations, incomplete assignments are logged as such in the central system and notifications issued to clinical personnel to follow up with the patient. In other implementations, an incomplete assignment may trigger automated rescheduling of the assignment for the patient.

Assignments which pass data quality checks are then submitted to an algorithm to calculate required measures in step 245 from the raw data. These required measures are also referred to herein as derived or aggregated measures, and may be derived via various aggregation and other processing techniques, e.g. depending on the sensors involved, the symptoms or other characteristics being studied etc. This step could encompass anything from simple reformatting or aggregation of raw data up to complex signal processing algorithms. Furthermore, for some types of data, such as direct user input (e.g. questionnaires) and some types of sensor data, no additional processing may be needed and this step may be omitted, so that the derived measures are the same as the raw data.

As an example of this step, for the same 6-minute walk test, the algorithm may calculate the number of steps taken, distance walked and walking speed from raw accelerometer data.

The derived measures may include health indicators relevant to the study, i.e. computed values that provide some indication of a participant's health status. Such health indicators may be based on a single data source (e.g. sensor data from a particular sensor or outcomes of a particular interactive assessment), while others may be derived from multiple sources (e.g. a fitness indicator derived from a heart rate measurement, a spirometer measurement and a questionnaire). Some of the computed health indicators may correspond to study end points for the study (e.g. specific outcome measures that are pertinent to the research objectives of the study at hand).

Once any necessary processing has been performed, the derived measures are then stored in the database.

In step 246 assignment compliance is calculated. This may e.g. involve determining whether all necessary measurements and other inputs for an assignment have been carried out. For example, if an assignment includes multiple data collection activities (e.g. a walking assignment, a breathing assignment, and a questionnaire), and one of the activities has not been completed, this may be flagged as non-compliant.

In step 247, the patient's record in the central system is updated to show completion (or partial/non-completion) of the assignment.

As is the case for assignments failing the data quality check (step 244), if compliance issues were identified, a researcher may be notified in step 248, e.g. to enable follow-up with the patient. The non-compliant assignment may be also be rescheduled.

When issues are identified, the researcher may determine an appropriate response based on the type of the issue. For example, the response of the researcher may vary depending on whether the identified issue is non-compliance (e.g. a user did not fully comply with the assignment requirements and instructions) or incomplete/low-quality data for a particular task (which could be due to a technical issue).

Stage 5: Compiling a Study Dataset

Figure 2E:
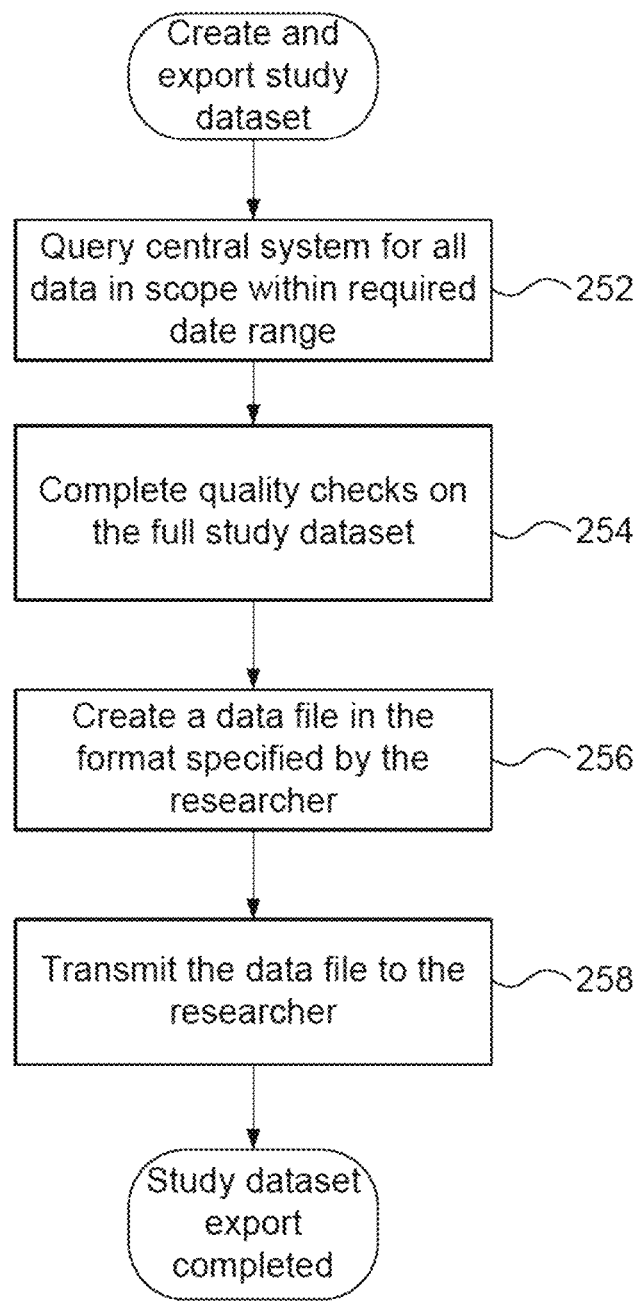

In the final stage, data from all assignments and patients/devices is compiled into a study dataset by a study dataset processing module 126. The process is illustrated in FIG. 2E.

A study dataset may be compiled at intervals during the study and/or at the end of the study. This dataset contains all of the measurements recorded for all of the completed subject assignments. Typically, the data contains any derived measures and health indicators, where applicable along with raw sensor or user input data (e.g. raw sensor measurements or user input data that do not require further processing). Preferred embodiments utilise a common health data model for all data (referred to below as the "common measurement model"), which facilitates combining data from multiple sources, as will be described in more detail later.

In step 252, the study management system provides via database queries and, where appropriate, additional internal analytics, measurement data for all relevant data collected, for all patients registered as participants in the study. The query may be limited to a required date/time range. In some cases, the query could also be limited to a subset of participants.

This initial set of data is checked for quality and completeness (step 254), which may include removal of duplicates or removal of records relating to missed or incomplete assignments/tasks depending upon the requirements of the researcher. After completion of quality checks the data is output in the file format required by the researcher in step 256 and then transmitted to the researcher in step 258 (e.g. by transmitting an output file to a user device 116 of the researcher, or making the output file available for download by a researcher on a web/file server).

Types of Data Collection Activities

The system supports a variety of types of data collection activities to be performed by users and/or their devices as part of the scheduled assignments. Each assignment may correspond to one or more data collection activities performable using a user device.

A given data collection activity is designed to collect a particular set of health-related data. The collected health-related data may include data relevant to or indicative of user health (e.g. a heart rate from a heart rate sensor), and/or source data from which data relevant to or indicative of user health can be derived (e.g. accelerometer data from which sleep quality data can be computed). Thus, the terms "health-related data" or "data indicative of user health" encompass any form of data suitable for providing or deriving information about some aspect of user health.

In preferred embodiments, supported types of data collection activity include sensor-based data collection activities, data input activities, and interactive assessments.

Sensor-based data collection activities use one or more device sensors and/or external sensors connected to the user device (or connected to external data collection platforms) to obtain health-related data in the form of sensor data. Sensors can include general-purpose sensors (e.g. accelerometers built into a smartphone) and/or special-purpose medical sensors (e.g. spirometers, blood pressure sensors etc).

Data input activities are based on direct user input of health-related data values, such as patient questionnaires and health diaries. In such activities a user is prompted to supply specific information, which could include subjective symptom assessments as well as manual input of measurements obtained using non-connected devices (e.g. a weight measurement obtained using conventional scales). Data input activities may implement capture of health-related data in the form of electronic patient reported outcomes (ePRO), clinician-reported outcomes (ClinRO) or equivalent. A data input activity may be implemented as an input form displayed on a display of the user device, with a predefined set of input fields to be completed by a user via data input at the user device (e.g. using touch screen and onscreen keyboard/handwriting recognition, voice recognition etc.).

Interactive assessments can be used to provide more advanced forms of user input-based data collection activities. These may be in the form of interactive activities executed at the user device that require a subject to review and react to prompts (e.g. prompts displayed on a display of the user device, audible prompts output via a device speaker, etc.) by interacting with the device and its user interface (e.g. with a touch screen of the device). The outputs of the activity may not be limited to just the data input by the user in response to prompts. Instead, the activity may measure other characteristics of the interaction to produce relevant measurements, for example response accuracy (e.g. whether or how often a user selects a correct response from available responses), response time (e.g. the time taken by the user to respond to a prompt), whether the subject edits the response before completing/finalizing the response, the pace of inputting the response (as distinct from the response time, e.g. the typing speed), etc. The health-related data generated by interactive assessments is based on the measured characteristics of the user interaction(s).

Interactive assessments assess some aspect of a user's health or capabilities. For example, an interactive assessment may implement a cognitive test, a perceptual test, such as a visual acuity test or auditory test, a dexterity test, or any other form of interactive test for evaluating and/or stratifying subjects based on their health and/or capabilities.

Stroop tests are one example of cognitive tests of this type. A known form of Stroop Test is based on displaying colour names in display colours that do not match the colour names, and measuring the time taken for the test subject to identify the colour names and display colours. As a further example, a dexterity test could involve requiring a user to alternatingly tap two fingers on different highlighted regions of the screen, with both response time and response accuracy (e.g. whether the correct region was tapped, the consistency of correctly alternating fingers when tapping or how close a registered tap was to the highlighted region) being measured, and provided as outputs of the interactive assessment.

The above data collection activity types may also be combined to create more complex assignments. For example, an interactive user input activity such as a cognitive test could additionally collect sensor data from one or more sensors. As another example, a sensor-based activity such as a physical activity associated with a heart rate measurement could be augmented with questionnaire questions assessing the patient's subjective experience of the activity.

The health-related data collected for a particular data collection activity may thus include sensor data, user input data, interactive assessment data, or a combination, depending on the nature of the activity.

The mobile application at the user device supports different modes of data collection for the different supported types of data collection activities. In particular, the application supports collection of data from internal or external sensors in a sensor-based data collection mode, display of input forms for direct data input for data input activities in a data input mode, and running of interactive assessments in an interactive assessment mode. In each case, the data to be collected is defined in the data collection configuration received from the central study management system. Thus, for a sensor-based data collection activity, the data collection configuration specifies which sensor(s) are to be used to obtain sensor data. For a data input activity, the configuration specifies the data fields for which data is to be obtained (and associated prompts to be displayed). Interactive assessments may be provided to the device as executable scripts/code, which can be executed at the user device. These can be directly included in the transmitted configuration, or the configuration may include links to assessment scripts or similar.

A given health study may include data collection activities of any of the above types, in any combination. For example, a study could combine a sensor-based data collection activity with a user input activity or an interactive assessment (or both). Multiple data collection activities of a given type could also be used (e.g. multiple different sensor-based activities for different sensors, multiple different questionnaires or other input activities, and/or multiple interactive assessments). The system could also be extended to support other types of data collection activities.

System Architecture

Further details of the system architecture are shown in FIG. 3. Data flows from smartphone 104 and external sensor device 108 (left) to the central study management system 100 (right). Components marked with an asterisk (*) are configurable per study and disease.

As illustrated, the smartphone 104 (or other personal/mobile communications/computing device) includes one or more sensors 302, such as an accelerometer, infrared sensor etc. suitable for obtaining measurements that are useful for monitoring aspects of patient health, for use in clinical studies and other health assessments. The smartphone also includes the configurable mobile application 106 for operating the data collection process at the mobile device.

One or more external sensor device(s) 108 may be provided, including relevant sensors 304, which can be connected to the smartphone 104 (e.g. via Bluetooth or another local wired or wireless connection). Alternatively, external sensor devices may provide measurement data directly to the central system 100 without interfacing with the smartphone 104. In that case, measurement data may be communicated e.g. via a third-party web service or similar (not shown). Such devices are also referred to herein as standalone sensor devices.

The mobile application 106 is configured via a study configuration to obtain measurement data as part of a patient assignment from internal sensors 302 and/or external measurement device(s) 108. Where an external measurement device 108 is a standalone device that does not communicate via the user device 104 and mobile application 108, the mobile application may be configured to instruct the user to operate the standalone external sensor device at the appropriate time to obtain measurements which are then provided directly to central system 100 via a separate network connection.

The central study management system 100 includes a data processor gateway 318 for receiving data from the mobile application at the smartphone and storing the raw data in a raw data store 312. As noted above, the gateway may also receive measurement data from standalone external devices 108 via an external system, e.g. a device vendor web service, for external devices not configured to integrate with the mobile application 106. Raw data may here refer to unprocessed data as it is received from the mobile application or external device, though in some implementations, some preprocessing or reformatting may be performed before the data is stored or at the mobile application/external sensor device.

The central study management system 100 further includes a web application 314 which provides a web interface implementing the study setup dashboard 120 and subject dashboard for managing study participants (as described above). The study setup dashboard allows assignments and assignment tasks to be configured, including defining sensor data collection activities, building questionnaires etc. Further dashboard interfaces may be provided e.g. for viewing and querying collected data and generating reports. The dashboards are preferably configurable, for example allowing different views on the data to be provided in accordance with the study configuration and schedule.

Additionally, a device management interface (not shown) may be provided to allow management of user and sensor devices across multiple vendors. This may be implemented with a modular approach using device vendor APIs that allows the creation of users and management of devices via the device management interface (e.g. to allow assignment of devices to users, removal of assignments, etc.)

Collected data from the raw data store 312 is processed by one or more data processor modules 316, for example to derive required health metrics or health indicators 318 from the raw sensor data (e.g. step count from accelerometer data, disease symptom scores and the like), as previously described. The central system also performs data quality checks 320 and generates a study dataset 322 for export to the researcher(s) for the study as previously discussed.

Note that, in practice, the central system 100 may be implemented as a single server implementing various modules, or alternatively may be distributed across multiple computing devices, for example one or more database servers, web servers, data processing servers etc.

While a single smartphone 104 and external sensor device 108 are shown for illustrative purposes, in practice the central system 100 typically interacts with many such devices, associated with many different users (study participants/patients).

Different internal sensors 302 and external sensor devices 108, and different processing modules 316, may be selected as a function of different study requirements. For example, in a study of sleep, an actigraphy device may be used to collect movement data overnight. This movement data is then processed by suitable algorithms (e.g. publicly available and validated algorithms may be used) which derive properties of sleep such as total sleep time, number of times awake etc. In another example, the external sensor device 108 may be a mobile spirometer. The patient blows into the mobile spirometer two or more times and the mobile spirometer records the flow of the patient's breath through the device. The flow data is then processed to calculate lung function measurements. In other examples, the external sensor device 108 may be a single lead ECG (electrocardiogram) sensor, which is a sensor applied via a patch which the patient sticks to their chest near the heart. In this example, the electrical signals of the heartbeat are recorded and an algorithm processes the data to derive the number of heartbeats per minute and other supported measures.

At the smartphone 104, the assignments are performed by a functional assignment module 306. As described in more detail below, this includes an event-based scheduling engine for scheduling assignments and individual data collection activities. In addition to sensor-based data collection, other forms of data collection may be performed as part of the assignments. For example, the mobile application may include a patient diary module 308 and a symptom questionnaire module 310 to implement data input activities and an interactive assessment module 311 for performing interactive assessments. Like the sensor-based assignments, these are scheduled using the scheduling engine. Data collected from sensors, in the patient diary, from the symptom questionnaire(s) and from interactive assessments is configurable for each study.

Mobile Application Configuration

Figure 4:
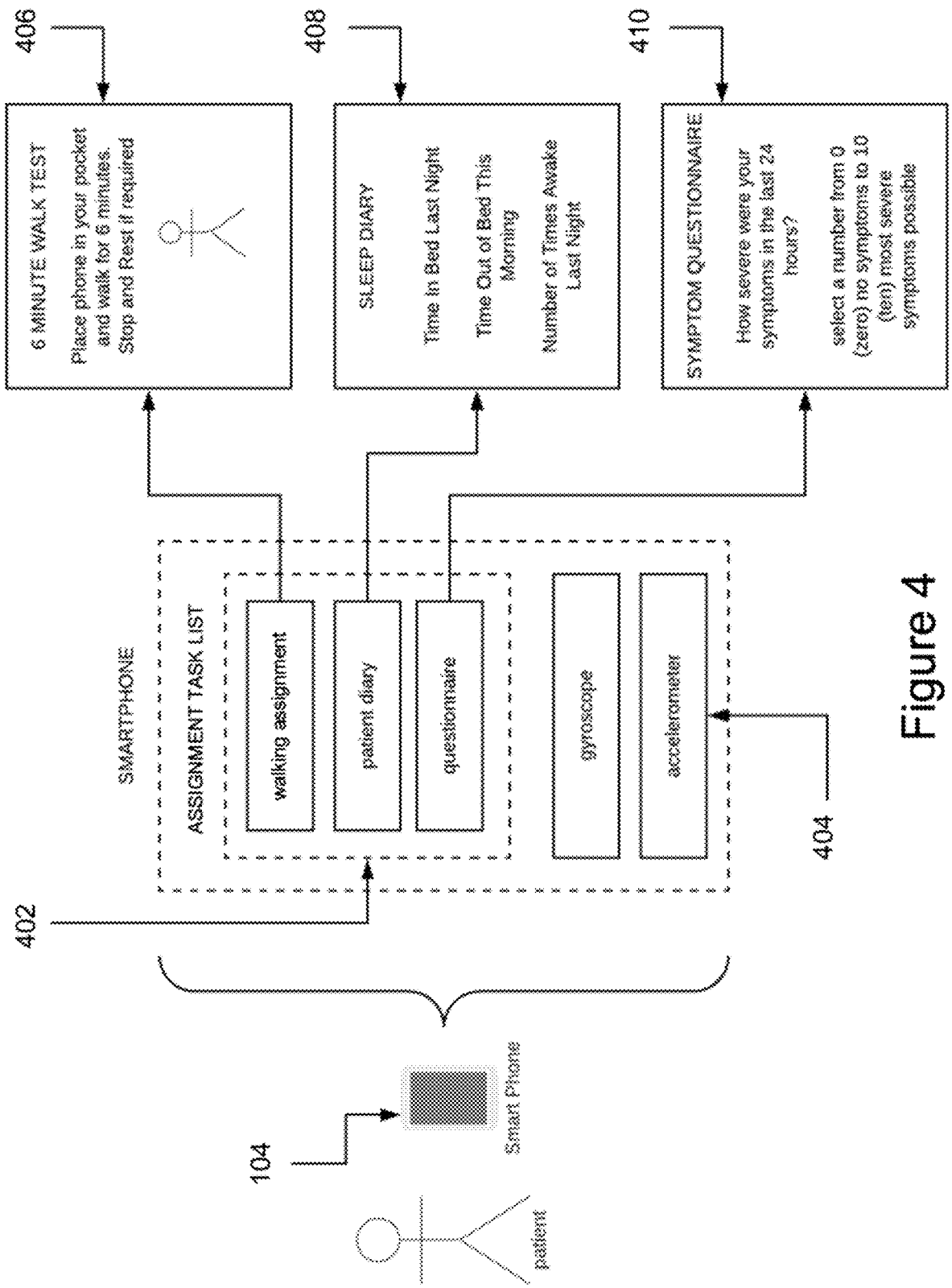
FIG. 4 illustrates a study configuration implemented on a user device.

FIG. 4 illustrates an example configuration of the user device and mobile application for a particular study. The patient logs into the smartphone 104 and a task list 402 of assignments is displayed. One or more of the assignments may make use of the smartphone sensors 404 (in this example a gyroscope and accelerometer are used for a walk test).

In the example illustrated, the patient is required to complete three assignments: a walking assignment 406 (based on sensor data), a sleep diary 408 (based on user data input) and a symptom severity questionnaire 410 (based on user data input). User data input is typically in the form of text input, e.g. via an onscreen keyboard/touch interface, or via voice recognition. Other studies of other diseases may implement a different task list configuration. For example, while in this example only one of the assignment tasks is based on sensor data, in other studies, there may be multiple sensor data based assignment tasks, which may utilise different sensors or the same sensors (e.g. in this case instead of a sleep diary, sensor-based sleep monitoring could be performed).

Depending on the nature of the assignments, data collection may involve active user tasks (as in this example, where a user is prompted via information displayed on the device screen to perform a specific task, such as walking, which is then monitored using sensors) and/or may involve passive data collection (e.g. sleep monitoring, step count monitoring over a particular period). Furthermore, individual assignment tasks (including multiple sensor-based tasks) may be performed concurrently or at different times, depending on study configuration.

Figure 5B:
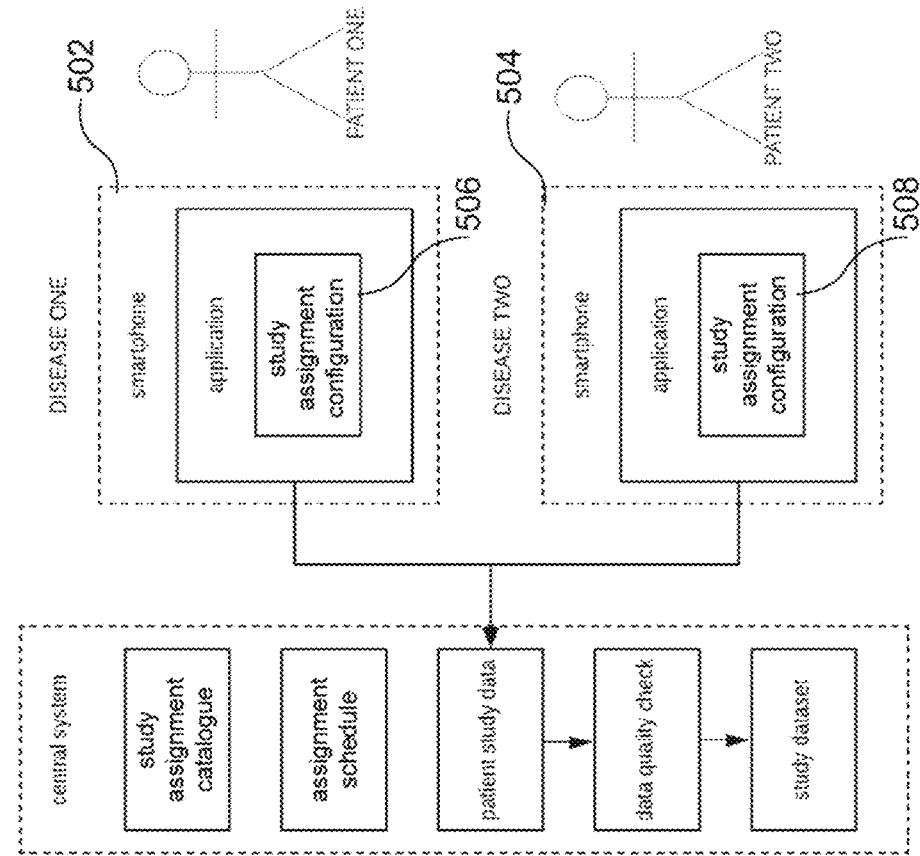
FIGS. 5A-5B illustrate use of the system to support multiple studies across different devices.
Figure 5A:
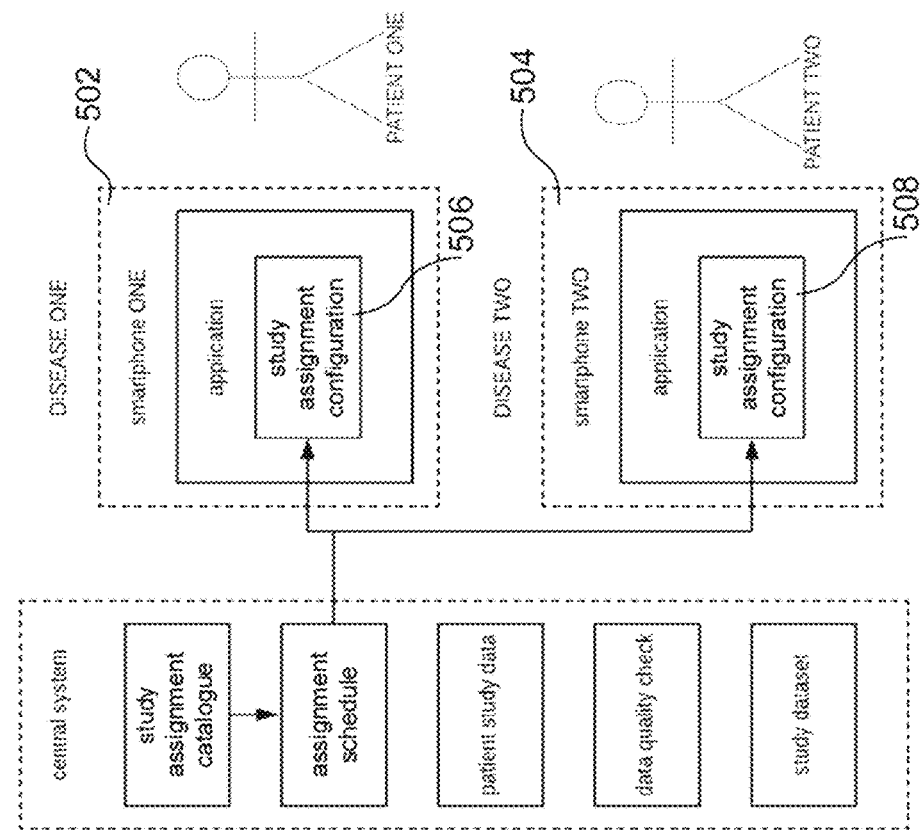

FIGS. 5A-5B illustrate how multiple studies can be configured from the central study management system. FIG. 5A illustrates the setup phase, in which different assignment configurations 506, 508 (in this example relating to two distinct diseases) are pushed to two smartphones 502, 504. In this example, this involves configuration of a set of assignments and a study assignment schedule for disease ONE in patient ONE in an instance of the application installed on smartphone ONE (502); and separate configuration of assignments and an associated schedule for disease TWO in patient TWO in an instance of the application installed on smartphone TWO (504).

In the deployment/data collection phase shown in FIG. 5B, each smartphone then executes the data collection activities specified by its respective study assignment configuration and transmits the resulting data back to the central system. In this example, patient ONE completes assignments in the instance of the application installed on smartphone ONE and patient TWO completes the assignments in the instance of the application on smartphone TWO. Data is submitted from smartphone ONE and TWO and processed by the central system.

System Implementation

The following sections discuss in more detail various aspects of the technical implementation of the above system.

In a preferred implementation, the described system is based on an extensible architecture adapted to interact with an extensible range of user devices, external sensor devices, and external services. The architecture is extensible via plugins to support new devices and services. The central data handling systems are designed to be device-agnostic.

That device agnosticism is achieved in part by way of a data ingestion pipeline for taking device and sensor data from an extensible list of mobile, wearable and other sensor devices. This pipeline operates regardless of data transport method, supporting an extensible list that includes Bluetooth, HTTP (Hypertext Transfer Protocol)/HTTPS (HTTP Secure), and SFTP (Secure Sockets/SSH File Transfer Protocol). This pipeline also operates regardless of data format, supporting an extensible list that includes JSON (JavaScript Object Notation), CSV (Comma-Separated Values), and TSV (Tab-Separated Values). Note that supported data transports and formats are given by way of example only and any suitable formats and transmission protocols may be used.

The modularized architecture for device integration using a common pipeline that is extensible by configuration allows the system to take in data from a variable set of sources in a variable set of formats via a variable set of transport methods, and process all of it in an equivalent manner. In particular embodiments, the described architecture can help to address a variety of technical challenges and support a variety of complex functions, such as:

Data Searchability: The ability to query against data from any source in the same manner.

Data Validity: The ability to compare any measurement against configurable reliability thresholds to determine during initial processing whether or not the data from a particular measurement is reliable and generates appropriate alerts for low-quality incoming data.

Data Sparsity: The ability to detect whether there is missing data in a data set and automate backfilling algorithms to complete the data set, including deciding when/whether to perform backfilling and how backfilling is implemented.

Device Comparison: The ability to compare and make use of the data from multiple sources without needing a custom processing module for every configuration or combination of devices.

Task Compliance: The ability to run a uniform compliance engine on any measurement type and generate high-visibility compliance for each user on whether or not they are using the sensors as instructed under different protocols.

Configurability: The ability to configure different combinations from a list of assignment tasks and measures and deploy them within the same platform to different sets of users/study participants. Each study protocol typically requires a different configuration and any single study may require multiple configurations, all of which drives the technical challenge described under Modularity below.

Dynamic Evolution and Decision Making: Allow, via configuration, for combinations of measures for a single person to change over the observation period.

Modularity: The ability to input and process data from X sources in Y formats via Z transport methods per configuration is provided by way of an extensible interface for data ingestion plugins, with the ability to select existing plugins or create new ones to support a particular study protocol. This approach can generally be more scalable than creating distinct data pipelines for each data type. The modular, extensible pipeline preferably allows the source, transport, and format to be configured for different data sources. The system defines a standard interface schema for use by data ingestion plugins, allowing for the creation of an extensible list of supported sensor devices.

In an embodiment, the architecture includes one or more of the following components:

A common measurement model

An external device and services API (application programming interface) for obtaining data from standalone external sensor devices (e.g. via third party/device vendor services)

A mobile application API for obtaining data from the user device (e.g. smartphone) and its integrated sensors and/or from sensor devices directly connected to the user device Common Measurement Model Underlying the unified data ingestion pipeline is a Common Measurement Model. This model consists of a wrapper with timestamps, completion metadata, and information that links the measurement to the raw data file(s) from which it is generated, followed by a data field that contains all of the sensor readings pertaining to a single measurement. Thus, a single "measurement" in this model may include multiple sensor readings from the same or different sensors. Each sensor reading consists of:

Value: the value of the sensor reading

Unit: the unit of the reading, selected from an extensible list of units

Type: the data type of the value (e.g. integer, float, text, percentage, etc.)

Measure: a human-readable identifier for this reading (i.e. "FEV1")

While discussed mainly in relation to sensor readings, the same format can be used for other data that does not originate from a sensor, e.g. data values input manually by a user or health-related data obtained from interactive assessments. Thus the term "measurement" in this context may indicate, but does not necessarily indicate, that a measurement has taken place; "measurement" may accordingly refer to other forms of data collection and the measurement model can be used to represent any kind of health-related data from any source (the common measurement model may also be referred to as a common health data model).

If a measurement in whole consists of data from multiple sensors or sources, each would result in a distinct reading within the measurement. Any derived measurements are also persisted within the readings section. However, in a simple case, a measurement may also consist of a single sensor reading from a single sensor, or other single value.

As every measurement is stored in the same format, they can all be processed and configured in the same way. When setting up a study to take in measurements, the user configures from a list of already supported measures, or can add a module for a new measurement type, providing some meta information as to how the measure should be ingested (e.g. format, transport) and can set up its processing configuration. This configuration is then used in the data ingestion pipeline in one of two external interfaces as described in more detail below.

In one implementation, measurements are stored, transmitted and processed as events in an event-based processing pipeline. The event-based processing pipeline allows system components to generate events (e.g. measurement events) and submit these to an event-handling system. Other system components can subscribe to particular events. When an event matching an event subscription is received, it is forwarded to the subscribing system component, which can then process the event (e.g. containing a measurement). Some possible outcomes of this subscription may be, purely by way of example:

updating a participant's compliance for the week updating the participant's latest data such that their most recent measurements can be viewed by a researcher triggering a data science algorithm e.g. to process sensor data The measurement event schema includes a derived unique key and an event value that contains the readings (individual data values). Example 1 below illustrates (using pseudocode) a schema for an event key:

```
export interface IEventKey {
  /** The source of event (3rd party vendor, our own app). */
  eventSource: 'AppleHealth' | 'Spirometer' | 'Some 3rd Party Vendor' // etc
  /** The type of event. Some examples listed */
  eventType: 'ACTIGRAPH' | 'SPIROMETRY' | 'BATTERY' | 'STEPS' | 'ECG' | 'SLEEP'
  /** The user identifier. */
  userId: string;
  /** The device identifier. */
  deviceId?: null | undefined | string;
  /** Beginning and end timestamps for measurement event. */
  timestamp: {
    // ISO-8601 timestamp representing the start of the measurement period.
    startsAtISO8601: string;
    // ISO-8601 timestamp representing the end of the measurement period.
    endsAtISO8601: string;
  },
}
```

Example 1

Example 2 below illustrates (using pseudocode) a schema for an event value, storing the raw sensor readings for a sensor measurement event, in this case from an accelerometer:

```
export interface IEventValue {
  readings: [
    {
      value: 30.12321382132
      measure: 'xAccelerometer'
      unit: 'm^2/s'
      type: 'double'
    },
    {
      value: 27.12321382132
      measure: 'yAccelerometer'
      unit: 'm^2/s'
      type: 'double'
    },
    {
      value: 1.12321382132
      measure: 'zAccelerometer'
      unit: 'm^2/s'
      type: 'double'
    },
  ]
}
```

Example 2

Example 3 below illustrates (using pseudocode) a schema for an event value, in this case storing derived or aggregated measurement data (derived from raw sensor data):

```
export interface IEventValue {
  readings: [
    {
      value: 0.73
      measure: 'wear'
      unit: '%'
      type: 'double'
    },
    {
      value: 2200
      measure: 'steps'
      unit: 'count'
      type: 'integer'
    },
    {
      value: 637
      measure: 'timeAsleep'
      unit: 'minutes'
      type: 'integer'
    },
  ]
}
```

Example 3

The derived/aggregated measurements of Example 3 may have been obtained from raw sensor readings by an aggregation module, as described in more detail below. In this example, the measurement includes three "readings" or sub-values: a wear percentage, a step count, and a sleep time, which may have been derived from a set of accelerometer measurements (as illustrated in Example 2).

Note that the code examples given above are meant to provide representative examples and in practice the specific data structures can be adapted based on the requirements of an implementation. Also, the specific data sources (e.g. AppleHealth™), event types and measures may vary depending on implementation, application context and the study being conducted.

The key data and value date together define a measurement event. Measurement events can be communicated between processing modules in this format (e.g. as events in the event-based processing architecture) and are preferably also persisted to a measurement database in this format (e.g. as key-value pairs in a key-value store). However, other formats for communicating and storing data may be used. For example, the measurements may be stored in a relational database table using a set of table fields for storing the key information and value information outlined above.

The system preferably enables searching, querying, and/or collation of measurement data based on one or more of the key data elements (e.g. to retrieve data for specific user identifiers or device identifiers).

Data Ingestion Pipeline Architecture

Figure 6A:
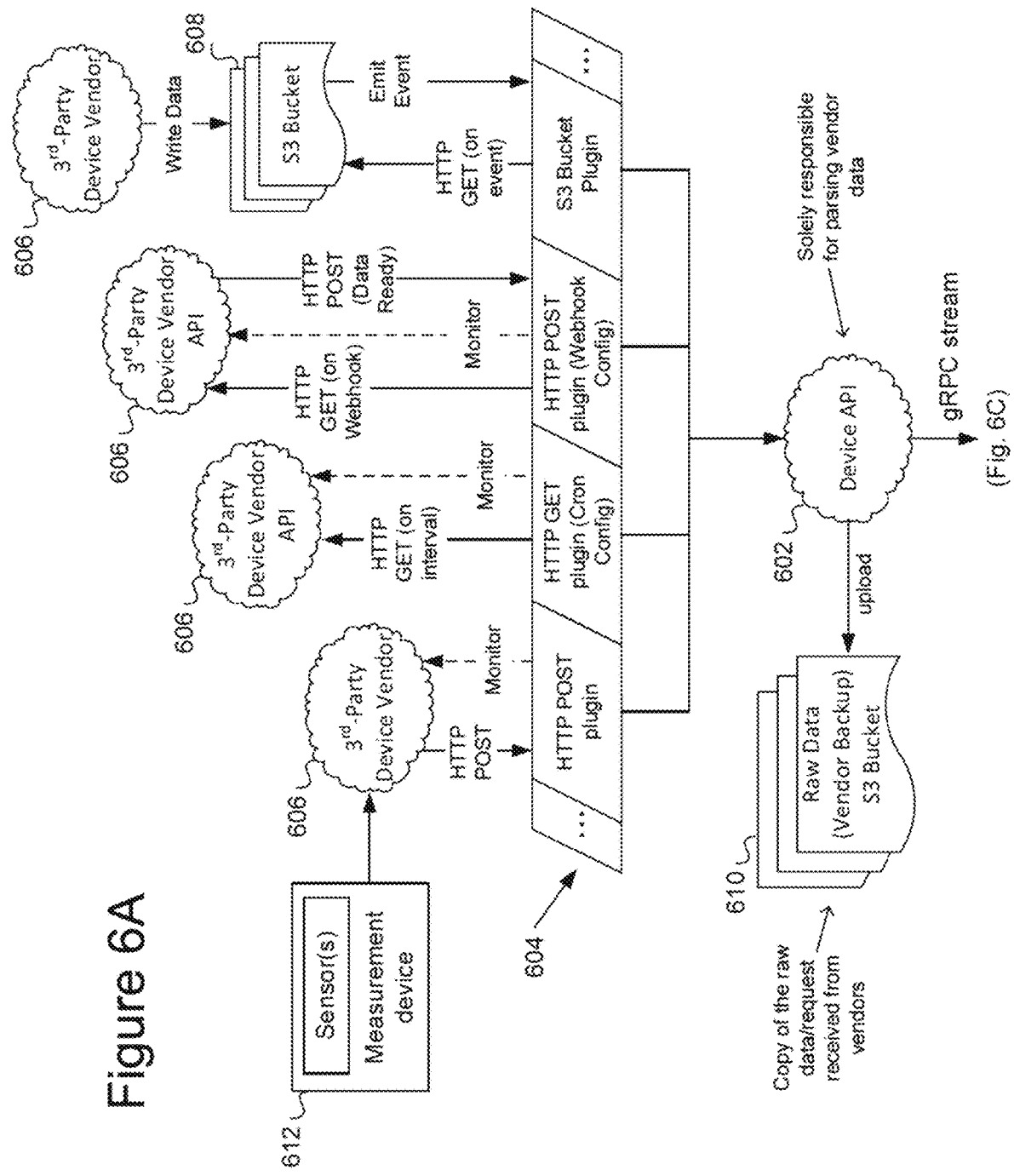
FIGS. 6A-6C illustrate a data ingestion architecture of the system.
Figure 6B:
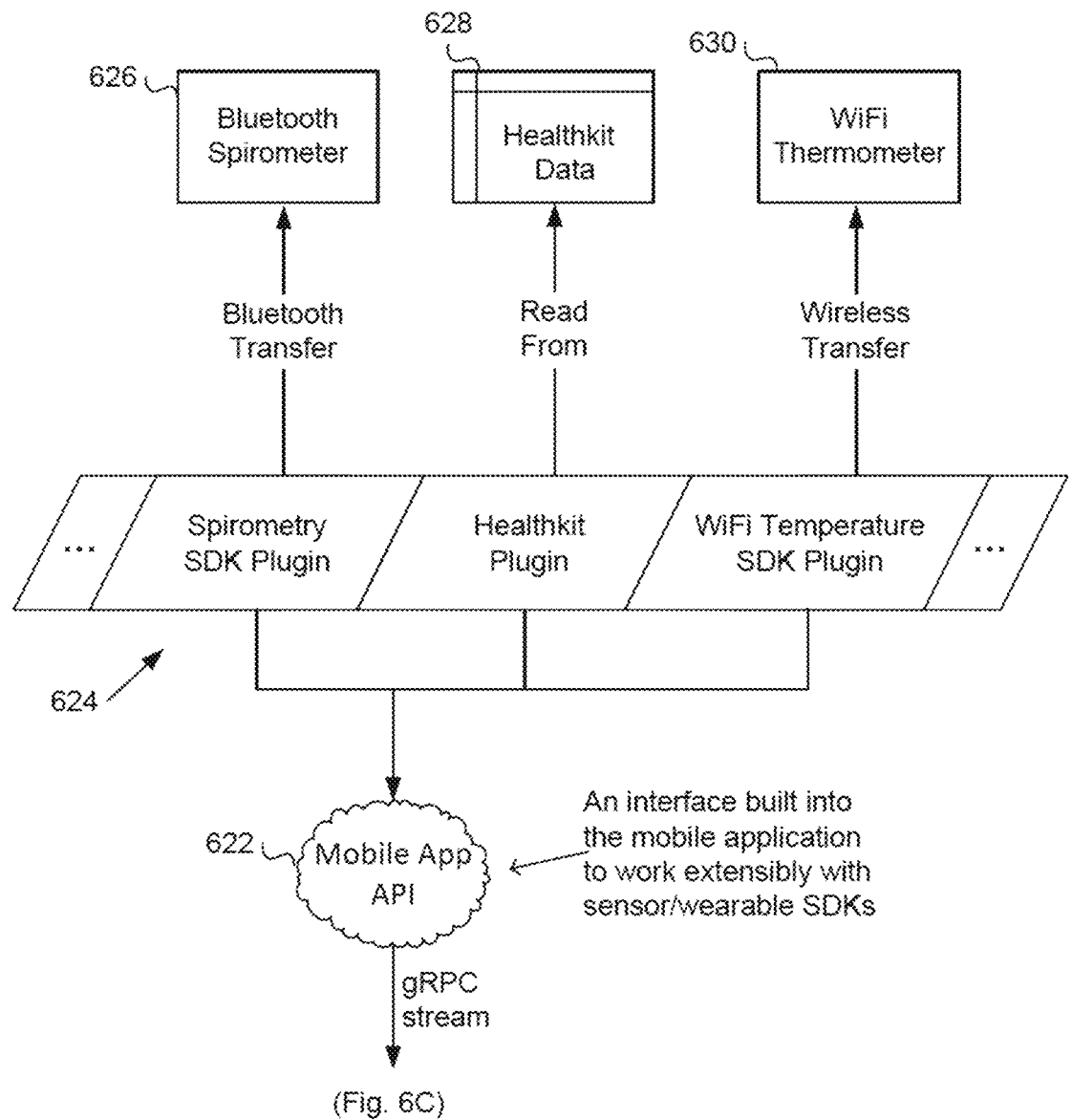
Figure 6C:
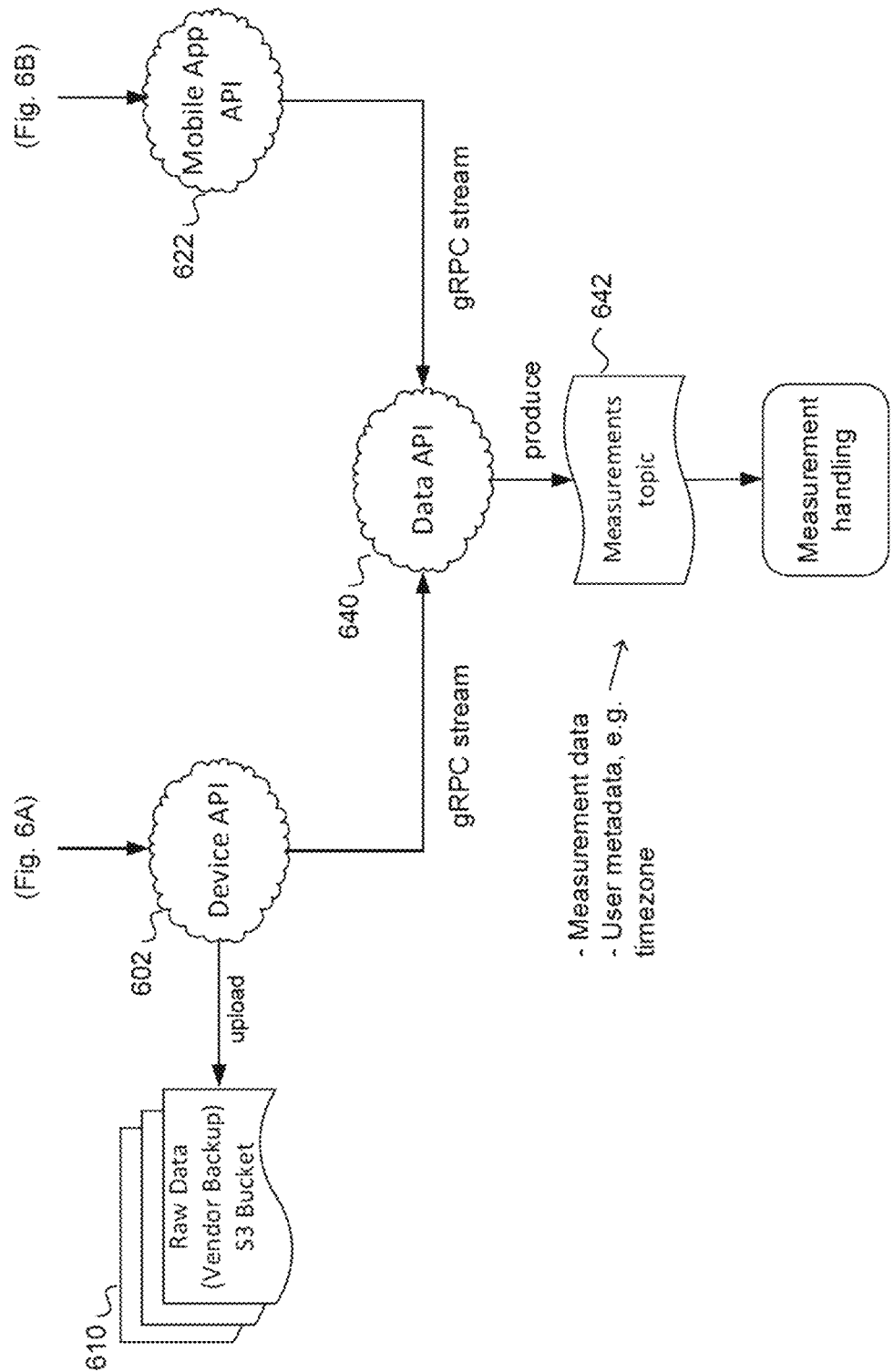

The data ingestion pipeline is illustrated in FIGS. 6A-6C and includes the following subsystems:
- A device interface for interfacing with device vendor APIs for standalone external sensor devices (FIG. 6A)
- A mobile application interface forming part of the mobile application (106), for interfacing with sensors and associated subsystems of the user device and with external sensor devices connected to the user device (FIG. 6B)
- A unified data ingestion interface that interfaces with the device interface and the mobile application interface to receive measurements, and process, store and/or forward the measurement data as needed. (FIG. 6C)

These subsystems are described in the following sections.

Device Interface

The device interface is provided in the form of a web-based modular API and a set of associated interface modules in the form of plugins that communicate with third party device vendor APIs to collect data from standalone sensor devices, based on the study configuration. When a study begins, the system identifies the required standalone sensor devices, and creates data channels for each using existing plugins or by attaching the required new plugins to the device API if they do not already exist.

Each active plugin for a study will be configured to retrieve data in a particular way. When creating a study, it is possible to provide any custom plugin (with some pre-defined interfaces, such as method of transport, method of backfill, relevant URLs, etc.)

FIG. 6A illustrates the device interface in the context of some example plugins and their configurations.

The device API 602 includes (or communicates with) an extensible set of plugins 604 which are responsible for bringing raw measurement data into the device interface. The data originates from standalone sensor devices, typically via a third-party service (e.g. provided by a device vendor). In this example, a standalone sensor device 612 is illustrated that provides sensor data to a device vendor system 606. For example, a standalone device could be a wrist-worn fitness monitor or smartwatch, and uploads data such as accelerometer data, step count data, pulse measurements etc. to a remote data collection system of the device vendor. Different vendors provide respective data collection systems 606, each with their own APIs for accessing collected data.

The relevant plugins 604 interface with the device vendor APIs to retrieve the measurement data. Each plugin is specifically adapted to a particular service to retrieve data using the appropriate transport mechanisms, query formats, data formats etc. Some examples include the use of common tools such as the Amazon Simple Storage Service 'S3' (608) and transport methods such as HTTP (Hypertext Transfer Protocol), e.g. using HTTP POST or HTTP GET queries, and RPC (Remote Procedure Call) mechanisms such as gRPC. However, these can be interchanged with any similar tool/transport method.

The plugins receive data from the respective device vendor systems/APIs and provide the raw sensor data to the device API 602. As mentioned previously, "raw" data generally refers to the data as received from the device vendor systems. As such the "raw" data may or may not have been pre-processed by those systems, e.g. raw data may correspond to raw sensor data as generated by sensors, or to the data as processed and made available by the device vendor systems (e.g. having been converted, formatted, aggregated etc.) A copy of the raw data received by the device API 602 is uploaded to a backup system or database 610 (in this case an S3 bucket, but any suitable storage technology may be used).

In addition to receipt and initial processing of sensor data, part of the device API's configuration revolves around the monitoring and alerting of external systems' uptime. Because it relies on third party device-vendor APIs in many cases, it makes use of a configurable monitoring engine for each plugin to ensure that the external APIs are monitored and that the system throws appropriate alerts if one of these APIs goes down and the system is unable to retrieve data for some time. A backfill method is preferably defined for each plugin which is defined to run when the system comes back online to fetch missing data and complete the measurement data records.

Mobile Application Interface

The mobile application interface is illustrated in FIG. 6B. It fulfils a similar role as the device interface described above, but for sensor data obtained directly by the mobile application at the user device.

The mobile application interface includes a mobile application API 622 which forms part of the mobile application 106 on user device (e.g. smartphone) 104 (see FIG. 1), together with a set of interface modules in the form of plugins 624. The mobile application API 622 provides a mobile modular interface within the mobile application that communicates, via the plugins, with internal device sensors of the user device and with sensor devices directly connected to the user device via Bluetooth, Wi-Fi, NFC, or other local wireless or wired connections to gather sensor data and send it to the central system for processing. Like the device interface of FIG. 6A, the mobile application interface is modular in design, and is extensible via the set of plugins 624 to communicate with different sensors and user device subsystems. Each plugin may be associated with a different device type and/or with different data transport mechanisms and/or device interfaces.

The present example shows a Bluetooth connected spirometer 626, with a plugin 624 for accessing spirometry data via an API/SDK (software development kit) provided by the spirometer vendor. A Healthkit plugin is shown for accessing data 628 from Apple's health application provided on Apple smart devices (that data may originate from sensors integrated into the user device or from external sensors). As a further example, a plugin is shown for a Wi-Fi thermometer 630. Other plugins may be provided to support internal sensors, e.g. accelerometers. The specific plugins/devices are shown purely by way of example. The system can be configured with plugins for obtaining data from any suitable external sensor device connected to the user device, internal sensor of the device, or other internal subsystem (e.g. a health or sensor API or application) of the user device. Thus, data may be supplied directly from sensors or indirectly via other (e.g. third-party) applications, APIs and subsystems, via the relevant plugins, to the mobile application API 622.

The system is modular and extensible. Existing plugins may be configured or new plugins added to interface with new devices and subsystems (e.g. APIs, SDKs) to generate a data ingestion pipeline for a particular sensor device or data source.

In an embodiment, data ingested via the mobile application API is supplied into the common measurement model that is used throughout the mobile application for all data collection tasks including questionnaires, interactive assessments, the use of mobile sensors, and external device sensors. Sensor data and other data obtained via the mobile application API 622 is sent to the central study management system through a mobile gateway and is then processed further into the Common Measurement Model as discussed in more detail above.

FIG. 6C illustrates unification of the device API 602 and the mobile application API 622 through a shared data ingestion API 640. The data ingestion API (and subsequent data processing pipeline) is implemented at the central study management system and receives sensor data from standalone sensor devices from device API 602 (which could be implemented at the central system or a separate data collection system) and from the mobile application (and hence from sensors of the user device or other sensor devices directly connected to the user device) via mobile application API 622. The data ingestion API also receives data generated directly by the mobile application itself (without use of internal device sensors or external sensors), for example based on direct user input (e.g. health questionnaires) or interactive assessments performed by the application. Based on the received data the data ingestion API generates measurement events and publishes those measurement events to an event handling subsystem under a measurements topic 642 (where a topic identifies a particular event type that events can be published against and to which event consumers can subscribe). The measurement events are then processed by subsequent pipeline components as described in more detail below.

However, while example embodiments use an event-based model for communicating measurements, other suitable communication approaches may be employed to implement the pipeline. For example, the data ingestion API may store sensor data in a relational database where it can subsequently be retrieved by other components of the processing pipeline.

After receipt of sensor data by the data ingestion API and storage of the raw sensor data and other data, the next step in the measurement processing pipeline is the conversion of raw sensor data and other data into the common measurement model (described above). Alternatively, the sensor data and other data could be converted into the common measurement model by the device API 602 and mobile application API 622 or their respective plugins.

After conversion into the common measurement model, data aggregation is performed. The term "aggregation" is used here to denote any processing of raw sensor data and other data to determine one or more derived measures; since typically a derived measure is computed from multiple raw sensor readings (e.g. as in the case of step counts computed from accelerometer data) this stage is referred to as aggregation, though other forms of processing (e.g. unit conversions) could additionally or alternatively be performed at this stage of the process. The derived measures may comprise a set of health indicators relevant to the health study being conducted.

The aggregation pipeline is itself another modular service capable of handling different types of raw sensor data and other data, implementing different aggregation and other processing algorithms via an extensible set of plugins.

Figure 7:
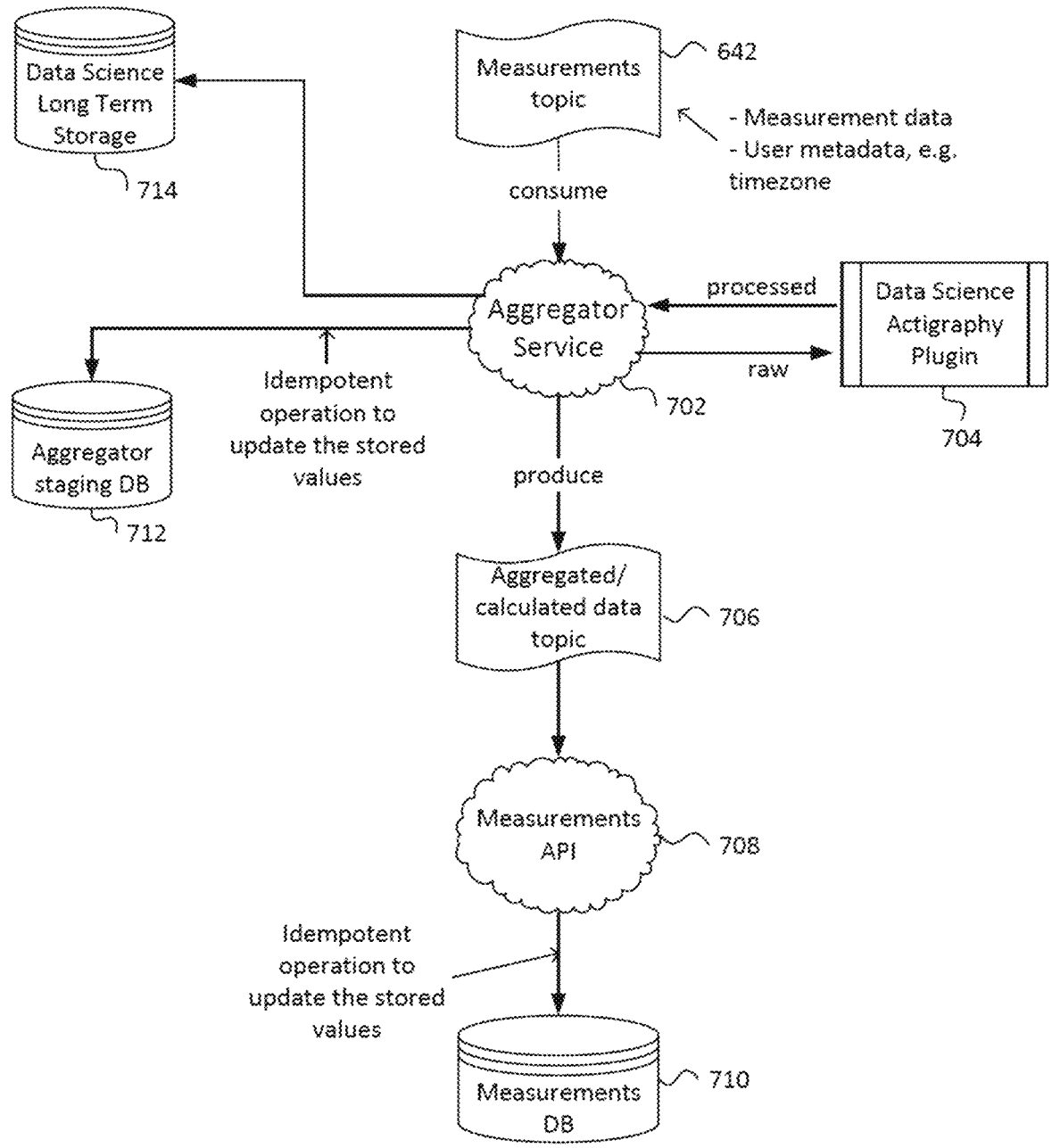
FIG. 7 illustrates a data processing pipeline.

The aggregation pipeline is illustrated further in FIG. 7 and includes an aggregator service 702 which consumes measurement events from the measurement topic 642 at the event handling system and generates new measurement events containing processed measurement data (e.g. aggregated and/or derived measurements obtained from the raw sensor data) which are submitted to the event processing system. The aggregator service employs a staging database 712 for temporary storage of data being processed. For example, it may be necessary to collect a (potentially large) set of raw sensor readings (e.g. accelerometer readings) before derived/aggregated data (e.g. step count) can be computed and the necessary data may be collected in the staging database. Additionally, raw and/or aggregated/processed data may be written to a separate database 714 for long term storage, e.g. for use by external data science applications.

Processing of measurement data by the aggregator service 702 is modular and configurable via plugins. In this example, a data science actigraphy plugin 704 is shown to derive actigraphy measurements, e.g. sleep duration, sleep stage data etc., from raw sensor data (e.g. accelerometer data). However, depending on sensors and the measurements of interest, any suitable aggregation and processing algorithms may be implemented in the aggregation phase via suitable plugins to obtain the aggregated or derived measurements. The aggregated/derived data is fed by the plugins back to the aggregator service which may store the measurements (e.g. in databases 712/714) and which generates and submits aggregated measurement events to the event system under an aggregated measurement topic 706.

The aggregated measurement events are received by a measurement API 708 and stored in a measurement database 710. From there, study datasets may be compiled and exported for use by researchers as previously described.

The event-based processing pipeline may also allow multiple processing/aggregation plugins to be chained (with one plugin processing the output of previous plugin).

A data aggregation plugin such as the actigraphy plugin 704 of FIG. 7 is a data processing module that is triggered by receipt of a specific measurement type at the aggregator service 702, and converts the raw sensor data for that measurement type into the derived/aggregated measurements specified using the common measurement model, using a particular aggregation/processing algorithm. Different plugins can be provided to support different measurement types simultaneously, for many different studies, study participants and devices.

Figure 8:
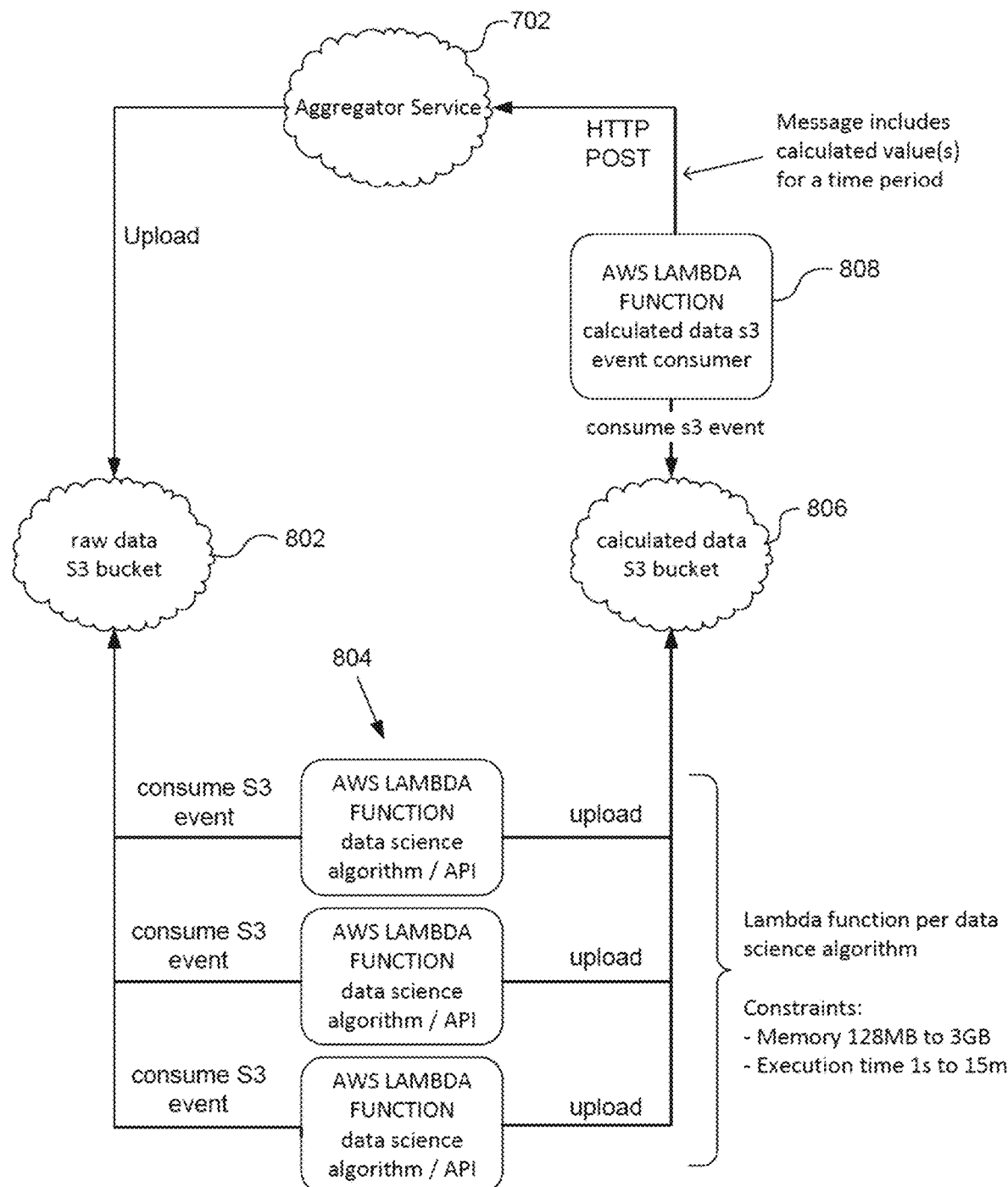
FIG. 8 illustrates operation of a data processing plugin.

One example plugin is shown in FIG. 8 for calculating steps, wear coverage, and sleep data from raw actigraphy data.

In this example, the plugin is implemented as a set of AWS (Amazon Web Services) lambda functions using an S3 data store for data exchange. The aggregator service 702 uploads raw measurement data in the common measurement model format to an S3 bucket 802, generating S3 events that are consumed by a set of lambda functions 804. Each lambda function may be responsible for generating a specific type of derived/aggregated data from the raw data uploaded by the aggregator service. In the above-mentioned example, the three lambda functions 804 may be responsible for generating steps, wear coverage and sleep data respectively, from the raw actigraphy data, using a suitable algorithm. Each lambda function uploads its calculated results in the common measurement model format to another S3 bucket 806 for calculated data. This again generates S3 events that are consumed by a further lambda function 808 which transmits the derived data (in this case as a measurement including wear coverage, steps, and sleep duration values as shown in Example 3 above) back to the aggregator service 702 via an HTTP POST operation.

The described architecture allows new plugins for new data types and/or aggregation algorithms to be implemented and deployed easily and efficiently. However, other plugin architectures could be utilised. For example, while the use of specific cloud computing architecture is described for implementation of the plugins (e.g. S3 object store for data exchange, AWS lambda functions for data processing, and HTTP for transmission) other storage, processing and transmission technologies may be substituted.

The system can be extended to support other types of data sources and transports, for example e-mail. For example, a batch of sensor data readings could be attached as a file to an email transmitted to a predetermined address associated with the study management system, which extracts the data (e.g. using a suitable plugin in the described architecture) and ingests the data into the processing pipeline.

The data ingestion pipeline may be implemented by multiple server devices, with load balancing implemented to direct sensor data to available servers and prevent particular servers from being overloaded.

The processing pipeline may also be extended to incorporate reporting functionality, for example to automatically extract relevant data from the measurement database and place the information into a standard uniform report format.

Figure 9A:
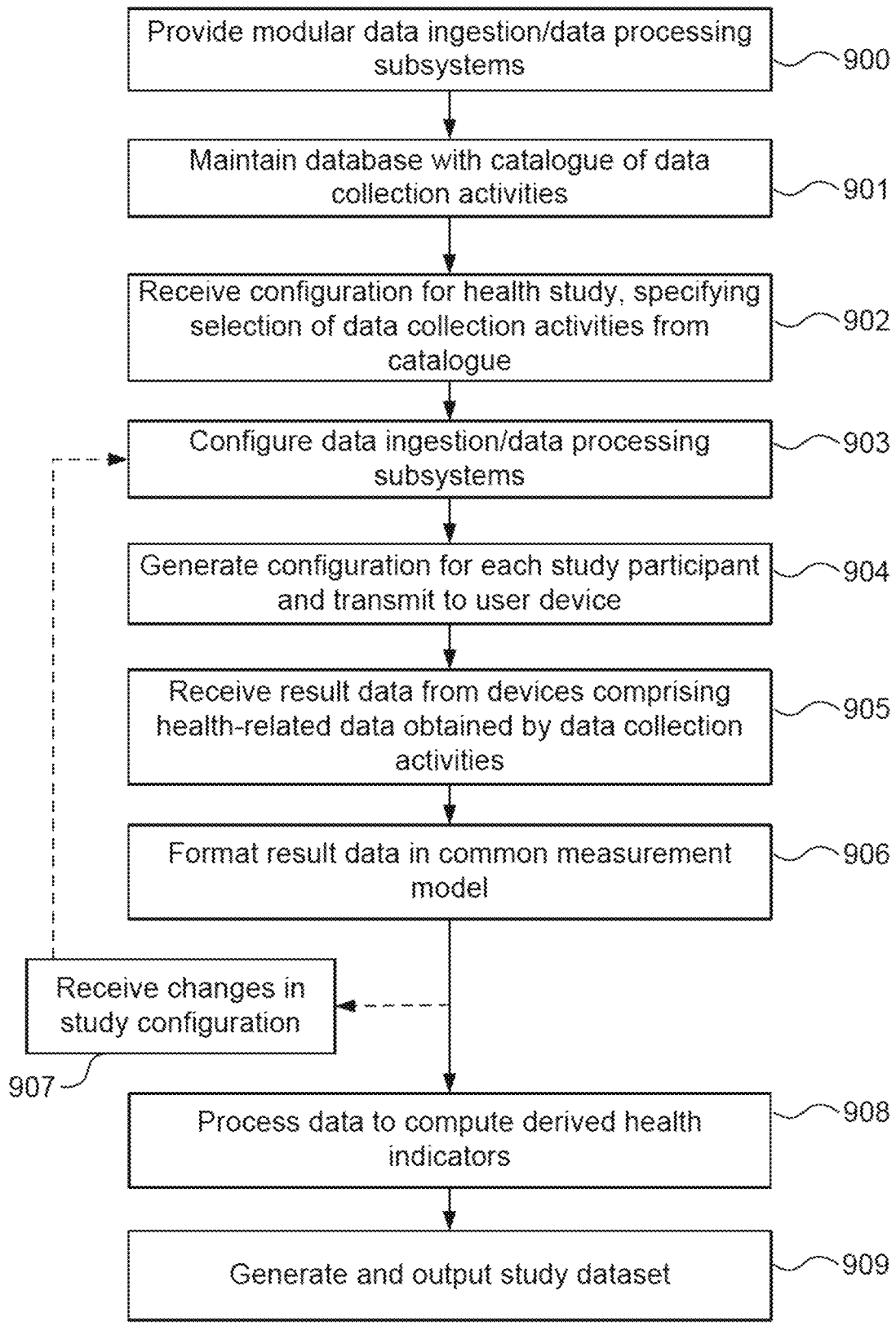
FIG. 9A illustrates server-side configuration and processing for a particular health study.

The central configuration and subsequent operation for collecting and processing data at the central health study management system are further illustrated in FIG. 9A.

Configuration is based on provision of the modular data ingestion subsystem and modular data processing subsystem described above (step 900). Additionally, a database is maintained storing a catalogue of data collection activities (901). This includes task definitions (discussed further below) defining data collection activities which may be performed at user devices, including the various types discussed above, such as sensor-based activities, data input activities and interactive assessments.

Configuration starts in step 902, where a configuration for a health study to be carried out is received. This may have been created by a study researcher using the configuration dashboard interfaces as discussed above. The configuration defines the practical implementation of a particular health study protocol using the present system. In particular, the configuration specifies the set of data collection activities to be performed as part of the study, which may be predefined data collection activities selected from the catalogue. Bespoke data collection activities may alternatively or additionally be defined for a particular study. The data collection activities may correspond to the assignments or assignment tasks discussed elsewhere herein (e.g. an assignment may include a single data collection activity or may comprise multiple data collection activities as sub-tasks). Each data collection activity is designed to collect respective health-related data for the study, where health-related data may include any health-relevant information, including data indicative of user health and raw source data (e.g. user input, sensor data etc.) from which data indicative of user health can be derived.

The health study configuration can also specify additional information about the study implementation, for example scheduling information defining the scheduling of the data collection activities, study participants, required user device characteristics (e.g. technical capabilities required), sensor devices etc.

In step 903, the data ingestion and data processing subsystems are configured based on the health study configuration (including the task definitions obtained from the catalogue), by selecting the relevant server-side data ingestion and/or data processing plugins required to ingest and process the health-related data for the specified data collection activities from the relevant data sources (e.g. sensors, direct input or interactive assessment). The configuration step serves to configure data flows for data collection activities using an appropriate set of interface plugins and/or processing plugins to enable ingestion and processing of the result data received from the user devices.

In particular, this step may configure, for a data source associated with a data collection activity (e.g. a particular sensor), a particular interface plugin of the data ingestion subsystem to receive health-related data from the given source and/or a particular processing plugin of the processing subsystem to process health-related data from that source. For example, for a data collection activity involving a walk test, an interface plugin may be configured to receive accelerometer data from the user device and a processing plugin may be configured to process the accelerometer data to compute gait and balance. Note that the central system performs selection/configuration of any server-side ingestion and processing plugins. Additional configuration may be performed at the user device, e.g. to configure specific sensor plugins that run at the user device.

In step 904, a data collection configuration is generated for each user device associated with a study participant. The data collection configuration may be common to multiple user devices/participants, or in some cases separate configurations may be generated for different devices/participants. The data collection configuration specifies the data collection activities to be performed at a device (using the task definitions obtained from the catalogue), the schedule (e.g. target times) for the data collection activities (as discussed in more detail below), and other related information, such as instructions for the user on how to carry out particular tasks or assessments. The configuration may be tailored based on user or device-specific criteria, for example a language configured for a particular user device/participant (e.g. by selecting instructional information, input forms, interactive assessments etc. in the required language).

In step 905, the system receives result data from some or all of the user devices. The result data includes the health-related data collected by the data collection activities and is ingested via the configured data ingestion subsystem, e.g. using particular selected plugins for the sensor devices and other sources being employed. The received data is converted or reformatted into the common measurement model in step 906.

In step 908, the received data is processed using the configured processing subsystem (e.g. including the particular selected processing plugins) to perform aggregation of data or other calculations of derived measures. The derived measures include a set of derived health indicators relevant to the study, for example relating to particular health metrics and health outcomes being studied. A derived health indicator may be based on data from a single source (e.g. a particular sensor) or may combine information from multiple sources/data collection activities.

In step 909, a study dataset is generated based on the result data and/or any associated derived measures and health indicators obtained from the user devices, and is output e.g. for storage, transmission to researchers, further analysis etc.

In some cases, the health study configuration may change while a study is ongoing, for example to reflect a change in study protocol design. Such changes could include changing the data collection activities that are performed (e.g. to drop, add or substitute one or more data collection activities), modifying the specific data being collected by one or more data collection activities (e.g. changing the format of a questionnaire), modifying the scheduling of data collection activities (e.g. times and/or frequencies at which these are performed), or changing the server-side processing (e.g. to add, change, or remove derived health indicators that are computed from the result data or change processing algorithms that are applied). If this occurs, then the system receives the changes in study configuration in step 907, and reconfigures the data ingestion/processing subsystems as needed (step 903) and/or generates updated data collection configurations which are sent to one or more of the user devices as needed (step 904). After reconfiguration, the system continues to receive and format result data (905, 906), and computation of derived measures/health indicators and the generation of the study dataset (steps 908, 909) may be based on result data received both before and after reconfiguration, allowing the study design to be adapted while the study is ongoing.

The study management system may support multiple concurrent health studies. The above process may thus be repeated to configure the server-side architecture and a respective population of user devices for each of multiple health studies, and to operate data collection and processing for those studies concurrently.

In order to support an extensive list of measurements, device integrations, and other assignments, a uniform 'Task Definition' model is used to define data collection activities that may be performed at a user device. This model configures sensor readings, assignment-level decision making, compliance thresholds, assignment time, and how the user can interact with the assignment, and works in the same way regardless of the specific type of user device being employed.

The task definition model comprises a data structure for representing an assignment task (e.g. a specific data collection activity) including an 'options' field where various configuration values are stored, a task identifier, referenced to external files (e.g. as URLs/URIs) that are required to run the task or provide guidance to the user in completing the task, and information needed to run the task itself, for example:

- definition of the sensor(s) to be used for sensor-based tasks (or the data to be collected for other types of tasks);
- definition of user interface screens to be displayed to the user as sensor readings progress;
- definition of the input values to be obtained for tasks involving direct input of health data values (e.g. in a questionnaire), e.g. by defining user input forms/fields and associated user prompts;
- definition of interactive assessments to be run at the user device.

The data collection activities are specified in the configuration package generated by the central system and communicated to the user devices as task definitions using the above task model. In preferred embodiments, all task definitions are device agnostic. For predefined tasks in the catalogue, task definitions are preferably also stored in the catalogue in this format. After selection from the catalogue, the configuration may be generated directly from the task definition or the task definition may be customized by the researcher if needed.

Configuration and Scheduling at the Mobile Application

The mobile application is highly configurable to support different studies and can ingest the specialized configuration package provided by the central system to generate an ongoing flow of scheduled assignments, sensor readings, and notifications.

In addition to instructing the mobile device on how to run assignments via task definitions, the configuration also specifies scheduling information which is interpreted by a scheduling engine of the application to dynamically schedule assignments in an event-based manner, where sensor readings, user-specific medical conditions, and external events can change the flow of the assignments. While one approach to this problem might be to just send all possibilities to the client and offload all of the processing to the mobile application, such an approach can be problematic due to limitations in bandwidth and processing capabilities of the user devices. Preferred embodiments address these and other technical challenges, such as:

- Any smartphone or other user device running the mobile application should preferably be able to process any schedule for any user to run any assignment. The entire system is preferably fully configurable.
- As the mobile application is configurable to work with any study configuration and can dynamically make tasks available to users, the configuration should preferably contain all information on dynamic scheduling based on assignment results, information on decisions that must be made based on user input, sensor data, or user conditions and how those decisions should be made. In addition, the mobile application can ingest study protocol parameters to determine whether or not the results of a particular assignments are compliant.
- The configuration is preferably updateable remotely by study coordinators, and the user device is preferably able to remotely retrieve and ingest new or modified protocol parameters within a relatively short period, e.g. a day.
- However, it is desirable to be able to serve low-bandwidth, low-connectivity regions. Therefore, the complex configuration preferably meets strict size requirements and can be compressed to a relatively small configuration package, e.g. in a preferred implementation the size of the configuration package is no more than 5 kB.

Near real-time remote monitoring of assignments can be desirable to ensure protocol compliance and support successful clinical studies. Therefore, the application preferably generates a comprehensive audit trail explaining all decisions made by the application, all missed and completed assignments, and user actions which is transmitted to the central study management system for monitoring. The transmission of this audit trail is again constrained to strict size requirements to serve low-bandwidth, low-connectivity regions.

All assignments are preferably scheduled in a time zone agnostic manner, as they are constrained by external events such as medication time. This can cause complications when representing timings using standard date/time formats such as the ISO 8601 standard for storing and manipulating dates. Preferred embodiments therefore use an alternative format for defining timings, to allow generation of dynamic dates such that if the user is changing time zone or changing their daily routine, the client contains an instruction set that describes how to handle these changing behaviours.

The proposed solution allows efficient and configurable management of how and when assignments run whilst also enabling the generation of an audit trail. Meeting the complex logical demands in a low-bandwidth environment is achieved by creating a virtual and dynamic assignment schedule. The schedule is specified by schedule data in the configuration package and is parsed by a schedule parser to generate any configurable set of assignments and associated data collection activities.

Figure 9B:
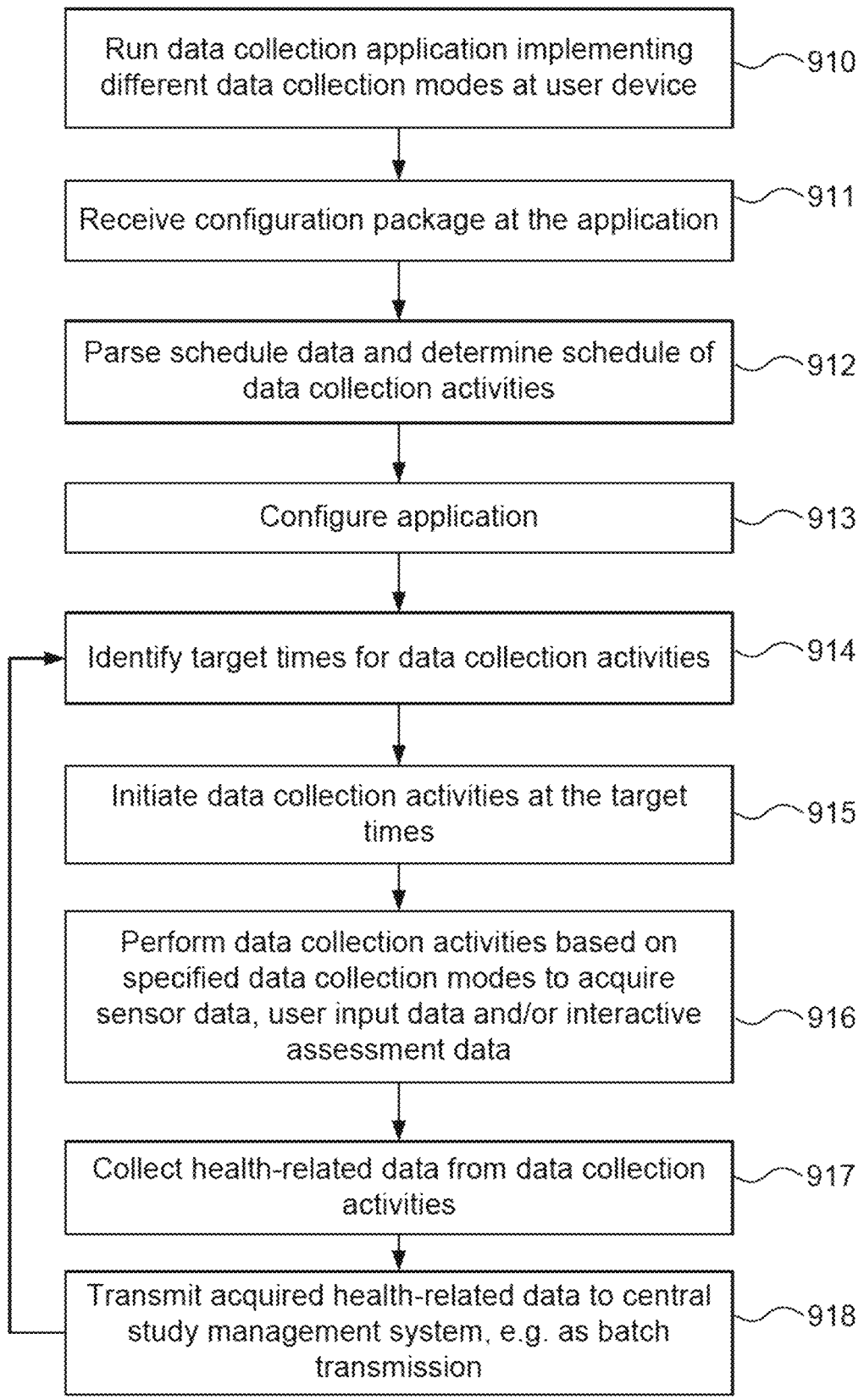
FIGS. 9B-9C illustrate client-side configuration and processing for a health study, including scheduling of data collection activities at a mobile application on a user device.

Configuration and subsequent operation of the mobile application is illustrated in FIG. 9B.

In step 910, the mobile application is run at the user device. The application provides data collection functionality in accordance with several different data collection modes corresponding to the different types of data collection activities, including sensor-based data collection, data collection through direct user input, and running interactive assessments.

In step 911, a configuration data package including task definitions and schedule data is received at the mobile application from the central study management system. The schedule data defines a schedule of data collection activities to be performed at the user device. Data collection activities may include any type of task (as defined in the task definitions) forming part of an assignment, including passive sensor data measurements or tasks where the user is instructed to perform an activity (e.g. walking) and sensor data is obtained during the activity. Data collection activities may also include requesting and acquiring user input, e.g. for a symptom questionnaire or the like, and running interactive assessments, as described above.

In step 912, the schedule data is parsed and a schedule of data collection activities is determined. In step 913, the mobile application is configured based on the specified set of data collection activities and schedule data. Note that target times for data collection activities may be fully specified in absolute terms or in a form that can be resolved at the time scheduling is originally performed. However, as described later, the system also supports dynamically resolved schedule timings, whereby target times for data collection activities (and other actions such as notifications or data uploads) are expressed relative to the occurrence of specific events, with the actual target time for an action only determined once the event has been detected. Thus, for such data collection activities, the initially generated schedule includes unresolved, dynamically determined target times (in the form of event-based timestamps as discussed in more detail below) that will be resolved to concrete timings at some later point.

After scheduling, the data collection application performs the data collection activities in accordance with the determined schedule. This involves, for each scheduled data collection activity, identifying (step 914) based on the schedule data a target time at which the given data collection activity is to be performed (this could have been determined at the scheduling stage, but for any dynamic event-based timestamps this occurs once the timestamp has been resolved, e.g. in response to the triggering event for the timestamp being detected), and identifying the relevant data source from which data is to be acquired (e.g. a sensor for a sensor-based data collection activity).

In step 915, the data collection activities are initiated at the relevant target times, and the data collection activities are then performed in step 916, based on the specified data collection modes, to acquire health-related data. For example, for a sensor-based data collection activity, sensor data is obtained from the identified sensor during performance of the data collection activity. This step may involve providing instructions to a user to perform an action (e.g. complete a walk test, use an external sensor device such as a spirometer etc.), and the sensor data obtained may include a single reading from a single sensor (e.g. a temperature measurement), multiple readings from a single sensor (e.g. multiple accelerometer readings over a specified time period), or one or more readings from each of a set of multiple different sensors. For direct data input activities (e.g. a symptom questionnaire), the application displays an input form as specified in the configuration and obtains user input for a set of specified health-related data values. For interactive assignments, the assignment is run by the mobile application and user interactions are recorded, and health-related data is derived from the detected user interactions (e.g. by measuring response times, response accuracy, or other suitable characteristics of the interactions as described above).

The health-related data generated by the data collection activities is collected and temporarily stored in a local database at the user device by the application in step 917. In step 918 the obtained health-related data is transmitted as result data to the central study management system. As described in more detail elsewhere, this may involve transmitting data from multiple data collection activities in a batch transmission and/or performing transmission at a scheduled time (which may be scheduled based on dynamic event-based timestamps) or based on network connectivity. Alternatively, result data from a data collection activity may be transmitted as soon as it is available, in near real-time. Optionally, some client-side pre-processing may be applied to the health-related data obtained by the data collection activities to obtain the result data that is transmitted.

Note that the steps of determining target times, initiating and running of data collection activities, and collecting and transmitting data (steps 914-918) may occur repeatedly over the duration of the health study. For example, a given data collection activity may be repeated periodically (e.g. weekly, daily or several times a day) as indicated in the schedule data. If batch transmission is used, the transmission step may occur at a different frequency than the data collection activities (e.g. transmitting a batch of all results acquired over a day).

If, during the health study, updated configuration data is received from the study management system (e.g. following a change in study protocol as discussed above), then the mobile application updates the locally stored configuration and reconfigures the application accordingly (as per steps 911-913). The reconfiguration may modify the data collection activities performed, the associated schedule etc. Data collection then continues in accordance with the updated configuration.

Initiation of a data collection activity may take different forms depending on the type of activity. For example, in some cases, the data collection activity may be performed automatically by the user device at the determined target time, e.g. where no user interaction is needed. This may be the case for tasks involving passive sensor data acquisition without user involvement. For other activities, the user may be prompted at the user device at the determined target time to start the data collection activity, e.g. by way of a notification within the application or outside the application (e.g. a system level push notification). Selection of the notification may launch the application and/or the relevant data collection activity within the application. As a further example, the data collection activity may be made available at the determined target time for selection and initiation by the user via a menu displayed at the user device (e.g. the activity may be added to a menu of upcoming tasks in the application, or the status of the task may change from inactive to active and become selectable in the menu). In these cases, the initiation may thus occur at the scheduled time (via some form of user prompt) but further user interaction may be needed to start performing the data collection activity. Regardless of how it is initiated (whether fully automatically or under user control), once the data collection activity itself starts, any relevant instructions, user input forms, or interactive assessment screens are then displayed on the user device and the application captures the health-related data from the relevant source(s).

Event-Based Timestamps

As mentioned above, conventional timestamps such as ISO 8601 or Unix timestamps typically do not allow for dynamic scheduling. Embodiments thus use a different approach for specifying timing information for scheduling activities.

Timing information is specified based upon a time amount, a time unit, and one or more trigger events. These define an event-based timestamp. A reference time for the timestamp is determined by detection of an event matching the specified trigger event (or one of the specified events if multiple alternative trigger events are specified). The event time (e.g. a time of receipt or creation of the event, which could be specified by an event time stamp of the event) defines the reference time used for timestamp resolution. The target time for the time stamp is then resolved by adding the specified time amount (converted as needed to the required time base in accordance with the specified unit) to the reference time. That resolved target time is stored as part of the time stamp and can subsequently be referenced and used to initiate a scheduled data collection activity such as a particular assignment or assignment task, or to trigger a notification or other action. The following set outs an example data format for storing a dynamic, event-based timestamp:

TABLE 1

Event-Based Timestamp Schema

| Field | Type | Description |
| --- | --- | --- |
| amount | number | Number of time units to add to the reference time determined by the 'from' trigger. |
| unit | Enum string | Selected from an extensible list of units such as 'days', 'hours', 'minutes', 'milliseconds', etc. This can also be extended to programmatic units denoted by a specific character (such as '$day'). One example could be a unit that returns a specific day of the week (i.e. 0 $day -> Sunday of this week. 2 $day -> Tuesday of this week. 14 $day -> Sunday two weeks from now.) |
| from | string | An event name selected from an extensible list of event names and specifying an event that should trigger the resolution of the timestamp. Some examples could be 'takeMedication', 'midnight', 'assignmentComplete', or even study-specific event strings. Any assignment can publish an event with a given name, which would resolve any subscribing event timestamps waiting for that event name. |
| resolvedDate | Date \| null | If the event has resolved the date is set to the computed target time and can be referenced, otherwise this field is null. |

Resolution involves computing an absolute time value (e.g. as a conventional ISO 8601 timestamp or similar), by adding the time period specified by the 'amount' and 'unit' fields to the reference time (time the resolution was triggered, i.e. time the relevant trigger event was detected). For example, this may be computed as the reference time determined by detection of the trigger event specified in 'from', plus the time 'amount' multiplied by the time 'unit' resolved to some basic time increment e.g. milliseconds. The 'amount' and 'unit' fields thus together specify a relative time quantity (in other words, a delay period), relative to the triggering event, which is resolved on occurrence of the triggering event to an absolute time (resolved Date). The resolved time may be in the user device's local time or in a universal time format, e.g. UTC (Coordinated Universal Time).

The trigger event is preferably a specific named event selected from an extensible set of predefined events. The system supports a range of event types and sources, including, for example:

sensor events corresponding to a sensor measurement; a particular sensor event could indicate any measurement obtained from a particular sensor, or could indicate a measurement meeting a particular criterion, such as a predetermined sensor value threshold;

a user input event, for example defining receipt of a predetermined user input or activation of a particular command or menu option in the application (e.g. a user confirmation that the user has taken medication), a status event identifying a status or change in status of the user device or mobile application, for example identifying loss or restoration of network connectivity, a battery status etc; and a timing event; e.g. an event could be generated at the start of every day or week an event generated by the central study management system and communicated to the user device over the communications network (e.g. indicating a status or status change of the central system, a change in study configuration, a data quality issue detected during server-side processing of sensor data etc.)

Events may, where applicable, include additional data associated with the event (e.g. sensor data obtained from a sensor, a user input or device status information etc.)

In the context of clinical studies and other health monitoring activities, some concrete examples of event-based timestamps include '1 hour after taking medication', '35 minutes after <specific sensor reading threshold>', or '7 hours after midnight'.

The implementation of the timestamp resolution is non-trivial since events can originate from an extensible list of sources. For example, some events may involve active input such as user input or a sensor reading, whereas others are entirely passive, like a certain time passing without the mobile application being online. Events are preferably also tied to the study configuration to ensure only relevant events are processed; for example, a specific sensor reading event can only occur if that specific sensor is configured for use in the current configured study. To support these events, the system provides an event handling pipeline that can both actively and passively update the state of many different events.

A further challenge is determining when these timestamps should be evaluated. In preferred embodiments, it is possible for the same event to fire multiple times, and since passive events are supported, the system that ingests events is designed to be stateless. As a result, the timestamps are statically evaluated at any given time before or after the event fires. Future time stamps (for which the triggering event(s) have not yet occurred) are automatically deemed 'unresolved', which is a defined status that is tracked and managed until resolved.

These dynamically resolved, event-based timestamps are used for resolving assignment launch and due times, push and SMS notification scheduling, triggering individual data collection activities, such as taking sensor readings, and uploading sensor data from the mobile application to the study management system. However, the system could be expanded to allow the timestamps to be used to trigger any programmatic action.

For example, a given assignment is typically associated with an event-based timestamp specifying a launch time, i.e. a time when the assignment becomes "active" (available for completion by the user). Once the timestamp has been resolved and the resolved time occurs, the mobile application prompts the user that the assignment should now be carried out. An assignment can also receive a future 'complete by' timestamp and then is tracked accordingly. Once the time of the time stamp occurs, additional evaluations may be conducted and processed based on the status of the assignment (e.g. to note that the assignment is now overdue).

Figure 9C:
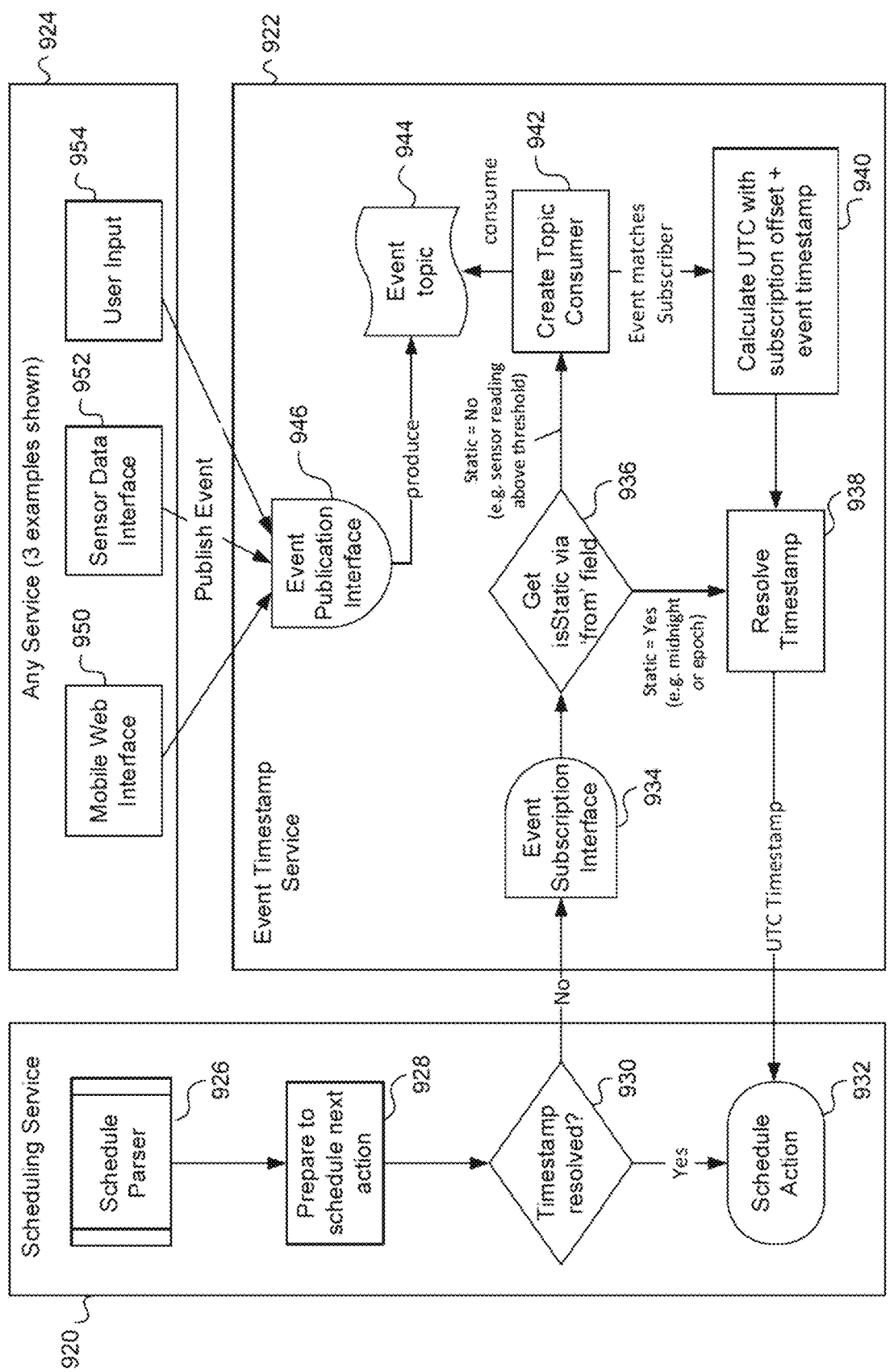

While designed to allow specification of dynamically resolved target times, the timestamps can also be used to specify static target times. For example, the target time could itself be specified in the resolvedDate field upon creation of the timestamp. In that case, the timestamp is effectively resolved on creation, without the need to dynamically resolve it later. As an additional example as noted above, special context variables or function calls may be specified in the 'unit' field to provide a time reference that is not event-based. The scheduling and timestamp resolution subsystem is illustrated in more detail in FIG. 9C. The subsystem includes a scheduling service 920 and an event timestamp service 922.

In addition, external services 924 generate various events that may trigger timestamp resolution. Here, a mobile-web interface 950, sensor data interface 952, and user input 954 are shown as possible event sources, but these are purely by way of example, and any subsystem or external system may in principle generate events, which are published to the event handling subsystem by sending an event notification or message to the event publication interface 946, which manages events associated with particular event topics 944. The event message identifies the event and may include any data content associated with the event (e.g. sensor data for a measurement event). Event consumers can subscribe to particular event topics at the event handling system. When an event is published to the event handling system for which there is a subscriber (e.g. a particular software component of the mobile application), the event handling system notifies the subscriber in an event notification or message corresponding to the received event message and identifying the event and including any data associated with the event. The subscriber can then process the event and associated data.

Note the event handling system included may be included in the mobile application or at the user device separately from the mobile application, and may be separate from the event handling system implemented at the central system (e.g. for controlling the data processing pipeline), or may be integrated into that central event handling system to allow events to be generated at the central system and consumed at the mobile application to trigger timestamp resolution. If not integrated, then a separate mechanism is preferably provided allowing events to be communicated to the mobile application from the central study management system.

The scheduling service 920 receives schedule data from the configuration package received at the mobile application, defining assignment and data collection activities for a particular study. Specifically, the schedule defines a set of assignments and associated data collection activities and user notifications, collectively referred to as actions, associated with respective event-based timestamps defining the times at which each particular action is to be performed (for example, a scheduled action may be an active assignment task such as a walk test during which sensor readings are collected, passive sensor data collection, a user questionnaire etc.) The schedule data is processed by the schedule parser 926. In step 928, the scheduling service prepares to schedule the next action (in practice steps 928-932 are repeated for each action specified in the schedule; for clarity processing of a single action is illustrated).

In step 930 the scheduling service determines whether the timestamp is already resolved (for example, the timestamp may simply be a static timestamp with an absolute resolved time specified at creation as discussed above). If so, the action is scheduled at the specified time in step 932. For example, the scheduling service may maintain a schedule table of actions to be performed with the resolved target times at which those actions are to be performed. The scheduling service then stores the action specified in the schedule and the resolved time of the timestamp in the table.

An execution service (not shown) monitors the schedule table and initiates the specified actions at the specified times. For example, for an action corresponding to an assignment task the system initiates the relevant task (e.g. prompting the user to perform a walk test and recording relevant sensor data). For a notification action, the system initiates a notification (e.g. by interfacing with a push notification service of the user device or with an SMS/email or other messaging service).

If in step 930 it is determined that the timestamp is not yet resolved, the timestamp is submitted to the event timestamp service for dynamic resolution, via event subscription interface 934. On receipt of an unresolved timestamp, the event timestamp service 922 first determines whether the timestamp is static (step 936). A static but unresolved timestamp is one where the resolved time is not event-dependent but can be computed from the information in the timestamp, e.g. from the 'amount' and 'unit' fields. As noted above, the 'unit' field may specify an absolute time unit such as milliseconds, or may provide a dynamically computable time reference. In the example given above, the unit may be '$day', where the '$' symbol denotes a computable time reference, e.g. as a reference to an external function or context variable, specifying the day of the current week, with the 'amount' field indicating the number of the day, such that (amount=2, unit='1 day') resolves to the Tuesday of the current week. Such timestamps are still resolved with reference to external functions or context variables, but are nevertheless static in the sense that they do not depend on occurrence of particular events. These events are resolved at time of scheduling and may e.g. be denoted by a special value in the 'from' field, e.g. 'isStatic'. Thus, if a static timestamp is identified in step 936, then the timestamp is resolved in step 938 by computing the absolute target time value as a UTC timestamp based on the information in the 'amount' and 'unit' fields. This is then returned to the scheduling service 920 to schedule the action in step 932 as previously described.

If the event is not static (step 936), this means the timestamp resolution is triggered by a particular event. The event is specified in the 'from' field. The event timestamp service therefore creates an event topic consumer in step 942 for the specified event (event topic 944). The event topic consumer is essentially a subscription to the specified event in the event handling system. At this point, assuming an event matching the trigger event has not already been published to the event handling system, resolution of the timestamp is incomplete, awaiting detection of the relevant event. Until the trigger event is detected, the timestamp remains unresolved (and thus any associated data collection activity or other action will not be scheduled).

As soon as the event publication interface 946 produces an event matching the event consumer created in step 942 (and thus matching the trigger event), the event consumer receives the event and triggers completion of the resolution of the timestamp in step 940. The reference time for resolution is determined by the time of the event. The system adds a time period as specified by the 'amount' and 'unit' fields (e.g. 2 days, 4000 ms, etc.) to the reference time to determine the resolved target time. This is stored in the 'resolvedDate' field of the timestamp, e.g. as a UTC timestamp. The resolved timestamp is then returned to the scheduling service, which updates the schedule to schedule the action associated with the timestamp (step 932) as previously described (e.g. by adding action and timestamp to a schedule table).

The timestamp resolution additionally accounts for daylight saving time (DST) when resolving timestamps. One particular situation that may arise is where the reference date is on one side of the changeover to or from DST, while the target date is on the other side of the DST changeover. For example, 11 hours after midnight on the day of the switch to DST should be 10 AM, not 11 AM as would be obtained by simply adding the time offset.

To address this, the system also obtains the DST offset from the reference date and target date, finds the difference between the two, and applies the difference such that the correct target time is obtained. If the offsets are the same, no correction is applied to the target time.

The described scheduling service and timestamp resolution system can be used in the scheduling of data collection activities, such as assignments and tasks, and to schedule notifications to the user.

Additionally, the scheduling service may be used to schedule data transmission. For example, instead of simply transmitting data to the server upon completion of assignments/tasks, the data may be collected at the user device and transmitted in a batch transmission at a scheduled time specified by a dynamic or static timestamp. This allows bandwidth utilisation to be optimised (e.g. transmitting results during non-peak hours).

Study Configuration Structure

In some embodiments, data collection activities are structured in the study configuration into virtual visits and assignments. A virtual visit (which provides a virtual analogue to e.g. a visit of a patient to a medical researcher, clinic or other medical practitioner for evaluation during a conventional study) may consist of one or more assignments. Each assignment in turn may be structured into one or more tasks, corresponding to different data collection activities. An assignment may thus define a particular workflow of tasks to be completed for the assignment. The schedule may also include configurations for notifications and for rescheduling of visits. These schedule components are described in more detail in the following sections.

The visit-level configuration provides instructions on which days to run assignments and collect sensor data. It is defined in terms of a recurring period that is defined by use of the event-based timestamps such as 'every 1 day' or 'every 2 weeks', start and end dates between which the period recurs, and a list of 'virtual visits' offset from the start or end of a period (i.e. 'on the 4th day of the period'). In this manner, the scheduling service of the mobile application can dynamically generate a large calendar of scheduled 'virtual visits' with only a small set of information.

The assignment-level configuration provides instructions on the flow of a given 'virtual visit'. It consists of assignment flows, which provide the configuration for a state-engine that runs the assignments for the day. Each assignment contains:

Separate 'launch' and 'due' event-based timestamps such as '45 minutes after the previous assignment is complete' which the mobile app uses to decide if an assignment is currently available (based on the 'launch' timestamp) or overdue (missed, based on the 'due' timestamp). The system supports at least the following approaches for processing those timestamps (configurable as part of the schedule):

Resolving these timestamps independently of one another, such that an assignment can be resolved to 'missed' via its 'due' timestamp even if its launch condition's precedent never occurred.

Resolving these timestamps in accordance with one another such that if an assignment's launch condition's precedent never occurs, the task is marked as N/A (not applicable) and it is not missed.

Conditions which are used to determine whether a particular assignment group, task or sensor reading is applicable to the current user based on user-specific conditions, such as medical history (e.g. presence/absence of a specific medical condition), or user device capabilities (e.g. availability of a specific integrated sensor or connected sensor device required for an assignment/task).

Compliance Metrics which set additional rules on how the assignments can be completed. Some examples could be a time limit that begins once the first assignment is started, or readings that would indicate that a user took or didn't take medication before an assignment when it is required.

A task list which links to the task definitions that should be available for completion within the launch-due window. For example, the tasks list could include a walk test and a symptom questionnaire.

Through the use of event-based timestamps and multiple condition types including conditions based on user input, sensor readings, and other factors, this system is able to dynamically create and update a schedule of assignments in real-time to ensure each patient's compliance with the study protocol applicable for that patient.

The notification-level configuration uses event-based time stamps to trigger sending of native push notifications to the mobile device. These are preferably fully event based and can be triggered by different conditions and events in the same way assignments and their data collection activities are triggered, via the event timestamp service.

In preferred embodiments, the application can schedule other types of notifications such as email or SMS in addition to (or instead of) local push notifications. If a particular schedule requests additional notification types, the application may attempt to schedule them via a Web API. From there, a web service will process the notification by type and will schedule it for sending. The application can unschedule these notifications via a different endpoint on the same API.

The rescheduling-level configuration uses event-based timestamps and a 'maximum times to reschedule' field in the schedule to reschedule an entire day's 'virtual visit' to some later date, while maintaining compliance with the parameters defined in the study protocol. All of the results are tracked from all instances, and a clear audit trail is generated to link all rescheduled sensor data back to the original 'virtual visit'.

The following pseudocode illustrates rescheduling of a virtual visit:

Task Results

Results from assignment tasks (i.e. data collection activities such as sensor measurements, user data input, interactive assignments etc.) are sent in a uniform wrapper, regardless of source device or sensor, that contains the 'Execution ID' which links the result back to the schedule it came from based on the following parameters:

Schedule ID
Visit Date
Assignment Index
Task Key
Times Rescheduled

These results, along with the schedule, can be used at any given time to determine what the user needs to do, what they have not yet done, and anything that is past due.

Figure 10A:
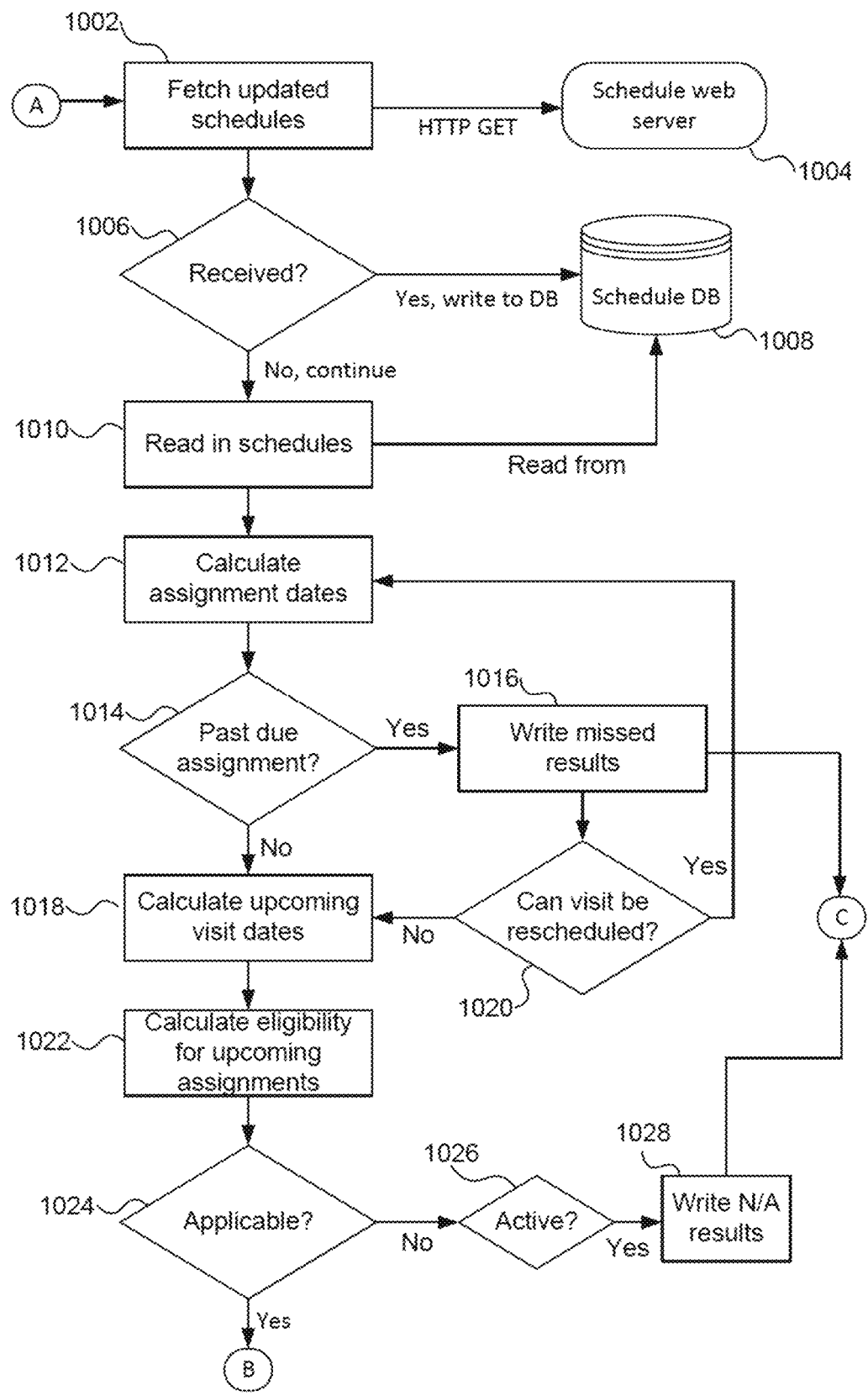
FIGS. 10A-10C illustrate further aspects of a scheduling process.
Figure 10B:
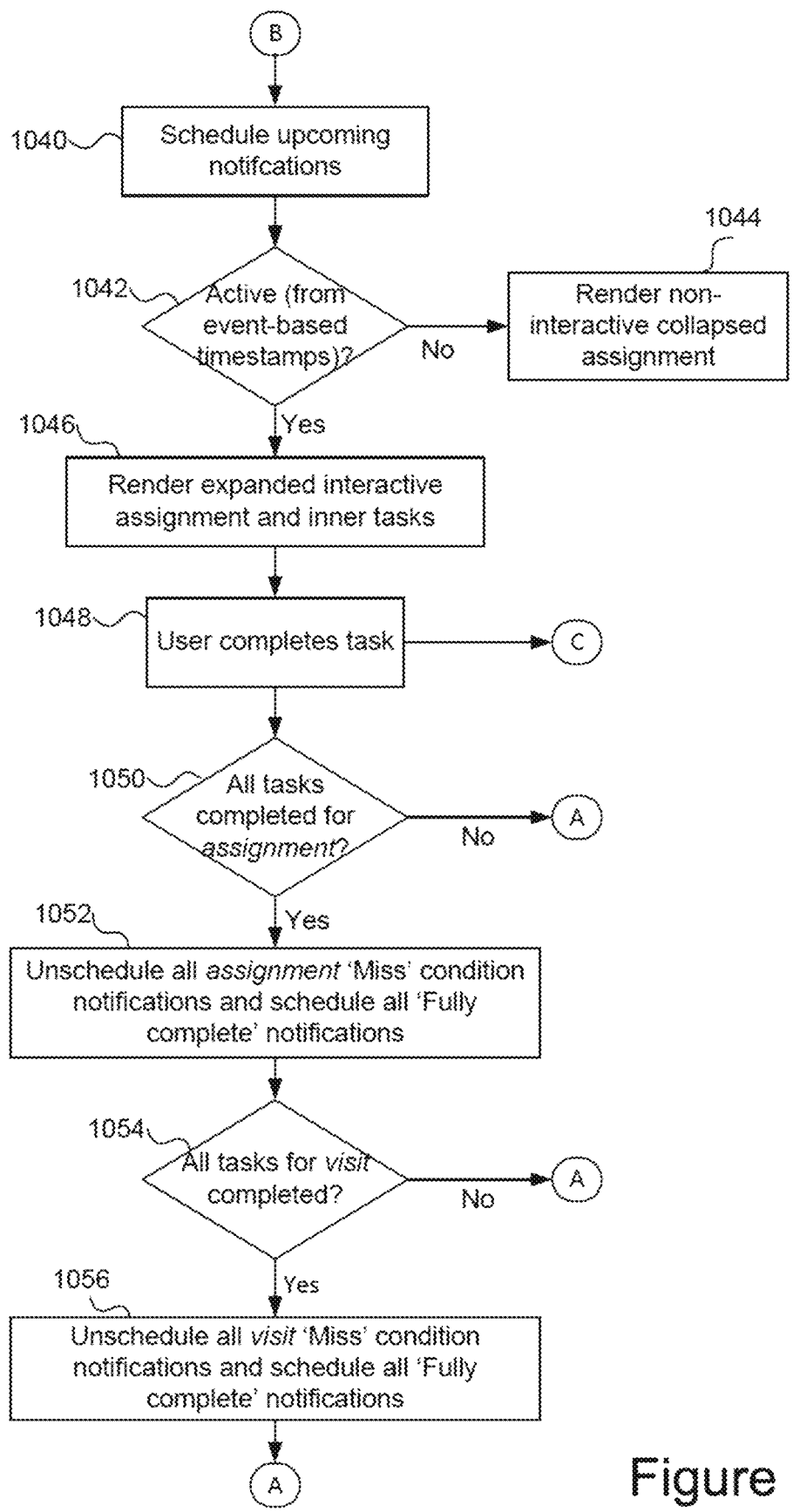
Figure 10C:
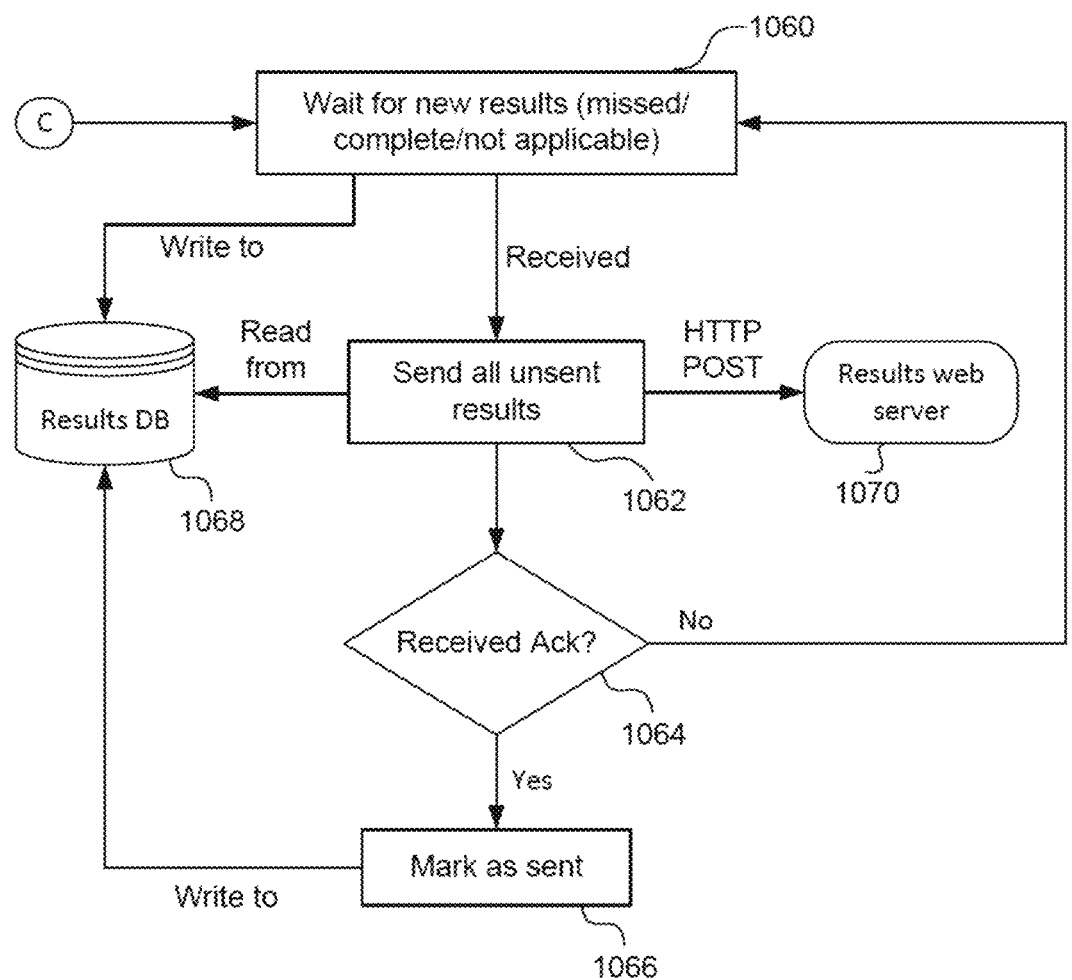

FIGS. 10A-10C illustrate the operation of the scheduling service running at the mobile application/user device in one embodiment in more detail, using the various different aspects of the configuration outlined above.

FIG. 10A shows calculation of visit and assignment dates. In step 1002, the scheduling service fetches updated schedules from the schedule web server 1004. If updated schedules are received (decision 1006), then these are stored locally in the schedule database 1008. These steps thus allow researchers to alter schedules during the study, with the local schedules at the user device being updated as needed. After the update, or if there are no updated schedules, the process continues to step 1010, where one or more schedules are read from the schedule database to schedule visits and assignments.

In step 1012, assignment dates are calculated from the schedule. This involves resolving any unresolved dynamic event-based timestamps using the event-based timestamp service as describe above. For example, the schedule may specify a dynamic event-based timestamp for a particular assignment (or assignment task), and the timestamp service provides the absolute UTC timestamp corresponding to the dynamic timestamp (once the trigger event has occurred), which is added to the schedule.

In step 1014, the scheduling service determines whether there are past due assignments (i.e. assignments that have not been completed and for which the due date has passed). If so, these are logged as missed results in step 1016. If the assignment is part of a scheduled visit, the scheduling service determines whether the visit can be rescheduled; if so, then the process returns to step 1012 to calculate new assignment dates. If not, then the assignment is simply marked as not completed and the process continues to step 1018. One or more notification(s) may also be scheduled (or

```
if (tasks.some((task) => task.missed)
    && visit.timesRescheduled < visit.rescheduleMeta.maxTimesReschedule
) {
  allVisits.push({
    ...visit,
    timesRescheduled: visit.timesRescheduled + 1;
    // return add amount, unit to original start date and end date
    start: resolveEventBasedTimestamp (visit.start, visit.rescheduleMeta.when),
    end: resolveEventBasedTimestamp
```

Example 4

As the pseudocode illustrates, the system tracks the number of times a visit has been rescheduled, and only allows rescheduling a limited number of times (that number being specific to the configuration).

generated immediately) to notify a user (e.g. patient and/or researcher) of a missed assignment.

Although in these examples, assignments are described as being part of visits (where a visit may include multiple assignments), it should be noted that assignments may occur without a visit. For example, some assignments may need to be completed by a user before a visit may occur (according to protocol requirements). Assignments may thus be scheduled (and if necessary re-scheduled) as part of a visit, or independently.

If there are no past due assignments (1014), the process continues to step 1018, to calculate upcoming visit dates for a predetermined period, e.g. over the next 30 days. In step 1022, eligibility of the user for upcoming assignments is determined. For example, this may involve determining:
- whether the user meets required characteristics for a particular assignment or task, for example the presence or absence of particular health conditions
- whether the user device meets required technical characteristics (e.g. availability of a sensor required for the assignment or task)

If an assignment is not applicable (1024) to the user based on the specified applicability criteria, but is currently active i.e. available for completion (launch date has passed, due date has not yet passed, check 1026) then a "not applicable" result is logged (step 1028).

It should be noted that, if an assignment scheduled in the future (not "active") is presently not applicable, it may still become applicable by the scheduled time, so in that case a "not applicable" result is not logged at this time. However, if an assignment is active (available) but is deemed not applicable, then the "not applicable" result is logged.

If the assignment is applicable to this user/user device then the process continues to step 1040 (FIG. 10B).

FIG. 10B illustrates further steps of the scheduling process. In step 1040, upcoming notifications are scheduled (e.g. push notification to the user to remind them when particular visits/assignments are due etc.) This again uses the timestamp service for resolving dynamic timestamps.

In the subsequent steps 1042-1048, scheduled assignments are executed based on their scheduled times.

In step 1042, the system determines if assignments are active (i.e. available for completion as defined above). Such assignments are displayed as selectable in the user interface where they can be expanded to display constituent tasks and the assignments/tasks can be activated by user selection to initiate them (step 1046). Non-active (i.e. future) assignments are displayed but cannot be interacted with (e.g. they are greyed out), but they are shown to give the participant a view of what they will have to do and when in the upcoming days (step 1044).

In step 1048 the user completes a task for an assignment. Results of the task (e.g. sensor measurements) are transmitted to the results service (illustrated in FIG. 10C and discussed below). In step 1050, the scheduling service determines whether all tasks for the assignment have been completed. If not, the process returns to step 1002 to continue scheduling and any new assignments/tasks and continue performing existing tasks for the current assignment, until the assignment is identified as completed.

If it is determined that all tasks for the assignment are complete, then notifications for the assignment are updated (1052), by unscheduling 'miss' notifications and scheduling notifications (e.g. to the patient and/or researcher) specifying that the assignment is complete.

In step 1054, the process determines whether all tasks for the visit have been completed. If not, the process repeats the scheduling and assignment loop as described above. If yes, then, similarly to step 1052, notifications are scheduled in step 1056, including unscheduling any notifications specifying a missed or incomplete visit and scheduling one or more notifications indicating completion of the visit. The process then repeats the scheduling loop to schedule future visits/assignments.

In the above example, scheduling occurs at the level of visits/assignments. Once a particular assignment for a virtual visit is due according to scheduling information (e.g. an event-based timestamp), all sub-tasks of the assignment become due. However, in an alternative approach, sub-tasks may be individually scheduled using the same event-based scheduling mechanism.

Once a scheduled time for an assignment/task arrives, the task may be performed automatically (for example, for passive sensor data acquisition tasks, the system may automatically start sensor data collection at the scheduled time). For interactive tasks that cannot be performed automatically, the user is prompted to perform the task, for example, by generating a notification, and/or generating and outputting an appropriate user interface for the task (e.g. instructions for an activity or a questionnaire interface). As mentioned above, the mobile application may display a list of "active" assignments and sub-tasks for selection by the user, and in response to selection, any further required instructions or interfaces for the assignment/task are displayed. The user then confirms once the task has been completed, or submits any information being input, as appropriate to the task.

FIG. 10C illustrates operation of the results service. In step 1060, the results service waits for new results (e.g. these could be results of completed tasks generated by step 1048 or results indicating missed tasks, 1016, or indicating non-applicable tasks, 1028, where a particular task was identified as not applicable to the particular user/device). Received results are stored in a results database (1068) and marked initially as unsent. A process 1062 reads newly received results from the results database and transmits them to a results web server 1070 (forming part of the central study management system). Results may be accumulated and transmitted in batches based on batch transmission criteria as previously set out. Once an acknowledgement of receipt is received from the results web server (test 1064) the result is marked as sent in the results database (step 1066) and may eventually be deleted. The process continues to monitor unsent results in the database and will attempt to resend results for which acknowledgements have not been received. This process can ensure that result data (e.g. sensor data, questionnaire inputs etc.) is correctly uploaded from the mobile application to the central system once assignments have been completed, even in the presence of transmission problems e.g. due to limited bandwidth or intermittent connectivity.

On the server-side, the schedule can also be parsed to see what the user was supposed to do. If there is no explicit miss/complete etc. status for a task, the system displays the task as 'outstanding', indicating that the user device may be offline and that the system expects to have received result data from the user device by now. A study coordinator could use this as a prompt to reach out to the patient to see if any issues (e.g. connectivity problems) can be resolved.

This approach goes beyond dealing with transmission problems, since the system is also able to track what results are expected and when and is able to alert the study coordinator to the status of result collection. This approach provides the system and study coordinators with high visibility into the study progress and any problems in achieving the data collection goals. The system can also distinguish between a complete miss (e.g. patient not completing tasks) and the system not receiving the data (e.g. due to connectivity issues).

Time Zone Handling

The system may provide functionality to enable appropriate time zone handling throughout the application. In an embodiment, when a user is signed up, they provide a time zone that gets stored in a database. This time zone is subject to change day to day, however. In a heavily regulated environment, it is useful for the system to be able to automatically apply the proper time zone of a subject throughout their lifecycle in the system, but a constant feed of time zone data is generally not available from user devices.

Embodiments implement a tiered approach to handling time zones. A calendar of time zones is built that can clearly identify what time zone a user was in that can be easily backfilled and validated across wearable devices. It takes into account the reliability of a device, whether or not the device is being worn/used, and is able to create a series of fallback time zones, the last of which being the one entered upon subject sign up. This allows a system that has no knowledge of user location to identify a time zone from user devices and their peripherals.

The system is able to send time-critical text/email notifications to an end user's device. When time zone data is unreliable, it becomes challenging to guarantee that a notification can be sent at a precise time in relation to the user's current location and time zone. The system compiles time zone data from available devices and peripherals in order to properly schedule notifications and assignments. The system is also able to schedule time-critical sensor data collection windows via this approach. Where possible, this system relies on local notifications on the smartphone, generated by either the schedule, a mobile assignment, or by a peripheral device.

Computer System

Figure 11:
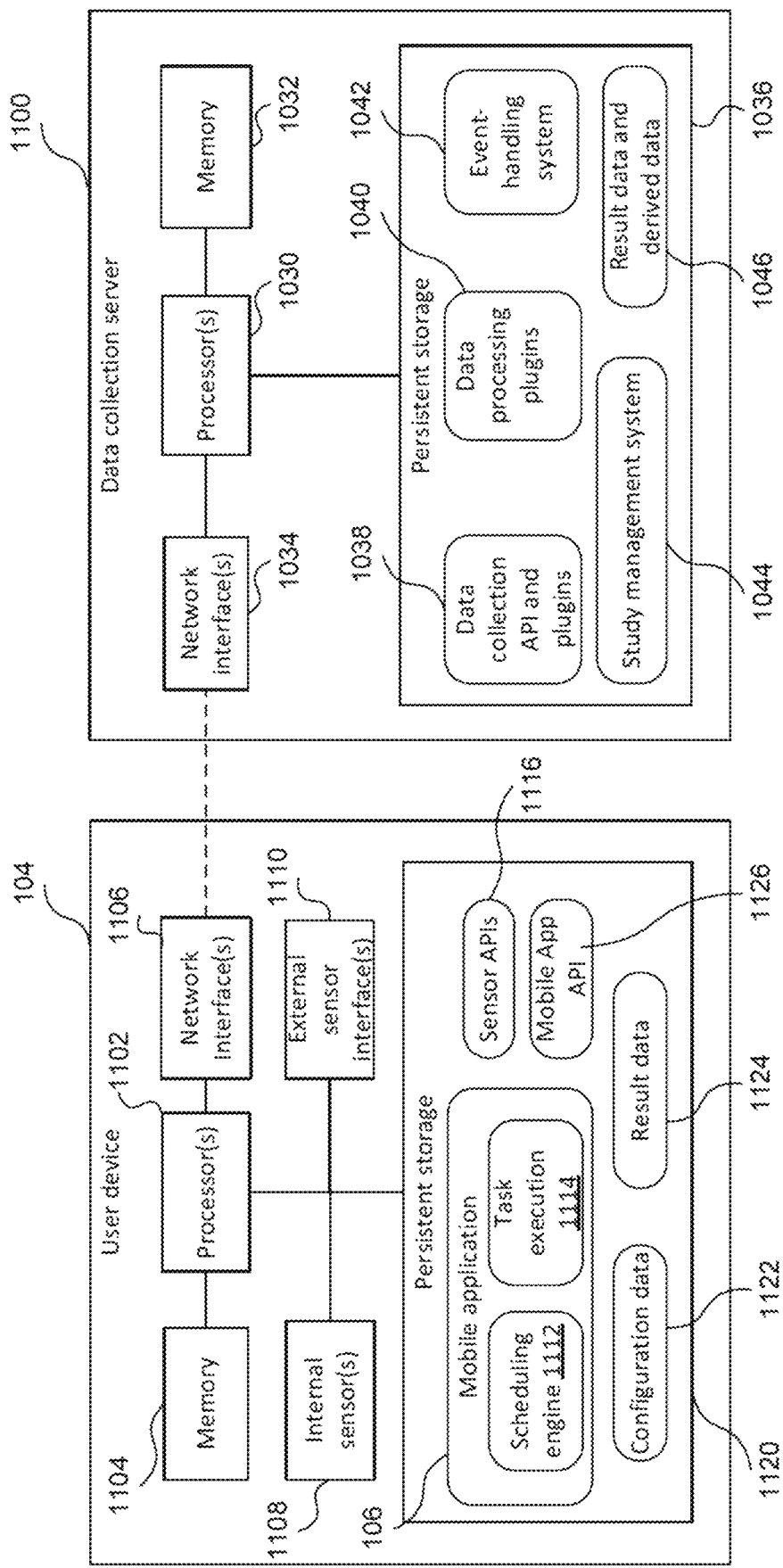
FIG. 11 illustrates a user device and central data collection server for implementing described techniques.

FIG. 11 illustrates elements of a computer system for implementing described processes and techniques. FIG. 11 shows a single representative user device 104, for example a smartphone (though in practice the system will include many such devices), and a data collection server 1100 for implementing various functions of the study management system.

The user device 104 includes one or more processors 1102 together with volatile/random access memory 1104 for storing temporary data and software code being executed.

Network interface(s) 1106 (e.g. Wi-Fi and/or a cellular interface for communicating via a mobile communications network) are provided for communication with other system components (including server 1100) over one or more networks (e.g. Local or Wide Area Networks, including the Internet).

Internal sensors 1108 of the user device may include, for example, an accelerometer, gyroscope, infrared sensor etc. The user device may also include wired and wireless external sensor interface(s), e.g. a USB interface or wireless local interface such as Bluetooth or NFC. Note in some cases external sensor devices may also communicate via network interfaces 1106 (e.g. a Wi-Fi enabled sensor device).

Persistent storage 1120 (e.g. in the form of FLASH memory or SSD, solid-state drive, storage) persistently stores software used by the user device, including the mobile application 106, sensor APIs 1116 and the mobile application API 1126 (the latter could alternatively be considered to form part of the application itself). The mobile application may be structured into sub-components, including, for example, a scheduling engine 1112 for scheduling assignments and data collection activities, notifications, data uploads and other actions, and task execution engine 1114 for carrying out scheduled assignments, tasks and data collection activities. The persistent storage also stores data used and produced by the mobile application, including configuration data 1122 (e.g. the study configuration and associated schedule data) and collected result data 1124 such as sensor data, user input data and interactive assessment data (which may be stored temporarily and then uploaded to the server 1100 in a batch process as described above). The persistent storage also includes other user device software and data (not shown), such as a device operating system.

The user device will include other conventional hardware and software components as known to those skilled in the art (such as user interface elements, e.g. a touch screen and buttons), and the components are interconnected by a data bus (this may in practice consist of several distinct buses such as a memory bus and I/O bus).

The data collection server 1100 includes one or more processors 1030 together with volatile/random access memory 1032 for storing temporary data and software code being executed.

One or more network interface(s) 1034 are provided for communication with the user devices, external/third-party systems, and other system components over one or more communications networks.

Persistent storage 1036 (e.g. in the form of hard disk storage, optical storage, SSD storage and the like) persistently stores server software for managing clinical studies and the associated data collection activities. This includes a study management system 1044, for configuring a study, and generating study datasets based on collected and processed data (including the various configuration and management dashboards described above), as well as various elements implementing the data ingestion pipeline, such as the data collection APIs and plugins 1038, data processing/aggregation plugins 1040, and an event handling system 1042 for managing an event-based data ingestion pipeline.

The persistent storage also includes data used and generated by the software, such as received result data and processed/derived data 1046, as well as study configurations and user data (not shown).

The persistent storage also includes other server software and data (not shown), such as a server operating system. The server will include other conventional hardware and software components as known to those skilled in the art, and the components are interconnected by a data bus (this may in practice consist of several distinct buses such as a memory bus and I/O bus).

While a specific architecture is shown by way of example, any appropriate hardware/software architecture may be employed.

Furthermore, functional components indicated as separate may be combined and vice versa. For example, the functions of the data collection server may be distributed over multiple computer devices, with each computer device handling a subset of processing tasks and/or a subset of data received from a population of user devices (with load balancing implemented as needed). As a concrete example, study configurations and/or received/processed result data may be stored in a separate database server accessible by the server 1100. Similarly, user interface functions (e.g. configuration dashboards) may be implemented by a separate web server.

Functionality may be distributed between system elements in any suitable manner; for example, some processing tasks shown as performed at the user device may be performed at the server or vice versa.

It will be understood that the present invention has been described above purely by way of example, and modification of detail can be made within the scope of the invention.

Note that the terms Amazon, Amazon Web Services, S3, Apple, AppleHealth, HealthKit, Bluetooth and Wi-Fi are registered trademarks and should be read as such throughout this document.

Various aspects and features of the invention are set out in the following numbered clauses.

1. A computer-implemented method for obtaining health-related data at a user device, the method comprising:
   running at the user device a data collection application for obtaining health-related data, the health-related data comprising one or more of: data indicative of user health, and source data from which data indicative of user health can be derived, wherein the data collection application is arranged to support data collection in a plurality of data collection modes, including a sensor-based data collection mode for receiving health-related data from one or more sensors included in or in communication with the user device, and at least one of:
      a user data input mode for obtaining health-related data based on user input of a configurable set of one or more health-related data values; and
      an interactive health assessment mode for executing configurable interactive assessments for obtaining health-related data based on user interaction with the user device;
   and wherein the method further comprises:
      receiving, over a communications network, a data collection configuration from a health monitoring system, the data collection configuration specifying a plurality of data collection activities to be performed at the user device, each data collection activity for obtaining respective health-related data and associated with at least one of the plurality of data collection modes;
      performing each data collection activity by the data collection application in accordance with the at least one data collection mode associated with the data collection activity to obtain health-related data, the obtained health-related data comprising one or more of: sensor data, user input data, and interactive assessment data; and
      transmitting result data to the health monitoring system based on the obtained health-related data.

2. A method according to clause 1, wherein performing a data collection activity in the interactive health assessment mode comprises:
   running an interactive assessment specified in the data collection configuration;
   detecting user interactions with the user device in response to interactive prompts provided via a user interface of the user device; and
   generating health-related data based on the detected user interactions.

3. A method according to clause 2, comprising measuring one or more characteristics of the user interactions, and generating the health-related data based on the measured characteristics, the one or more characteristics optionally comprising one or more of: a response time, and a response accuracy.

4. A method according to any of the preceding clauses, wherein a given interactive assessment comprises a capability test for assessing one or more capabilities of a user, optionally one of: a cognitive test; a perceptual test, for example a visual acuity test or auditory test; a dexterity test; or another interactive test for evaluating and/or stratifying subjects based on their health and/or capabilities.

5. A method according to any of the preceding clauses, wherein performing a data collection activity in the user input mode comprises displaying one or more data input fields specified in the data collection configuration and receiving respective data input values for each field from the user via an interface of the user device.

6. A method according to any of the preceding clauses, wherein a data collection activity performed in the data input mode comprises a data input activity for inputting one or more health-related data values, such as a health status or symptom questionnaire.

7. A method according to any of the preceding clauses, wherein performing data collection in the sensor-based data collection mode comprises identifying at least one sensor included in or in communication with the user device based on the data collection configuration, and obtaining sensor data from the identified at least one sensor.

8. A method according to any of the preceding clauses, wherein the source data from which data indicative of user health can be derived comprises one or more of: user input data; sensor data; and assessment data obtained from an interactive assessment.

9. A method according to any of the preceding clauses, wherein the data collection configuration further comprises schedule data defining a schedule of the data collection activities to be performed at the user device, the configuring comprising determining based on the schedule data, for each of the data collection activities, a target time at which the data collection activity is to be performed by the data collection application; and initiating, by the data collection application, the data collection activities in accordance with the determined target times.

10. A computer-implemented method performed at a user device comprising a data collection application for obtaining health-related data from one or more data sources including one or more sensors, the health-related data comprising one or more of: data indicative of user health, and source data from which data indicative of user health can be derived, the method comprising:
   receiving, over a communications network, a data collection configuration from a health monitoring system, the data collection configuration comprising schedule data defining a schedule of data collection activities to be performed at the user device, each data collection activity for acquiring at the user device respective health-related data;
   configuring the data collection application based on the received data collection configuration, the configuring comprising determining based on the schedule data, for each of the data collection activities, a target time at which the data collection activity is to be performed by the data collection application;
   initiating, by the data collection application, the data collection activities in accordance with the determined target times to obtain health-related data for each data collection activity, wherein at least one of the data collection activities comprises obtaining sensor data using one or more sensors included in or in communication with the user device, the health-related data for the data collection activity comprising the sensor data; and
   transmitting result data to the health monitoring system based on the health-related data obtained for the data collection activities.

11. A method according to clause 9 or 10, wherein the schedule data specifies relative time information for a given data collection activity, and wherein determining the target time for the given data collection activity comprises:
   determining a reference time; and
   computing the target time based on the reference time and the relative time information specified in the schedule data.

12. A method according to clause 11, wherein the relative time information defines a time period that is added to the determined reference time to obtain the target time.

13. A method according to any of clauses 9 to 12, wherein the relative time information specifies a trigger event, wherein the reference time is determined based on occurrence of the trigger event.

14. A method according to clause 13, wherein the trigger event is an event communicated by an event handling system in an event message, wherein the reference time is determined based on receipt of the event message from the event handling system.

15. A method according to any of clauses 9 to 14, wherein the schedule data includes a dynamic event-based timestamp data structure associated with a given data collection activity, the dynamic event-based timestamp data structure specifying a trigger event and a time period relative to occurrence of the trigger event, the method comprising resolving the dynamic event-based timestamp upon detection of the trigger event, wherein resolving the dynamic event-based timestamp comprises:
   calculating a target time from an event time of the event and the time period, and
   adding the calculated target time to the dynamic event-based timestamp data structure.

16. A method according to clause 15, wherein one or more of the user device, data collection application and health monitoring system comprise an event handling system, the method comprising:
   identifying the trigger event from the dynamic event-based timestamp data structure; and
   subscribing to the trigger event at the event handling system.

17. A method according to clause 16, further comprising:
   receiving an event matching the specified trigger event from the event handling system; and
   in response to receiving the event, resolving the timestamp.

18. A method according to any of clauses 13 to 17, wherein the trigger event is a named event selected from a predetermined set of events and optionally includes data associated with the event.

19. A method according to any of clauses 13 to 18, wherein the trigger event comprises one of:
   a sensor event corresponding to a sensor measurement, the sensor measurement optionally meeting a predetermined criterion, for example a sensor value threshold;
   a user input event defining receipt of a user input;
   a status event identifying a status or change in status of the user device or mobile application;
   a timing event; and
   an event generated by the health monitoring system and communicated to the user device over the communications network.

20. A method according to any of clauses 11 to 19, wherein determining the target time for the given data collection activity comprises determining respective time offsets, optionally Daylight Saving Time offsets, for the reference time and the target time, and correcting the target time based on the offsets if they differ.

21. A method according to any of clauses 9 to 20, wherein the data collection configuration comprises, for a given data collection activity, applicability criteria specifying devices and/or users for which the given data collection activity is applicable, the method comprising evaluating the applicability criteria, and scheduling and/or performing the data collection activity in dependence on the evaluation, wherein the applicability criteria optionally comprise one or more device characteristics and/or user characteristics.

22. A method according to any of clauses 9 to 21, wherein the schedule data further specifies a due date for a given data collection activity, the method comprising detecting that the data collection activity was not completed by the specified due date, and in response, rescheduling the data collection activity and/or generating a notification identifying the data collection activity as not completed.

23. A method according to clause 22, comprising determining if the data collection activity meets one or more rescheduling criteria, the criteria preferably based on a number of times the data collection activity has been rescheduled, and if so, rescheduling the data collection activity by computing a new target time for the data collection activity.

24. A method according to any of the preceding clauses, wherein the schedule data defines a schedule of user assignments, each user assignment associated with one or more assignment tasks, and wherein each assignment task comprises at least one data collection activity, wherein each user assignment preferably defines a workflow of assignment tasks to be completed for the assignment.

25. A method according to any of clauses 9 to 24, comprising receiving updated configuration data at the user device in response to changes to a health study configuration at the health monitoring system, wherein the data collection application preferably updates the locally stored configuration and/or modifies the schedule of device collection activities based on the updated configuration data.

26. A method according to any of clauses 9 to 25, comprising scheduling and initiating one or more notifications based on the schedule data, preferably based on dynamically resolvable event-based timestamps specified for one or more notifications, the notifications optionally including push notifications or other electronic messages for output at the user device.

27. A method according to any of clauses 9 to 26, comprising scheduling a time for transmission of the result data based on the schedule data, and performing the transmitting step at the scheduled time.

28. A method according to any of clauses 9 to 27, wherein initiating a data collection activity comprises at least one of:
   performing the data collection activity automatically by the user device at the determined target time;
   prompting the user at the user device at the determined target time to start the data collection activity; and
   making the data collection activity available at the determined target time for selection and initiation by the user, optionally via a menu displayed at the user device.

29. A method according to any of clauses 9 to 28, wherein the data collection activities comprise one or more user input based data collection activities, the user input based data collection activities including receiving one or more user inputs via an interface of the user device, and wherein the transmitted result data includes result data based on the received user input(s).

30. A method according to clause 29, wherein the one or more user input based data collection activities comprise one or more of:
- a data input activity for inputting one or more health-related data values, such as a health status or symptom questionnaire;
- an interface-based interactive health assessment based on user interaction, optionally comprising detecting user interaction in response to interactive prompts via a user interface of the user device, the method comprising deriving health-related data from one or more user interactions.

31. A method according to any of the preceding clauses, wherein the data collection activities comprise at least one sensor-based data collection activity and at least one further data collection activity selected from the group comprising: a further sensor-based data collection activity, a data input activity, and an interface-based interactive health assessment.

32. A method according to any of the preceding clauses, wherein the data collection activities comprise one or more of:
- an interactive assignment task, comprising instructing a user to perform an activity and receiving sensor data from one or more sensors relating to performance of the activity; and
- passive acquisition of sensor data from one or more sensors, optionally over a predetermined time period.

33. A method according to any of the preceding clauses, wherein the configuration data comprises instructional information to be output to the user indicating one or more tasks to be performed by the user during one or more data collection activities.

34. A method according to any of the preceding clauses, the transmitting step comprising collecting health-related data for a plurality of the data collection activities at the user device and performing a batch transmission for the collected data in accordance with one or more batch transmission criteria.

35. A computer-implemented method performed at a user device comprising a data collection application for obtaining health-related data, the health-related data comprising one or more of: data indicative of user health, and source data from which data indicative of user health can be derived, the method comprising:
- receiving, over a communications network, a data collection configuration from a health monitoring system, the data collection configuration defining a plurality of data collection activities to be performed at the user device, each data collection activity for acquiring at the user device respective health-related data;
- performing, by the data collection application, the data collection activities in accordance with the data collection configuration to obtain health-related data for each data collection activity; and
- transmitting result data to the health monitoring system based on the collected health-related data, the transmitting comprising:
- collecting health-related data for a plurality of the data collection activities at the user device and performing a batch transmission for the collected data in accordance with one or more batch transmission criteria.

36. A method according to clause 34 or 35, wherein the one or more batch transmission criteria are specified in the data collection configuration.

37. A method according to any of clauses 34 to 36, wherein the batch transmission criteria specify one or more of:
- a group of data collection activities for which result data is to be transmitted in a batch;
- time information specifying a time at which batch transmission is to be performed;
- upload frequency information specifying a frequency at which batch transmission is to be performed; and
- connectivity criteria, optionally specifying availability of a preferred network connection.

38. A method according to any of clauses 34 to 37, comprising determining a time for transmission in dependence on the batch transmission criteria; and performing the batch transmission at the determined time.

39. A method according to clause 38, comprising determining the time for transmission based on schedule data included in the data collection configuration, preferably wherein the schedule data specifies relative time information for performing data transmission, and wherein determining the transmission time comprises: determining a reference time; and computing the transmission time based on the reference time and the relative time information specified in the schedule data.

40. A method according to clause 39, wherein the relative time information specifies a trigger event, wherein the reference time is determined based on detection of the trigger event at the user device, optionally wherein the relative time information comprises a dynamically resolvable event-based timestamp.

41. A method according to any of clauses 34 to 40, comprising determining the time for transmission based on network connectivity status and/or available bandwidth.

42. A method according to any of clauses 34 to 41, wherein the batch transmission criteria identify one of a plurality of network interfaces available at the user device as a preferred network interface, and selecting the preferred network interface for performing the batch transmission and/or performing transmission at a time when network connectivity is available via the preferred network interface.

43. A method according to any of clauses 34 to 42, comprising monitoring for receipt of a confirmation message from the health monitoring system indicating receipt of the batch transmission at the health monitoring system and further performing at least one of:
- repeating the batch transmission for the collected data after a predetermined time period if a confirmation message is not received; and
- deleting the collected health-related data in response to receipt of the confirmation message.

44. A user device comprising at least one processor and associated memory, configured to perform a method as set out in any of clauses 1 to 43.

45. A non-transitory computer-readable medium comprising software code adapted, when executed on a data processing apparatus, to perform a method as set out in any of clauses 1 to 43.

46. A computer-implemented method performed at a health study management system for collecting health-related data from a plurality of data sources, the health-related data comprising one or more of: data indicative of user health, and source data from which data indicative of user health can be derived, the data sources including sensor devices associated with monitored system users, the method comprising:
- providing a modular data ingestion subsystem comprising an extensible set of interface modules, each interface module adapted to receive health-related data from a respective type of data source;

providing a modular data processing subsystem comprising an extensible set of processing modules, each processing module adapted to process health-related data to determine one or more derived health indicators from the health-related data; and receiving configuration information for a health study to be conducted using the health study management system, the configuration information specifying a plurality of data collection activities, each for collecting respective health-related data from one or more data sources, the data collection activities comprising at least one sensor-based data collection activity associated with a sensor device type to be used for collecting sensor data, and processing to be performed on collected sensor data, configuring the data ingestion subsystem and data processing subsystem in accordance with the configuration information for the health study;

collecting health-related data from the data sources via the configured data ingestion subsystem;

processing the collected health-related data using the configured data processing subsystem;

generating a study dataset based on the processed health-related data; and outputting the study dataset.

47. A method according to clause 46, wherein the configuring step comprises configuring data flows for data collection activities by selecting one or more interface modules and/or processing modules for handling health-related data based on the configuration data.

48. A method according to clause 46 or 47, wherein the configuring step comprises associating with a given data source at least one of:
- a selected interface module of the data ingestion subsystem for inputting health-related data from the given source at the health study management system; and
- a processing module of the processing subsystem for processing health-related data from the given source;
- the system further configured to receive and/or process health-related data from the given source using the configured interface module and/or the configured processing module.

49. A method according to any of clauses 46 to 48, wherein the configuring step comprises selecting, for the at least one sensor-based data collection activity, an interface module of the data ingestion subsystem adapted for receiving data from the associated sensor device type and a processing module of the data processing subsystem to perform processing of sensor data from the sensor device type.

50. A method according to clause 48 or 49, wherein the data sources further comprise one or more of: data input provided via user devices associated with monitored system users; and interactive health assessment data obtained from interactive health assessments run on user devices associated with monitored system users.

51. A method according to clause 50, wherein the data collection activities further comprise one or more user input based data collection activities, the user input based data collection activities including receiving one or more user inputs via an interface of a user device associated with a monitored system user, wherein the one or more user input based data collection activities optionally comprise one or more of:

- a data input activity for inputting one or more health-related data values, such as a health status or symptom questionnaire;
- an interface-based interactive health assessment based on user interaction, optionally comprising detecting user interaction in response to interactive prompts via a user interface of the user device.

52. A method according to any of clauses 46 to 51, wherein the processing modules comprise at least one of:
- processing modules for processing data from a plurality of different types of data source, optionally including a plurality of sensor device types; and
- processing modules for implementing a plurality of different processing algorithms to determine derived health indicators from health-related data.

53. A method according to any of clauses 46 to 52, wherein the configuring step comprises adding one or more interface modules to the data ingestion subsystem and/or adding one or more processing modules to the data processing subsystem to implement a data flow for a given data collection activity in accordance with the configuration information.

54. A method according to any of clauses 46 to 53, comprising receiving a selection of one or more predefined data collection activities from a catalogue of data collection activities and performing configuration based on the selected predefined data collection activities.

55. A method according to any of clauses 46 to 54, wherein the configuration information specifies study participants for whom data is to be collected, the configuring step comprising associating a user device and/or one or more sensor devices with each study participant and configuring the data ingestion subsystem to receive data from the user device and/or one or more sensor devices.

56. A method according to any of clauses 46 to 55, further comprising transmitting a study configuration to a respective user device associated with each of a group of study participants to configure the user device to perform the data collection activities, the study configuration preferably comprising schedule data defining a schedule of data collection activities to be performed by a health monitoring application at the user device.

57. A method according to any of clauses 46 to 56, comprising receiving a plurality of health study configurations associated with respective health studies; and, for each health study, configuring at least one of: the data ingestion subsystem; the data processing subsystem; and a respective group of user devices associated with participants of the health study.

58. A method according to any of clauses 46 to 57, comprising providing in the data ingestion subsystem one or both of:
- a first interface for interfacing with sensor devices associated with user devices of study participants, wherein the first interface preferably comprises an extensible set of modules for interfacing with respective types of sensors or sensor subsystems included in, or adapted to communicate with, the user devices;
- a second interface for interfacing with one or more remote data collection services adapted to collect data from standalone sensor devices, the second interface preferably comprising an extensible set of modules for receiving data from the remote data collection services, optionally comprising respective web service interfaces.

59. A method according to clause 58, comprising providing in the data ingestion subsystem a common data ingestion interface configured to receive sensor data from the user devices via the first interface and to receive sensor data from standalone sensor devices using the remote data collection services via the second interface.

60. A method according to clause 59, wherein the data ingestion and/or data processing subsystems implement an event-driven data ingestion pipeline, the method comprising, at the data ingestion subsystem, generating events comprising collected health-related data and publishing the events to an event handling system; and, at the processing subsystem, consuming the events from the event handling system and processing the collected health-related data included in the events, the processing subsystem optionally generating further events including derived health indicators derived from the health-related data.

61. A method according to any of clauses 46 to 60, further comprising formatting health-related data from a plurality of data sources and/or derived health indicators in accordance with a common health data model and/or outputting, processing and/or storing the data using the common health data model.

62. A system comprising at least one processor with associated memory configured to perform a method according to any of clauses 46 to 61.

63. One or more non-transitory computer readable media comprising software code configured, when executed by one or more data processing devices, to perform a method as set out in any of clauses 46 to 61.

64. A computer-implemented method performed at a user device for obtaining health-related data, the health-related data comprising one or more of: data indicative of user health, and source data from which data indicative of user health can be derived, the method comprising:
receiving, over a communications network, a data collection configuration from a health monitoring system, the data collection configuration comprising schedule data defining a schedule of data collection activities to be performed at the user device, each data collection activity for acquiring at the user device respective health-related data;
determining based on the schedule data, for each of the data collection activities, a target time at which the data collection activity is to be performed;
initiating the data collection activities at the user device in accordance with their respective determined target times to obtain health-related data for the data collection activities; and
transmitting result data to the health monitoring system based on the obtained health-related data.

65. A method according to clause 64, wherein the schedule data specifies relative time information for a given data collection activity, and wherein determining the target time for the given data collection activity comprises:
determining a reference time; and
computing the target time based on the reference time and the relative time information specified in the schedule data, wherein the relative time information preferably defines a time period that is added to the determined reference time to obtain the target time.

66. A method according to clause 65, wherein the relative time information specifies a trigger event, wherein the reference time is determined based on occurrence of the trigger event.

67. A method according to clause 66, wherein the trigger event is an event communicated by an event handling system in an event message, wherein the reference time is determined based on receipt of the event message from the event handling system.

68. A method according to any of clauses 64 to 67, wherein the schedule data includes a dynamic event-based timestamp associated with a given data collection activity, the dynamic event-based timestamp specifying a trigger event and a time period relative to occurrence of the trigger event, the method comprising resolving the dynamic event-based timestamp upon detection of the trigger event, wherein resolving the dynamic event-based timestamp information comprises:
calculating a target time from an event time of the trigger event and the time period, and
adding the calculated target time to the dynamic event-based timestamp.

69. A method according to clause 67 or 68, wherein the user device and/or health monitoring system implement an event handling system, the method comprising:
identifying the trigger event from the dynamic event-based timestamp; and
subscribing to the trigger event at the event handling system; and optionally further comprising:
receiving an event matching the specified trigger event from the event handling system; and
in response to receiving the event, resolving the dynamic event-based timestamp.

70. A method according to any of clauses 66 to 69, wherein the trigger event is a named event selected from a predetermined set of events and optionally includes data associated with the event.

71. A method according to any of clauses 66 to 70, wherein the trigger event comprises one of:
a sensor event corresponding to a sensor measurement, the sensor measurement optionally meeting a predetermined criterion, for example a sensor value threshold;
a user input event defining receipt of a user input;
a status event identifying a status or change in status of the user device;
a timing event; and
an event generated by the health monitoring system and communicated to the user device over the communications network.

72. A method according to any of clauses 65 to 71, wherein determining the target time for the given data collection activity comprises determining respective time offsets, optionally Daylight Saving Time offsets, for the reference time and the target time, and correcting the target time based on the offsets if they differ.

73. A method according to any of clauses 64 to 72, wherein the data collection configuration comprises, for a given data collection activity, applicability criteria specifying devices and/or users for which the given data collection activity is applicable, the method comprising evaluating the applicability criteria, and scheduling and/or performing the data collection activity in dependence on the evaluation, wherein the applicability criteria optionally comprise one or more device characteristics and/or user characteristics.

74. A method according to any of clauses 64 to 73, wherein the schedule data further specifies a due date for a given data collection activity, the method comprising detecting that the data collection activity was not completed by the specified due date, and in response, rescheduling the data collection activity and/or generating a notification identifying the data collection activity as not completed.

75. A method according to clause 74, comprising determining if the data collection activity meets one or more rescheduling criteria, the criteria preferably based on a number of times the data collection activity has been rescheduled, and if so, rescheduling the data collection activity by computing a new target time for the data collection activity.

76. A method according to any of clauses 64 to 75, comprising scheduling and initiating one or more notifications based on the schedule data, preferably based on dynamically resolvable event-based timestamps specified for one or more notifications, the notifications optionally including push notifications or other electronic messages for output at the user device.

77. A method according to any of clauses 64 to 76, comprising scheduling a time for transmission of the result data based on the schedule data, and transmitting the result data to the health monitoring system at the scheduled time.

78. A method according to any of clauses 64 to 77, comprising configuring a data collection application at the user device to carry out the data collection activities in accordance with the determined target times.

79. A method according to any of clauses 64 to 78, wherein initiating a data collection activity comprises at least one of:
   performing the data collection activity automatically by the user device at the determined target time;
   prompting the user at the user device to start the data collection activity; and
   making the data collection activity available for selection and initiation by the user via a menu displayed at the user device.

80. A method according to any of clauses 64 to 79, wherein the data collection activities comprise one or more user input based data collection activities, the user input based data collection activities including receiving one or more user inputs via an interface of the user device, and wherein the obtained health-related data is based on the received user input(s).

81. A method according to clause 80, wherein the one or more user input based data collection activities comprise one or more of:
   a data input activity for inputting one or more health-related data values, such as a health status or symptom questionnaire;
   an interface-based interactive health assessment based on user interaction, optionally comprising detecting user interaction in response to interactive prompts via a user interface of the user device, the method comprising deriving health-related data from one or more user interactions.

82. A method according to clause 81, wherein the interactive health assessment comprises generating health-related data based on one or more measured characteristics of the detected user interactions, the one or more characteristics optionally comprising one or more of: a response time, and a response accuracy.

83. A method according to clause 81 or 82, wherein the interactive health assessment comprises a capability test for assessing one or more capabilities of a user, optionally one of: a cognitive test; a perceptual test, for example a visual acuity test or auditory test; a dexterity test; or another interactive test for evaluating and/or stratifying subjects based on their health and/or capabilities.

84. A method according to any of clauses 64 to 83, wherein at least one of the data collection activities comprises acquiring sensor data from one or more sensors included in or in communication with the user device, wherein the obtained health-related data comprises the acquired sensor data.

85. A method according to any of clauses 64 to 84, wherein the data collection configuration comprises instructional information, the method comprising outputting the instructional information to the user indicating one or more tasks to be performed by the user during one or more data collection activities.

86. A method according to any of clauses 64 to 85, comprising receiving updated configuration data from the health monitoring system, and updating the locally stored data collection configuration and/or modifying the schedule of device collection activities based on the updated configuration data.

87. A method according to any of clauses 64 to 86, wherein the schedule data defines a schedule of user assignments, each user assignment associated with one or more assignment tasks, and wherein each assignment task comprises at least one data collection activity, wherein each user assignment preferably defines a workflow of assignment tasks to be completed for the assignment.

88. A user device comprising at least one processor and associated memory, configured to perform a method as set out in any of clauses 64 to 87.

89. A non-transitory computer-readable medium comprising software code adapted, when executed on a data processing apparatus, to perform a method as set out in any of clauses 64 to 88.

90. A method performed in a health study management system for collecting health-related data from a plurality of user devices associated with participants in a health study, the health-related data comprising one or more of: data indicative of user health, and source data from which data indicative of user health can be derived, the method comprising:
   receiving a health study configuration specifying data collection activities for a health study and scheduling information for the data collection activities;
   for each study participant, generating a data collection configuration including schedule data based on the health study configuration for a user device associated with the study participant, the schedule data defining a schedule of data collection activities to be performed at the user device, each data collection activity for obtaining respective health-related data for the study participant; and
   transmitting, to each user device, the data collection configuration generated for the user device to configure data collection activities to be performed at the user device.

91. A method according to clause 90, further comprising:
   receiving health-related data from a plurality of the user devices at the health study management system, the health-related data obtained at each user device based on the schedule of data collection activities generated for the user device;
   processing the health-related data;
   compiling a study dataset for the health study from the processed health-related data; and
   outputting the study dataset.

92. A method according to clause 90 or 91, wherein the data collection activities comprise one or more user input based data collection activities, the user input based data collection activities including receiving one or more user inputs via an interface of the user device, wherein the one or more user input based data collection activities optionally comprise one or more of:
  a data input activity for inputting one or more health-related data values, such as a health status or symptom questionnaire;
  an interface-based interactive health assessment based on user interaction, optionally comprising detecting user interaction in response to interactive prompts via a user interface of the user device.

93. A method according to any of clauses 90 to 92, wherein the data collection activities comprise at least one sensor-based data collection activity for obtaining sensor data from one or more sensors, optionally including: one or more sensors integrated into a user device; one or more external sensors configurable to communicate with a user device; and one or more external sensor devices configurable to provide sensor data to the health study management system.

94. A method according to any of clauses 90 to 93, wherein the schedule data defines target times for a plurality of data collection activities.

95. A method according to clause 94, wherein, for a given data collection activity, the schedule data specifies relative time information relative to a reference time, preferably comprising a time period that is to be added to the determined reference time, wherein the relative time information optionally specifies a trigger event, wherein occurrence of the trigger event at the user device determines the reference time.

96. A method according to clause 95, further comprising: generating an event matching the specified trigger event and communicating the event to the user device to trigger resolution of the dynamic timing information.

97. A method according to any of clauses 90 to 96, comprising configuring a result processing system at the health study management system based on the health study configuration to perform the processing of the health-related data from the user devices.

98. A method according to clause 97, comprising providing in the result processing system one or more of:
  a modular data ingestion subsystem comprising an extensible set of interface modules, each interface module adapted to receive health-related data from a respective data source;
  a modular data processing subsystem comprising an extensible set of processing modules, each processing module adapted to process health-related data to determine one or more derived health indicators from the health-related data;
the method comprising configuring the modular data ingestion subsystem and/or the modular data processing subsystem in dependence on the health study configuration.

99. A method according to clause 98, comprising configuring data flows for each of a plurality of data collection activities by selecting one or more interface modules and/or processing modules for handling health-related data generated by each data collection activity based on the health study configuration.

100. A method according to 98 or 99, wherein the processing modules comprise modules for implementing a plurality of different processing algorithms to determine derived health indicators from health-related data, optionally wherein a given processing module performs an aggregation function to generate a derived health indicator based on a plurality of data values of the health-related data.

101. A method according to any of clauses 90 to 100, wherein receiving a health study configuration comprises receiving a selection of one or more predefined data collection activities from a catalogue of data collection activities and performing configuration of the result processing system and/or generating data collection configurations for user devices based on the selected predefined data collection activities.

102. A method according to any of clauses 90 to 101, further comprising formatting health-related data from a plurality of sources in accordance with a common health data model and/or outputting, processing and/or storing the health-related data using the common health data model.

103. A method performed in a health study management system for collecting health-related data from a plurality of user devices associated with participants in a health study, the health-related data comprising one or more of: data indicative of user health, and source data from which data indicative of user health can be derived, the method comprising:
  receiving a health study configuration, the health study configuration specifying data collection activities to be performed at user devices for the health study;
  transmitting configuration data to each of the plurality of user devices to configure the user devices to perform the specified data collection activities;
  receiving a first set of health-related data from the user devices in accordance with the configured data collection activities;
  receiving one or more changes to the health study configuration;
  generating updated configuration data for one or more of the user devices in accordance with the one or more changes to the health study configuration;
  transmitting the updated configuration data to the one or more user devices to reconfigure data collection at the one or more devices in accordance with the changed health study configuration;
  receiving a second set of health-related data after reconfiguration of the user devices; and
  generating and outputting a study dataset for the health study based on the first and second sets of health-related data.

104. A method according to clause 103, wherein the one or more changes comprise changes to the data collection activities to be performed and/or to the data to be collected by one or more of the data collection activities.

105. A method according to clause 104, wherein the one or more changes comprise one or more of: discontinuing one of the specified data collection activities; and adding a new data collection activity to the specified data collection activities.

106. A method according to any of clauses 103 to 105, wherein the health study configuration comprises scheduling information for the data collection activities, the generated configuration data comprising schedule data specifying times at which the data collection activities are to be performed at a user device, and wherein the one or more change comprises changes to the scheduling information.

107. A method according to clause 106, wherein generating updated configuration data comprises changing a time or frequency at which data collection is to be performed at a user device for a given data collection activity.

108. A method according to any of clauses 103 to 107, comprising reconfiguring processing to be applied to received health-related data based on the changes to the health study configuration.

109. A method according to clause 108, wherein the processing is performed by a configurable processing subsystem of the health study management system, the method comprising reconfiguring the configurable processing subsystem in dependence on the changes to the health study configuration, optionally to configure one or more interface modules and/or processing modules for receiving and/or processing health-related data from the user devices.

110. A method performed in a health study management system for configuring the collection of health-related data from a plurality of user devices associated with participants in a health study, the health-related data comprising one or more of: data indicative of user health, and source data from which data indicative of user health can be derived, the method comprising:
maintaining in a database a catalogue of predefined data collection activities, each data collection activity performable at user devices for obtaining health-related data;
receiving a health study configuration for a health study, the health study configuration identifying a selected group of data collection activities from the catalogue, each of the group of data collection activities for acquiring respective health-related data for the health study;
generating, based on the catalogue and the selected group of data collection activities, a data collection configuration for each of a plurality of user devices associated with study participants, the data collection configuration specifying the data collection activities to be performed at a user device; and
transmitting to each user device the generated data collection configuration to configure the user device to perform the specified data collection activities.

111. A method according to clause 110, wherein the data collection activities defined in the catalogue comprise one or more of:
data input activities, wherein a data input activity comprises inputting one or more health-related data values, for example in the form of a health status or symptom questionnaire;
interactive health assessments, wherein an interactive health assessment comprises obtaining health-related data based on user interaction, optionally comprising detecting user interaction in response to interactive prompts via a user interface of the user device and deriving health-related data from one or more user interactions; and
sensor-based data collection activities for acquiring sensor data from one or more sensors included in or in communication with a user device, wherein the obtained health-related data comprises the acquired sensor data.

112. A method according to clause 110 or 111, wherein the health study management system comprises a result processing system for processing result data received from user devices based on performance of the data collection activities at the user devices, the method further comprising configuring the result processing system based on the selected predefined data collection activities.

113. A method according to clause 112, comprising providing in the result processing system one or more of:
a modular data ingestion subsystem comprising a set of interface modules, each interface module adapted to receive health-related data from a respective data source;
a modular data processing subsystem comprising a set of processing modules, each processing module adapted to process health-related data to determine one or more derived health indicators from the health-related data;
the method comprising configuring the modular data ingestion subsystem and/or the modular data processing subsystem in dependence on the health study configuration.

114. A method according to clause 113, comprising configuring data flows for each of a plurality of data collection activities by selecting one or more interface modules and/or processing modules for handling health-related data generated by each data collection activity based on the health study configuration.

115. A method according to any of clauses 110 to 114, wherein generating a data collection configuration comprises including schedule data in the data collection configuration based on scheduling information in the health study configuration, the schedule data defining a schedule for the data collection activities to be performed at a user device.

116. A method according to 115, wherein the schedule data comprises time information specifying one or more times at which a data collection activity is to be performed, the time information optionally comprising dynamically resolvable target times that are resolvable at the user device.

117. A method according to any of clauses 110 to 116, comprising generating the data collection configurations based on the selected data collection activities and a language selected for each user device.

118. A method according to any of clauses 110 to 117, comprising retrieving from the catalogue specification data for each of the selected group of data collection activities, the specification data for a data collection activity specifying one or more of: data to be collected by the data collection activity; a type of sensor device to be used to obtain data for a sensor-based data collection activity; input values to be obtained from a user for a data input activity; an interactive assessment to be run for an interactive assessment activity; and processing to be performed on health-related data obtained by the data collection activity; the method further comprising generating the data collection configuration for each user device and/or configuring a result processing system based on the retrieved specification data.

119. A computer-implemented method performed at a health study management system for collecting health-related data for a health study, the health-related data comprising one or more of: data indicative of user health, and source data from which data indicative of user health can be computed, the method comprising:
receiving health-related data associated with a study participant from one or more devices, the health-related data comprising data generated by a plurality of data collection activities performed using the one or more devices;
processing the health-related data received for each data collection activity to format the data in accordance with a common health data model;
determining one or more derived health indicators from the formatted health-related data;
generating a study dataset using the derived health indicators; and
outputting the study dataset.

120. A method according to clause 119, wherein the data collection activities comprise data collection activities associated with multiple data collection modes of a data collection application provided at a user device, wherein the processing step comprises formatting data generated by the multiple data collection modes in accordance with the common data model.

121. A method according to clause 120, wherein the data collection modes comprise one or more of:
- a sensor-based data collection mode for receiving health-related data from one or more sensors included in or in communication with the user device;
- a user data input mode for obtaining health-related data based on user input of a set of one or more health-related data values; and
- an interactive health assessment mode for executing interactive assessments for obtaining health-related data based on user interaction with the user device.

122. A method according to any of clauses 119 to 121, wherein the data collection activities comprise data collection activities associated with a plurality of sensors, the processing step comprising formatting data generated by the plurality of sensors in accordance with the common data model.

123. A method according to any of clauses 119 to 122, wherein the determining step comprises computing at least one derived health indicator based on health-related data received for a plurality of data collection activities.

124. A method according to any of clauses 119 to 123, wherein the common health data model comprises value data including at least a value field specifying a value of a health measure and a unit field specifying a unit of measurement applicable to the value, and preferably further comprising one or more of: a data type field, and an identifier field identifying a type of the health measure.

125. A method according to clause 124, wherein the common health data model comprises key data associated with the value data comprising one or more of: a source, a measurement event type, a user identifier, a device identifier, and one or more acquisition timestamps, optionally comprising start and end timestamps for an acquisition period.

126. A method according to clause 125, comprising storing the formatted health-related data including key and value data in a database and to enable searching, querying and/or collation of health-related data based on one or more of the key data elements.

127. A method according to any of clauses 119 to 126, comprising repeating the receiving, processing and determining steps for each of a plurality of study participants, and generating the study dataset using the derived health indicators for each of the study participants.

128. A method according to any of clauses 119 to 127, wherein the derived health indicators comprise one or more health metrics associated with one or more outcome measures or end points of the study.

129. A method according to any of clauses 119 to 128, comprising receiving a study configuration for the health study, and performing the receiving, processing and determining steps in dependence on the study configuration.

130. A system having means, optionally comprising at least one processor with associated memory, configured to perform a method as set out in any of clauses 90 to 129.

131. One or more non-transitory computer readable media comprising software code configured, when executed by one or more data processing devices, to perform a method as set out in any of clauses 90 to 129.

Features of different aspects set out in the above numbered clauses may be combined in any suitable combination consistent with the above disclosure. Thus, dependent features of one aspect may be applied to any of the other aspects.

The invention claimed is:

1. A computer-implemented method performed at a health study management system for collecting health-related data from a plurality of data sources, the health-related data comprising one or more of: data indicative of user health, and source data from which data indicative of user health can be derived, the data sources including a plurality of user devices associated with health study participants, the method comprising:
- providing a modular data ingestion subsystem comprising an extensible set of interface modules, each interface module adapted to receive health-related data from a respective type of data source;
- providing a modular data processing subsystem comprising an extensible set of processing modules, each processing module adapted to process health-related data to determine one or more derived health indicators from the health-related data; and
- receiving a given health study configuration for a given health study, from a plurality of health study configurations for a plurality of health studies, each health study configuration being associated with a respective health study, wherein the given health study is to be conducted using the health study management system, the given health study configuration specifying a plurality of data collection activities for a plurality of study participants of the given health study, each data collection activity for collecting respective health-related data, the data collection activities specifying one or more sensor-based data collection activities associated with a sensor device type to be used for collecting sensor data, and processing to be performed on collected sensor data,
- automatically configuring the data ingestion subsystem and data processing subsystem in accordance with the given health study configuration to receive and process health-related data for the given health study from the data sources;
- for each of the plurality of user devices:
  - associating the user device with a study participant of the given health study,
  - generating a data collection configuration based on the given health study configuration, and
  - automatically transmitting the data collection configuration to eaeh the user device, wherein the data collection configuration is arranged to configure the user device for the collection of health-related data from a plurality of data sources associated with the user device;
- collecting the health-related data from the user devices via the configured data ingestion subsystem;
- processing the collected health-related data using the configured data processing subsystem;
- generating a study dataset based on the processed health-related data; and
- outputting the study dataset.

2. A method according to claim 1, wherein the configuring step comprises configuring data flows for data collection activities by selecting one or more interface modules and/or processing modules for handling health-related data based on the health study configuration.

3. A method according to claim 1, wherein the configuring step comprises associating with a given data source at least one of:
- a selected interface module of the data ingestion subsystem for inputting health-related data from the given source at the health study management system; and a processing module of the processing subsystem for processing health-related data from the given source;

the system further configured to receive and/or process health-related data from the given source using the configured interface module and/or the configured processing module.

4. A method according to claim 1, wherein the configuring step comprises selecting, for the one or more sensor-based data collection activities, an interface module of the data ingestion subsystem adapted for receiving data from the associated sensor device type and a processing module of the data processing subsystem to perform processing of sensor data from the sensor device type.

5. A method according to claim 3, wherein the data sources further comprise one or more of: data input provided via the user devices associated with health study participants; and interactive health assessment data obtained from interactive health assessments run on user devices associated with the health study participants.

6. A method according to claim 5, wherein the data collection activities further comprise one or more user input based data collection activities, the user input based data collection activities including receiving one or more user inputs via an interface of a user device associated with one of the health study participants, wherein the one or more user input based data collection activities comprise one or more of:

a data input activity for inputting one or more health-related data values, such as a health status or symptom questionnaire;

an interface-based interactive health assessment based on user interaction, comprising detecting user interaction in response to interactive prompts via a user interface of the user device.

7. A method according to claim 1, wherein the processing modules comprise at least one of:

processing modules for processing data from a plurality of different types of data source, including a plurality of sensor device types; and processing modules for implementing a plurality of different processing algorithms to determine derived health indicators from health-related data.

8. A method according to claim 1, wherein the configuring step comprises adding one or more interface modules to the data ingestion subsystem and/or adding one or more processing modules to the data processing subsystem to implement a data flow for a given data collection activity in accordance with the configuration information.

9. A method according to claim 1, comprising receiving a selection of one or more predefined data collection activities from a catalogue of data collection activities and performing configuration based on the selected predefined data collection activities.

10. A method according to claim 1, wherein the health study configuration specifies the health study participants for whom data is to be collected, the configuring step comprising associating one of the user devices and/or one or more sensor devices with each health study participant and configuring the data ingestion subsystem to receive data from the user device and/or one or more sensor devices.

11. A method according to claim 1, wherein the data collection configuration comprises schedule data defining a schedule of data collection activities to be performed by a health monitoring application at the user device.

12. A method according to claim 1, comprising receiving a plurality of health study configurations associated with respective health studies; and, for each health study, configuring at least one of: the data ingestion subsystem; the data processing subsystem; and a respective group of user devices associated with the participants of the health study.

13. A method according to claim 1, comprising providing in the data ingestion subsystem one or both of:

a first interface for interfacing with sensor devices associated with the user devices of study participants, wherein the first interface comprises an extensible set of modules for interfacing with respective types of sensors or sensor subsystems included in, or adapted to communicate with, the user devices;

a second interface for interfacing with one or more remote data collection services adapted to collect data from standalone sensor devices, the second interface comprising one or more of: an extensible set of modules for receiving data from the remote data collection services; and a set of web service interfaces.

14. A method according to claim 13, comprising providing in the data ingestion subsystem a common data ingestion interface configured to receive sensor data from the user devices via the first interface and to receive sensor data from standalone sensor devices using the remote data collection services via the second interface.

15. A method according to claim 14, wherein the data ingestion and/or data processing subsystems implement an event-driven data ingestion pipeline, the method comprising, at the data ingestion subsystem, generating events comprising collected health-related data and publishing the events to an event handling system; and, at the processing subsystem, consuming the events from the event handling system and processing the collected health-related data included in the events, the processing subsystem generating further events including derived health indicators derived from the health-related data.

16. A method according to claim 1, further comprising formatting health-related data from a plurality of data sources and/or derived health indicators in accordance with a common health data model and/or outputting, processing and/or storing the data using the common health data model.

17. A computer-implemented method performed at a health study management system for collecting health-related data for a health study from a plurality of sources, the health-related data comprising one or more of: data indicative of user health, and source data from which data indicative of user health can be computed, the data sources including a plurality of user devices associated with health study participants; the method comprising:

providing a modular data ingestion subsystem comprising an extensible set of interface modules, each interface module adapted to receive health-related data from a respective type of data source;

providing a modular data processing subsystem comprising an extensible set of processing modules, each processing module adapted to process health-related data to determine one or more derived health indicators from the health-related data; and receiving a given health study configuration for a given health study, from a plurality of health study configurations for a plurality of health studies, each health study configuration associated with a respective health study, wherein the given health study is to be conducted using the health study management system, the given health study configuration specifying a plurality of data collection activities for a plurality of study participants of the given health study, each data collection activity for collecting respective health-related data, the data collection activities specifying one or more sensor-based data collection activities associated with a sensor device type to be used for collecting sensor data, and processing to be performed on collected sensor data, automatically configuring the data ingestion subsystem and data processing subsystem in accordance with the given health study configuration to receive and process health-related data for the given health study from the data sources;

for each of the plurality of user devices:
associating the user device with a study participant of the given health study,
generating a data collection configuration based on the given health study configuration, and
automatically transmitting the data collection configuration to the user device, wherein the data collection configuration is arranged to configure the user device for the collection of health-related data from a plurality of data sources associated with the user device;

receiving health-related data associated with a plurality of health study participants from the user devices associated with the health study participants via the configured data ingestion subsystem, the health-related data comprising data generated by a plurality of data collection activities performed using the user devices;

processing the received health-related data using the configured data processing subsystem, the processing including:
processing the health-related data received for each data collection activity to format the data in accordance with a common health data model; and
determining one or more derived health indicators from the formatted health-related data;

generating a study dataset using the derived health indicators; and outputting the study dataset.

18. A method according to claim 17, wherein the data collection activities comprise data collection activities associated with multiple data collection modes of a data collection application provided at a user device, wherein the processing step comprises formatting data generated by the multiple data collection modes in accordance with the common data model.

19. A method according to claim 18, wherein the data collection modes comprise one or more of:
a sensor-based data collection mode for receiving health-related data from one or more sensors included in or in communication with the user device;
a user data input mode for obtaining health-related data based on user input of a set of one or more health-related data values; and
an interactive health assessment mode for executing interactive assessments for obtaining health-related data based on user interaction with the user device.

20. A method according to claim 17, wherein the data collection activities comprise data collection activities associated with a plurality of sensors, the processing step comprising formatting data generated by the plurality of sensors in accordance with the common data model.

21. A method according to claim 17, wherein the determining step comprises computing at least one derived health indicator based on health-related data received for a plurality of data collection activities.

22. A method according to claim 17, wherein the common health data model comprises value data including at least a value field specifying a value of a health measure and a unit field specifying a unit of measurement applicable to the value, and further comprising one or more of: a data type field, and an identifier field identifying a type of the health measure.

23. A method according to claim 22, wherein the common health data model comprises key data associated with the value data comprising one or more of:
a source, a measurement event type, a user identifier, a device identifier, one or more acquisition timestamps; and start and end timestamps for an acquisition period.

24. A method according to claim 23, comprising storing the formatted health-related data including key and value data in a database to enable searching, querying and/or collation of health-related data based on one or more of the key data elements.

25. A method according to claim 17, comprising repeating the receiving, processing and determining steps for each of the plurality of study participants, and generating the study dataset using the derived health indicators for each of the study participants.

26. A method according to claim 17, wherein the derived health indicators comprise one or more health metrics associated with one or more outcome measures or end points of the study.

27. A method according to claim 17, comprising storing in a database one or more of:
the health-related data received from the devices; the formatted health-related data, and the derived health indicators, for a plurality of health studies managed by the health study management system.

28. A non-transitory computer-readable medium storing software code for execution by a health study management system, the health study management system adapted for collecting health-related data from a plurality of data sources, the health-related data comprising one or more of: data indicative of user health, and source data from which data indicative of user health can be derived, the data sources including a plurality of user devices associated with health study participants, the software code configured when executed to perform a method comprising:
providing a modular data ingestion subsystem comprising an extensible set of interface modules, each interface module adapted to receive health-related data from a respective type of data source;
providing a modular data processing subsystem comprising an extensible set of processing modules, each processing module adapted to process health-related data to determine one or more derived health indicators from the health-related data; and
receiving a given health study configuration for a given health study, from a plurality of health study configurations for a plurality of health studies, each health study configuration associated with a respective health study, wherein the given health study is to be conducted using the health study management system, the given health study configuration specifying a plurality of data collection activities for a plurality of study participants of the given health study, each data collection activity for collecting respective health-related data, the data collection activities specifying one or more sensor-based data collection activities associated with a sensor device type to be used for collecting sensor data, and processing to be performed on collected sensor data,
automatically configuring the data ingestion subsystem and data processing subsystem in accordance with the given health study configuration to receive and process health-related data for the given health study from the data sources;

for each of the plurality of user devices:
    associating the user device with a study participant of the given health study,
    generating a data collection configuration based on the given health study configuration, and
    automatically transmitting the data collection configuration to the user device, wherein the data collection configuration is arranged to configure the user device for the collection of health-related data from a plurality of data sources associated with the user device; and
wherein the software code is configured when executed to perform the steps of:
collecting the health-related data from the user devices via the configured data ingestion subsystem;
processing the collected health-related data using the configured data processing subsystem;
generating a study dataset based on the processed health-related data; and
outputting the study dataset.

29. A non-transitory computer-readable medium storing software code for execution by a health study management system, the health study management system adapted for collecting health-related data for a health study from a plurality of data sources, the health-related data comprising one or more of: data indicative of user health, and source data from which data indicative of user health can be computed, the data sources including a plurality of user devices associated with health study participants, the software code configured when executed to perform a method comprising:
    providing a modular data ingestion subsystem comprising an extensible set of interface modules, each interface module adapted to receive health-related data from a respective type of data source;
    providing a modular data processing subsystem comprising an extensible set of processing modules, each processing module adapted to process health-related data to determine one or more derived health indicators from the health-related data;
    receiving a given health study configuration for a given health study, from a plurality of health study configurations for a plurality of health studies, each health study configuration associated with a respective health study, wherein the given health study is to be conducted using the health study management system, the given health study configuration specifying a plurality of data collection activities for a plurality of study participants of the given health study, each data collection activity for collecting respective health-related data, the data collection activities specifying one or more sensor-based data collection activities associated with a sensor device type to be used for collecting sensor data, and processing to be performed on collected sensor data;
    automatically configuring the data ingestion subsystem and data processing subsystem in accordance with the given health study configuration to receive and process health-related data for the given health study from the data sources;
    for each of the plurality of user devices:
        associating the user device with a study participant of the given health study,
        generating a data collection configuration based on the given health study configuration, and
        automatically transmitting the data collection configuration to the user device, wherein the data collection configuration is arranged to configure the user device for the collection of health-related data from a plurality of data sources associated with the user device; and
    wherein the software code is configured when executed to perform the steps of:
    receiving health-related data associated with a plurality of study participants from the user devices associated with the study participants via the configured data ingestion subsystem, the health-related data comprising data generated by a plurality of data collection activities performed using the user devices;
    processing the received health-related data using the configured data processing subsystem, the processing including:
        processing the health-related data received for each data collection activity to format the data in accordance with a common health data model; and
        determining one or more derived health indicators from the formatted health-related data;
    generating a study dataset using the derived health indicators; and
    outputting the study dataset.

\* \* \* \* \*